(12) United States Patent
Kovacs et al.

(10) Patent No.: US 9,693,696 B2
(45) Date of Patent: *Jul. 4, 2017

(54) SYSTEM WITH USER-PHYSIOLOGICAL DATA UPDATES

(71) Applicant: PhysioWave, Inc., Santa Clara, CA (US)

(72) Inventors: Gregory T. Kovacs, Palo Alto, CA (US); Richard M. Wiard, Campbell, CA (US)

(73) Assignee: Physiowave, Inc., Santa Clara, CA (US)

(*) Notice: Subject to any disclaimer, the term of this patent is extended or adjusted under 35 U.S.C. 154(b) by 194 days.

This patent is subject to a terminal disclaimer.

(21) Appl. No.: 14/639,924

(22) Filed: Mar. 5, 2015

(65) Prior Publication Data

US 2016/0038038 A1    Feb. 11, 2016

Related U.S. Application Data

(63) Continuation of application No. 14/618,623, filed on Feb. 10, 2015, now Pat. No. 9,498,137.

(Continued)

(51) Int. Cl.
*A61B 5/00* (2006.01)
*A61B 5/0205* (2006.01)
(Continued)

(52) U.S. Cl.
CPC .......... *A61B 5/0205* (2013.01); *A61B 5/0295* (2013.01); *A61B 5/0402* (2013.01);
(Continued)

(58) Field of Classification Search
CPC ..... A61B 5/0205; A61B 5/0245; A61B 5/053; A61B 5/1102
See application file for complete search history.

(56) References Cited

U.S. PATENT DOCUMENTS 3,702,113 A    11/1972  Blockley et al.
4,195,643 A     4/1980  Pratt, Jr.
(Continued)

FOREIGN PATENT DOCUMENTS

DE    202009012748    12/2009
EP     0329306 A1      2/1989
(Continued)

OTHER PUBLICATIONS

I. Starr and F.C. Wood, "Twenty-Year Studies with the Ballistocardiograph: The Relation Between the Amplitude of the First Record of 'Healthy' Adults and Eventual Mortality and Morbidity from Heart Disease," Circulation, vol. 36, DD. 714-732 (1961).

(Continued)

*Primary Examiner* — Robert N Wieland
(74) *Attorney, Agent, or Firm* — Crawford Maunu PLLC

(57) ABSTRACT

Certain aspects of the instance disclosure are physiological data updates using a weighing scale and a user wearable device. Specific embodiments concern an arrangement of devices including a user wearable device and a weighing scale. The weighing scale is configured and arranged to monitor a plurality of physiological signals of the user using current-impedance electrodes and select data indicative of a physiological parameter of the user, for display on the user wearable device, based on a threshold value and the plurality of physiological signals.

19 Claims, 30 Drawing Sheets

Related U.S. Application Data

(60) Provisional application No. 62/034,582, filed on Aug. 7, 2014.

(51) Int. Cl.
*A61B 5/11* (2006.01)
*A61B 5/0402* (2006.01)
*A61B 5/0295* (2006.01)
*A61B 5/053* (2006.01)
*A61B 5/024* (2006.01)

(52) U.S. Cl.
CPC ............ *A61B 5/053* (2013.01); *A61B 5/1102* (2013.01); *A61B 5/6801* (2013.01); *A61B 5/6887* (2013.01); *A61B 5/742* (2013.01); *A61B 5/02416* (2013.01); *A61B 5/0535* (2013.01); *A61B 5/0537* (2013.01)

(56) References Cited

U.S. PATENT DOCUMENTS

| | | | |
|---|---|---|---|
| 4,362,164 A | 12/1982 | Little et al. |
| 4,557,271 A | 12/1985 | Stoller et al. |
| 4,657,025 A | 4/1987 | Orlando |
| 4,679,569 A | 7/1987 | Lee |
| 4,765,321 A | 8/1988 | Mohri |
| 4,836,215 A | 6/1989 | Lee |
| 4,947,857 A | 8/1990 | Albert et al. |
| 4,958,638 A | 9/1990 | Sharpe et al. |
| 5,314,389 A | 5/1994 | Dotan |
| 5,431,170 A | 7/1995 | Mathews |
| 5,620,003 A | 4/1997 | Sepponen |
| 5,678,562 A | 10/1997 | Sellers |
| 5,682,902 A | 11/1997 | Herleikson |
| 5,701,894 A | 12/1997 | Cherry et al. |
| 5,750,937 A | 5/1998 | Johnson et al. |
| 5,782,238 A | 7/1998 | Beitler |
| 5,833,623 A | 11/1998 | Mann et al. |
| 6,047,203 A | 4/2000 | Sackner et al. |
| 6,080,110 A | 6/2000 | Thorgersen |
| 6,168,563 B1 | 1/2001 | Brown |
| 6,198,394 B1 | 3/2001 | Jacobsen et al. |
| 6,205,547 B1 | 3/2001 | Davis |
| 6,228,033 B1 | 5/2001 | Koobi et al. |
| 6,292,690 B1 | 9/2001 | Petrucelli |
| 6,331,162 B1 | 12/2001 | Mitchell |
| 6,454,708 B1 | 9/2002 | Ferguson et al. |
| 6,454,719 B1 | 9/2002 | Greenhut |
| 6,516,221 B1 | 2/2003 | Hirouchi et al. |
| 6,551,252 B2 | 4/2003 | Sackner et al. |
| 6,594,759 B1 | 7/2003 | Wang |
| 6,640,134 B2 | 10/2003 | Raymond et al. |
| 6,685,634 B1 | 2/2004 | Fry |
| 6,702,754 B2 | 3/2004 | Ogura et al. |
| 6,705,990 B1 | 3/2004 | Gallant |
| 6,734,856 B2 | 5/2004 | Ishikawa et al. |
| 6,755,783 B2 | 6/2004 | Cosentino et al. |
| 6,783,498 B2 | 8/2004 | Sackner et al. |
| 6,790,178 B1 | 9/2004 | Mault et al. |
| 6,814,705 B2 | 11/2004 | Kawaguchi |
| 6,847,892 B2 | 1/2005 | Zhou et al. |
| 6,875,174 B2 | 4/2005 | Braun et al. |
| 6,898,299 B1 | 5/2005 | Brooks |
| 6,962,566 B2 | 11/2005 | Quistgaard et al. |
| 6,963,035 B2 | 11/2005 | Honda et al. |
| 7,137,955 B2 | 11/2006 | Bartels et al. |
| 7,257,438 B2 | 8/2007 | Kinast |
| 7,313,435 B2 | 12/2007 | Nakada et al. |
| 7,316,648 B2 | 1/2008 | Kelly et al. |
| 7,382,247 B2 | 6/2008 | Welch et al. |
| 7,384,410 B2 | 6/2008 | Eggers et al. |
| 7,417,536 B2 | 8/2008 | Lakshmanan et al. |
| 7,459,644 B2 | 12/2008 | Kenmochi |
| 7,502,643 B2 | 3/2009 | Farringdon et al. |
| 7,668,588 B2 | 2/2010 | Kovacs |
| 7,787,946 B2 | 8/2010 | Stahmann et al. |
| 7,796,013 B2 | 9/2010 | Murakami et al. |
| 7,846,104 B2 | 12/2010 | MacQuarrie et al. |
| 7,899,522 B1 | 3/2011 | Koh et al. |
| 8,369,936 B2 | 2/2013 | Farringdon et al. |
| 8,452,390 B2 | 5/2013 | Jensen |
| 8,473,041 B2 | 6/2013 | Bartnik et al. |
| 8,475,367 B1 | 7/2013 | Yuen et al. |
| 8,529,409 B1 | 9/2013 | Lesea-Ames |
| 8,548,556 B2 | 10/2013 | Jensen |
| 8,639,226 B2 | 1/2014 | Hutchings et al. |
| 8,682,424 B2 | 3/2014 | Tsoglin et al. |
| 8,698,014 B1 | 4/2014 | Walstad |
| 8,858,449 B2 | 10/2014 | Inan et al. |
| 8,870,780 B2 | 10/2014 | Inan et al. |
| 9,011,346 B2 | 4/2015 | Wiard et al. |
| 9,055,871 B2 | 6/2015 | Inan et al. |
| 9,215,991 B2 | 12/2015 | Inan et al. |
| 9,241,637 B2 | 1/2016 | Wiard et al. |
| 2001/0030546 A1 | 10/2001 | Yamada et al. |
| 2001/0044588 A1 | 11/2001 | Mault |
| 2002/0002326 A1 | 1/2002 | Causey, III et al. |
| 2002/0062090 A1 | 5/2002 | Chai et al. |
| 2002/0188205 A1 | 12/2002 | Mills |
| 2003/0050537 A1 | 3/2003 | Wessel |
| 2003/0088196 A1 | 5/2003 | Steve |
| 2003/0126593 A1 | 7/2003 | Mault |
| 2003/0130567 A1 | 7/2003 | Mault et al. |
| 2003/0130595 A1 | 7/2003 | Mault |
| 2003/0149349 A1 | 8/2003 | Jensen |
| 2003/0197614 A1 | 10/2003 | Smith et al. |
| 2003/0233034 A1 | 12/2003 | Varri et al. |
| 2004/0068379 A1 | 4/2004 | Morgan et al. |
| 2004/0073127 A1 | 4/2004 | Istvan et al. |
| 2004/0097802 A1 | 5/2004 | Cohen |
| 2004/0138517 A1 | 7/2004 | Osorio et al. |
| 2004/0211599 A1 | 10/2004 | Kasinoff |
| 2004/0249258 A1 | 12/2004 | Tupin, Jr. et al. |
| 2005/0004483 A1 | 1/2005 | Lin |
| 2005/0017602 A1 | 1/2005 | Arms et al. |
| 2005/0033124 A1 | 2/2005 | Kelly et al. |
| 2005/0043645 A1 | 2/2005 | Ono et al. |
| 2005/0113703 A1 | 5/2005 | Farringdon et al. |
| 2005/0119711 A1 | 6/2005 | Cho et al. |
| 2005/0171451 A1 | 8/2005 | Yeo et al. |
| 2005/0203349 A1 | 9/2005 | Nanikashvili |
| 2005/0206518 A1 | 9/2005 | Welch et al. |
| 2005/0247494 A1 | 11/2005 | Montagnino |
| 2005/0283198 A1 | 12/2005 | Haubrich et al. |
| 2006/0049955 A1 | 3/2006 | Blum et al. |
| 2006/0079942 A1 | 4/2006 | Deno et al. |
| 2006/0106646 A1 | 5/2006 | Squilla et al. |
| 2006/0111641 A1 | 5/2006 | Manera et al. |
| 2006/0116589 A1 | 6/2006 | Park |
| 2006/0122525 A1 | 6/2006 | Shusterman |
| 2006/0149139 A1 | 7/2006 | Bonmassar et al. |
| 2006/0154642 A1 | 7/2006 | Scannell |
| 2006/0155589 A1 | 7/2006 | Lane et al. |
| 2007/0055324 A1 | 3/2007 | Thompson et al. |
| 2007/0069887 A1 | 3/2007 | Welch et al. |
| 2007/0161913 A1 | 7/2007 | Farrell et al. |
| 2007/0197878 A1 | 8/2007 | Shklarski |
| 2007/0208232 A1 | 9/2007 | Kovacs |
| 2007/0293770 A1 | 12/2007 | Bour et al. |
| 2008/0027679 A1 | 1/2008 | Shklarski |
| 2008/0073128 A1 | 3/2008 | Umemoto |
| 2008/0154645 A1 | 6/2008 | Takehara |
| 2008/0161700 A1 | 7/2008 | Sachanandani et al. |
| 2008/0183090 A1 | 7/2008 | Farringdon et al. |
| 2008/0194975 A1 | 8/2008 | MacQuarrie et al. |
| 2008/0208009 A1 | 8/2008 | Shklarski |
| 2008/0221404 A1 | 9/2008 | Tso |
| 2008/0246629 A1 | 10/2008 | Tsui et al. |
| 2008/0281222 A1 | 11/2008 | Fukada |
| 2008/0306393 A1 | 12/2008 | Ting et al. |
| 2009/0024044 A1 | 1/2009 | Virtanen et al. |
| 2009/0102296 A1 | 4/2009 | Greene et al. |
| 2009/0182204 A1 | 7/2009 | Semler et al. |
| 2009/0203972 A1 | 8/2009 | Heneghan et al. |

(56) References Cited

U.S. PATENT DOCUMENTS

| | | |
|---|---|---|
| 2009/0284496 A1 | 11/2009 | Oki |
| 2009/0315733 A1 | 12/2009 | Bischoff |
| 2010/0004715 A1 | 1/2010 | Fahey |
| 2010/0016685 A1 | 1/2010 | Muehlsteff et al. |
| 2010/0094147 A1 | 4/2010 | Inan et al. |
| 2010/0210921 A1 | 8/2010 | Park et al. |
| 2010/0262044 A1 | 10/2010 | Siegler |
| 2011/0040352 A1 | 2/2011 | Gerber et al. |
| 2011/0054359 A1 | 3/2011 | Sazonov et al. |
| 2011/0240379 A1 | 10/2011 | Forshaw et al. |
| 2011/0245710 A1 | 10/2011 | Jensen |
| 2011/0310005 A1 | 12/2011 | Chen |
| 2012/0003933 A1 | 1/2012 | Baker et al. |
| 2012/0065895 A1 | 3/2012 | Saul |
| 2012/0071792 A1 | 3/2012 | Pfeffer et al. |
| 2012/0123219 A1 | 5/2012 | Georgiev et al. |
| 2012/0165622 A1 | 6/2012 | Rodriguez et al. |
| 2012/0245476 A1 | 9/2012 | Skerl et al. |
| 2012/0283587 A1 | 11/2012 | Gosh et al. |
| 2012/0302843 A1 | 11/2012 | Otsubo et al. |
| 2012/0318869 A1 | 12/2012 | Edmonds |
| 2013/0056285 A1 | 3/2013 | Meagher |
| 2013/0113506 A1 | 5/2013 | Poupyrev et al. |
| 2013/0289889 A1 | 10/2013 | Yuen et al. |
| 2013/0310700 A1 | 11/2013 | Wiard et al. |
| 2014/0089836 A1 | 3/2014 | Damani et al. |
| 2014/0094707 A1 | 4/2014 | Farringdon et al. |
| 2014/0121540 A1 | 5/2014 | Raskin |
| 2014/0142396 A1 | 5/2014 | Ricks et al. |
| 2014/0142437 A1 | 5/2014 | Inan et al. |
| 2014/0172314 A1 | 6/2014 | Baarman |
| 2014/0221849 A1 | 8/2014 | Farringdon et al. |
| 2014/0221850 A1 | 8/2014 | Farringdon et al. |
| 2015/0107910 A1 | 4/2015 | Villard et al. |
| 2015/0112209 A1 | 4/2015 | Blaber et al. |
| 2015/0160068 A1 | 6/2015 | Carreel et al. |
| 2015/0168205 A1 | 6/2015 | Lee |
| 2015/0201844 A1 | 7/2015 | Nakagawa |
| 2015/0289802 A1 | 10/2015 | Thomas et al. |
| 2015/0331491 A1 | 11/2015 | Rumreich |
| 2015/0335291 A1 | 11/2015 | Saadi et al. |
| 2015/0338265 A1 | 11/2015 | Carreel et al. |
| 2016/0029905 A1 | 2/2016 | Kovacs |
| 2016/0116326 A1* | 4/2016 | Sharma ................ G01G 19/44 177/1 |
| 2016/0317043 A1 | 11/2016 | Campo et al. |

FOREIGN PATENT DOCUMENTS

| | | |
|---|---|---|
| ES | 2296474 A1 | 4/2008 |
| ES | 2328205 B1 | 8/2010 |
| ES | 2385898 A1 | 8/2012 |
| ES | 2398439 A2 | 3/2013 |
| ES | 2398542 A2 | 3/2013 |
| GB | 2225459 | 5/1990 |
| GB | 2367896 A | 4/2002 |
| JP | 2001198096 | 7/2001 |
| JP | 2001309893 | 11/2001 |
| JP | 2002119488 | 4/2002 |
| JP | 2006212155 | 8/2006 |
| JP | 2007283071 A | 11/2007 |
| JP | 2009050508 A | 3/2009 |
| KR | 0137272 B1 | 4/1998 |
| KR | 20050079235 A | 8/2005 |
| WO | 2005074379 A2 | 8/2005 |
| WO | 2006088280 A1 | 8/2006 |
| WO | 2007103835 A2 | 9/2007 |
| WO | 2008102298 A1 | 8/2008 |
| WO | 2010004502 A1 | 1/2010 |
| WO | WO2010004502 | 1/2010 |
| WO | 2010045455 A1 | 4/2010 |
| WO | 2011075767 A1 | 6/2011 |
| WO | WO2012103296 | 8/2012 |
| WO | 2013017717 A2 | 2/2013 |
| WO | 2013066642 A1 | 5/2013 |

OTHER PUBLICATIONS

D.C. Deuchar, S.A. Talbot, and W.R. Scarborough, "Some Observations on the Relation of the High-Frequency Bed Ballistocardiogram to that Obtained from an Aperiodic Bed," Circulation, vol. 11, pp, 228-239 (1955).

H. Mandelbaum and R.A. Mandelbaum, "Studies Utilizing the Portable Electromagnetic Ballistocardiograph: IV. The Clinical Significance of Serial Ballistocardiograms Following Acute Myocardial Infarction," Circulation, vol. 7, pp. 910-9165 (1953).

R.S. Guber, M. Rodstein and H.E. Ungerleider, "Ballistocardiograph: An Appraisal of Technic, Physiological Principles, and Clinic Value," Circulation, vol. 7, DD. 268-286 (1953).

M.B. Rappaport, H.B. Sprague, and W.B. Thompson, "Ballistocardiography: I. Physical Considerations," Circulation, vol. 7, pp. 229-246 (1953).

0. Tannenbaum, J. Schack and H. Vesell, "Relationship between Ballistocardiographic Forces and Certain Events in the Cardiac Cycle," Circulation, vol. 6, DD. 586-592 (1952).

T.E. Satterthwaite, "Cardiovascular Diseases: Recent Advances in Their Anatomy, Physiology, Pathology, Diagnosis and Treatment," Lemcke and Beuschner, New York, NY (1913).

J.W. Gordon, "On Certain Molar Movements of the Human Body Produced by the Circulation of the Blood," J. of Anat. and Phys., vol. 11, DD. 533-536 (1877).

Gonzalez, et al. "Deteccion of las frecuencias 1-9 cardiaca and respiratoria mediante una bascu the electronica" In: IFMBE Proceedings. vol. 18, pp. 448-451, 2008. Springer-Verlag Berlin Heidelberg. Abstract Only.

Gomez-Clapers J. et al. "Pulse arrival time estimation from the impedance plethysmogram obtained with a handheld device", 33rd Annual International Conference of the IEEE EMBS, Boston, USA, Mar. 8-9, 2011, pp. 516-519. Abstract only.

HeartForce Medical Inc. "definitions and Terminologies: History of Seismocardiology." www.heartforcemedical.com 4 pages.

Shin et al., "Non-constrained monitoring of systolic blood pressure on a seighing scale", Physiological Measurement, vol. 30, No. 7, pp. 679-693, 2009 Abstract Only.

Pliquett et al., "Front end with offset-free symmetrical current source optimized for time domain impedance spectroscopy", Physiological Measurement, vol. 32, No. 7, 2011.I Abstract Only.

Earbud Ballistocardiogram: HeadSense Israel: http://head-sense-med.com/ http://www.medgadget.com/2013/07/headsense-intracranial-pressure-monitoring-earbuds.html.

Bifrostec & The Kaiteki Institute http://www.psfk.com/2013/11/earbud-heart-monitor.html#!zIKRT.

http://www.endgadget.com/2014/01/06/intel-smart-earbuds/.

Mitchell et al., "Arterial Stiffness and Cardiovascular Events The Framingham Heart Study" . Circulation 2010, 121: 505-11.

Blacher et al., "Impact of Aortic Stiffness on Survival in End-Stage Renal Disease" Circulation, 1999: 99.

Blacher et al., "Arterial Calcifications, Arterial Stiffness, and Cardiovascular Risk in End Stage Renal Disease" Hypertension. 38: 938-942 (2001).

Di Micco, et al., "Daily dialysis reduces pulse wave velocity in chronic hemodialysis patients". Hypertension Research. vol. 35, 2012.

J. Alametsä et al. "Ballistocardiogaphic studies with acceleration and electromechanical film sensors." Medical Engineering & Physics 31 (2009), p. 1154-1165.

J. Alametsä et al. "Arterial Elasticity Measurements with Ankle Pulse Width Velocity and Ballistocardiography." ECIFMBE 2008, IFMBE Proceedings 22, p. 1636-1641.

J. Allen. "Photoplethysmography and its application in clinical physiological measurement." Physiol. Meas. 28, 2007, p. R1-R39.

A. Avolio et al. "Role of Pulse Pressure Amplification I Arterial Hpertension: Experts' Opinion and Review of the Data." Hypertension, vol. 54, Aug. 1, 2009, p. 375-383.

(56) References Cited

OTHER PUBLICATIONS

J. Blacher et al. "Aortic Pulse Wave Velocity as a Marker of Cardiovascular Risk in Hypertensive Patients," Hypertension, vol. 33, 1999, p. 1111-1117.
Davis, S; B. van den Bogaard et al. "Active standing reduces wave reflection in the presence of increased peripheral resistance in young and old healthy individuals." J Hypertension (4) Apr. 29, 2011, p. 682-689 (Abstract); and B. van den Bogaard. "Chapter 12: Active standing reduces wave reflection in the presence of increased peripheral resistance in young and old healthy individuals." Dissertation, Univ. Amsterdam, 2012, p. 180-193.
G. Kim et al. "Vascular Variation of PTT and the Vascular Characteristic Index According to the Posture Change." In Proceedings of the 2007 International Conference on Convergence Information Technology (ICCIT '07). IEEE Computer Society, Nov. 2007, p. 2426-2425. Abstract Only.
E. Pinheiro et al. "Non-Intrusive Device for Real-Time Circulatory System Assessment with Advanced Signal Processing Capabilities." Measurement Science Review, vol. 10, No. 5, 2010, p. 167-175.
E. Pinheiro et al. "Pulse arrival time and ballistocardiogram application to blood pressure variability estimation." Medical Measurements and Applications, 2009. IEEE Workshop, May 29-30, 2009. Abstract only.
M. Safar. "Arterial aging—hemodynamic changes and therapeutic options." Nat Rev Cardiol, vol. 7, 207, p. 442-449. Abstract / Introduction Only.
R. Wiard et al. "Estimation of Central Aortic Forces in the Ballistocardiogram under Rest and Exercise Conditions." 31st Annual International Conference of the IEEE EMBS, Sep. 2-6, 2009, p. 2831-2834.
R. Wiard et al. "Automatic detection of motion artifacts in the ballistocardiogram measured on a modified bathroom scale." Med Biol Eng Comput (2011) 49:213-220. Published online Dec. 9, 2010.
B. Williams et al. "Differential Impact of Blood Pressure-Lowering Drugs on Central Aortic Pressure and Clinical Outcomes: Principal Results of the Conduit Artery Function Evaluation (CAFE) Study," Circulation, vol. 113, Feb. 13, 2006, p. 1213-1225.
O.T. Inan, M. Etemadi, R.M. Wiard, L. Giovangrandi, and G. T. A. Kovacs, "Robust Ballistocardiogram Acquisition for Home Monitoring," Phys. Meas., vol. 30, No. 2, pp. 169-185 (2009).
Inan OT, Etemadi M, Paloma A, Giovangrandi L, Kovacs GTA (2009) Non-invasive cardiac output trending during exercise recovery on a bathroom-scale-based ballistocardiograph. Physiol Meas 30:261-274 Abstract / Introduction Only.
Irian OT, Etemadi M, Wiard RM, Kovacs GTA, Giovangrandi L (2009) Novel methods for estimating the ballistocardiogram signal using a simultaneously acquired electrocardiogram. In: 31st annual IEEE engineers in medicine and biology conference. IEEE, Minneapolis, MN Abstract / Introduction Only.
Irian OT, Kovacs GTA, Giovangrandi L (2010) Evaluating the lower-body electromyogram signal acquired from the feet as a noise reference for standing ballistocardiogram measurements. IEEE Trans Inf Technol Biomed 14:1188-1196 Abstract / Introduction Only.
DeLoach SS, Twonsend RR, "Vascular Stiffness: Its Measurement and Significance for Epidemiologic and Outcome Studies", Clin J Am Soc Nephrol, 3: 184-192, 2008. Abstract / Introduction Only.
Webster's Ninth New Collegiate Dictionary, Meriam-Webster Inc., 1990, p. 1152.
Alan Fang et al., "Using a Geophone for Vibration Cancellation in a STM," abstract, Bulletin of the American Physical Society, 2008 APS March Meeting, vol. 53, No. 2, Mar. 10, 2008.
De Vides, S. O. et al., "Prediction of the Left Ventricular Mass from the Electrogram in Systemic Hypertension," American Journal of Cardiology, May 1, 1996;777(11):974-8. (Abstract Only).

A.Akhbardeh, M. Koivuluoma, T. Koivistoinen and A. Varri, "Ballistocardiogram Diagnosis Using Neural Networks and Shift-Invariant Daubechies Wavelet Transform," Researchers at Institute of Signal Processing, Tampere University ofTechnology, Tampere 33101, Finland.
O. Inan, et al. "Evaluating the Foot Electromyogram Signal as a Noise Reference for a Bathroom Scale Ballistocardiogram Recorder," Stanford University, Department of EE, Department of Bioengineering.
0. Inan and G Kovacs, "An 11 µW, Two-Electrode Transimpedance Biosignal Amplifier with Active Current Feedback Stabilization," IEEE Transactions on Biomedical Circuits and Systems (2009).
0. Inan, M. Etemadi, B. Widrow and G. Kovacs, "Adaptive cancellation of floor vibrations in standing ballistocardiogram measurements using a seismic sensor as a noise reference," IEEE (2009).
R. F. Yazicioglu, P. Merken, R. Puers and C. Van Hoof, "A 60 µW 60 nV/..JHz Readout Front-End for Portable Biopotential Acquisition Systems," IEEE Journ. Of Solid-State Circuits, vol. 42, No. 5 (May 2007).
W. Rosamond et al., "Heart Disease and Stroke Statistics—2007 Update: A Report from the American Heart Association Statistics Committee and Stroke Statistics Subcommittee," Circ., v. 115, pp. 69-171 (2007).
R. R. Harrison, "A Versatile Integrated Circuit for the Acquisition of Biopotentials," IEEE CICC, pp. 115-122 (2007).
T. Denison, K. Consoer, W. Santa, A.-T. Avestruz, J. Cooley, and A. Kelly, "A 2µW JOO nV/rtHz, Chopper-Stabilized Instrumentation Amplifier for Chronic Measurement of Neural Field Potentials," IEEE Jour. Solid-State Circuits, v. 42, No. 12, DD. 2934-2945 (2007).
A.Akhbardeh, S. Junnila, M. Koivuluoma, T. Koivistoinen, V. Turjanmaa, T. Koobi, and A. Viirri, "Towards a heart disease diagnosing system based on force sensitive chair's measurement, biorthogonal wavelets and neural networks," ScienceDirect, Engineering Applications for Artificial Intelligence, pp. 1-10 (2006).
D. Corrado, C. Basso, A. Pavel, P. Michieli, M. Schiavon, and G. Thiene, "Trends in Sudden Cardiovascular Death in Young Competitive Athletes After Implementation of a Preparticipation Screening Program," JAMA, vol. 296, No. 13, pp. 1593-1601 (Oct. 4, 2006).
C.N. Chien and F.S. Jaw, "Miniature ultra-low-power biopotential amplifier for potable [sic} applications," Biomedical Engineering-Applications, Basis & Communications, vol. 17, No. 2, pp. 11-49 (Apr. 2005).
C.W. Mundt, K.N. Montgomery, U.E. Udoh, V.N. Barker, G.C. Thonier, A.M. Tellier, R.D. Ricks, R.B. Darling, Y.D. Cagle, N.A. Cabrol, S.J. Ruoss, J.L. Swain, J.W. Hines, and G.T.A. Kovacs, "A Multiparameter Wearable Physiologic Monitoring System for Space and Terrestrial Applications," IEEE Trans. Inform. Tech. in Biomed., vol. 9, No. 3, pp. 382-391 (Sep. 2005).
M. Shojaei-Baghini, R.K. Lal, and D.K. Sharma, "A Low-Power and Compact Analog CMOS Processing Chip for Portable ECG Recorders," Proc. IEEE A.S.S.C.C., DD. 473-476 (2005).
J. Alametsii, A. Viirri, M. Koivuluoma, and L. Barna, "The Potential of EMFi Sensors in Heart Activity Monitoring," 2nd OpenECG Workshop "Integration of the ECG into the EHR & Interoperability of ECG Device Systems," Apr. 1-3, 2004 Berlin, Germany.
E. Company-Bosch and E. Hartmann, "ECG Front-End Design is Simplified with MicroConverter," Analog Dialogue, 37-11, pp. 1-5 (Nov. 2003).
D.M. Linton and u. Giion, "Advances in noninvasive cardiac output monitoring," Annals of cardiac Anaesthesia, vol. 5, pp. 141-148 (2002).
M. Watanabe, J. Marine, R. Sheldon, and 1\1. Josephson, "Effects of Ventricular Premature Stimulus Coupling Interval on Blood Pressure and Heart Rate Turbulence," Circ., vol. 106, pp. 325-330 (2002).
K. Lu, J. W. Clark, Jr. F. H. Ghorbel, D. L. Ware, and A. Bidani, "A human cardiopulmonary system model applied to the analysis of the Valsalva maneuver," Am. J Physiol. Heart Circ. Physiol., vol. 281, pp. H2661-H2679 (2001).

(56) References Cited

OTHER PUBLICATIONS

J. Rapoport, D. Teres, J. Steingrub, T. Higgins, W. McGee, and S. Lemeshow, "Patient characteristics and ICU organizational factors that influence frequency of pulmonary artery catheterization," JAMA, vol. 283, No. 19, pp. 2559-2567 (2000).

B.D. Johnson, K.C. Beck, D.N. Proctor, J. Miller, N.M. Dietz, and M.J. Joyner, "Cardiac output during exercise by the open circuit acetylene washin method: comparison with direct Fick," J. Appl Physiol, vol. 88, pp. 1650-1658 (2000).

W. Klimesch, "EEG alpha and theta oscillations reflect cognitive and memory performance: a review and analysis," Brain Research Reviews, vol. 29, DD. 169-195 (1999).

D. Corrado, C. Basso, M. Schiavon, and G. Thiene, "Screening for Hypertrophic Cardiomyopathy in Young Athletes," NEJM, vol. 339, pp. 364-369 (Aug. 6, 1998).

A.C. MettingVanRijn, A. Peper and C.A. Grimbergen, "Amplifiers for bioelectric events: a design with a minimal number of parts," Med. & Biol. Eng. & Comput., vol. 32, DD. 305-310 (1994).

R. Moore, R. Sansores, V. Guimond, and R. Abboud, "Evaluation of cardiac output by thoracic electrical bioimpedance during exercise in normal subjects," American College of Chest Physicans, vol. 102, DD. 448-455 (1992).

J. Christie, L.M. Sheldahl, F.E. Tristani, K.B. Sagar, M.J. Ptacin, and S. Wann, "Determination of stroke volume and cardiac output during exercise: comparison of two-dimensional and Doppler echocardiography, Fick oximetry, and thermodilution," Circ., vol. 76, DD. 539-547 (1987).

H. Benjelloun, R. Itti, L. Philippe, J.M. Lorgeron and M. Brochier, "Beat-to-Beat Assessment of Left Ventricular Ejection in Atrial Fibrillation," European Journal Nuclear Medicine, vol. 8, pp. 206-210 (1983).

S. Grimnes, "Impedance measurement of individual skin surface electrodes," Med. & Biol. Eng. & Comput., vol. 21, DD. 750-755 (1983).

Y. Miyamoto, M. Takahashi, T. Tamura, T. Nakamura, T. Hiura, and M. Mikami, "Continuous determination of cardiac output during exercise by the use of impedance plethysmogrphy," Med. Biol. Eng. Comp., vol. 19, DD. 638-644, (1981).

R.P. Lewis, S.E. Rittogers, W.F. Froester, and H. Boudoulas, "A critical review of the systolic time intervals," Circulation, vol. 56, DD. 146-158 (1977).

European Patent Office, Third Examination Report Mailed Nov. 26, 2014 for EPO Patent Application No. 07757854.0. which claims priority from PCT Application No. PCT/US2007/063244.

China State Intellectual Property Office, Office Action Mailed Oct. 13, 2010 for CN Patent Application No. 200780015788.1.

Japan Patent Office, Notice of Reasons for Rejection dispatched Mar. 6, 2012 for JPO Patent Application No. P2008-558484. which claims priority from PCT Application No. PCT/US2007/063244; Reference 1 cited in the Notice of Reaons for Rejection corresponds to U.S. Appl. No. 08/555,546, issued as U.S. Pat. No. 5,701,894, Cherry et al., which is cited above; Reference 2, US 20030050537, Wessel, is cited above.

European Patent Office, Extended European Search Report Mailed Feb. 12, 2010 for EPO Application No. 07757854.0.

International Search Report and Written Opinion of the International Searching Authority for PCT International App. No. PCT/US07/63244.

Discera, "Shrinking Wireless Architectures", available for download from www.discera.com prior to Mar. 3, 2006.

GeTeMed GmbH, "Baby Monitoring System Vitaguard VG3000", Teltow, Germany, 1997-1999.

Atmel, "Microcontroller with 16 K Bytes In-System Programmable Flash", Atmel Atmega, document contains notation AVR 06/05.

Kaminska, Wireless Wearable Biomonitors for Lifetime Wellness Optimization, Proceedings of the 3rd Annual International IEEE EMBS Special Topic Conference on Microtechnologies in Medicine and Biology, Kahuku, Oahu, Hawaii, May 2005. Abstract Only.

NorthEast Monitoring Inc., "Holter LX Pro Software—Operator's Manual", NorthEast Monitoring Inc. Two Clock Tower Suite 360 Maynard Massachusetts 01754, Apr. 2003.

Nguyen et al., "Transceiver Front-End Architectures Using Vibrating Micromechanical Signal Processors", Dig. of Papers, Topical Meeting on Silicon Monolithic Integrated Circuits in RF Systems: 23-32, Sep. 4, 2001.

ANSI/AAMI, EC11:1991/(R) 2001, Diagnostic Electrogardiographic Devices, 2000.

ANSI/MM I, EC38: 1998, Ambulatory Electrocardiographs, 1999.

Nguyen et al., "Frequency-Selective MEMS for Miniaturized Low-Power Communication Devices", IEEE Trans. Microwave Theory Tech 47(8):1486-1503, Aug. 1999.

Nguyen et al., "An Integrated CMOS Micromechanical Resonator High-Q Oscillator", IEEE Journal of Solid-State Circuits 34(4), Apr. 1999.

Nguyen et al., "Micromachined Devices for Wireless Communications," Proc. IEEE 86(8):1756-1768, Aug. 1998.

Kovacs, "Micromachined Transducers-Sourcebook", McGraw-Hill, New York, New York, 1998 944 page book Book Description provided.

Desel et al., "A CMOS Nine Channel ECG Measurement IC", ASIC 1996 2nd International Conference: 115-118, Oct. 1996 Abstract Only.

Fraunhofer, "Medical Technolology", http://www.iis.fraunhofer.de/en/ff/med.html Dec. 26, 2005.

Toumaz "Technology", Nov. 8, 2005.

Kaminiski, "Wearable Biomonitors With Wireless Network Communication" draft of paper published in Proceedings of the 3rd Annual International IEEE EMBS Special Topic Conference on Microtechnologies in Medicine and Biology, Kahuku, Oahu, Hawaii, May 2005.

Novosense AB, "Company", Apr. 4, 2005.

IMEC, "Sensor Electronics", Mar. 31, 2005.

Novosense, AB, "Technology", available for download at http://www.novosense.se/technology.html Aug. 5, 2015.

Miromico AG, "Sample Projects", available for dowolcad at http.//www.miromico.ch/index.php?sec-ad.sa&lang=2, page includes notice of Copyright 2005 Miromico.

Mori, Narumi, et al. "Clinical assessment of a new method for pacing pulse detection using a hybrid circuit in digital Holter monitoring." Japanese circulation journal 64.8 (2000): 583-589.

Pyron, "Pyron Introduces ECG ASIC Monitoring Subsystem", Electronic News, Nov. 29, 1999.

Nguyen, Clark T-C., and Roger T. Howe. "An integrated CMOS micromechanical resonator high-Q oscillator." Solid-State Circuits, IEEE Journal of 34.4 (1999): 440-455.

Grossbach, Wolfgang. "Measuring the ECG Signal with a Mixed Analog-Digital Application-Specific IC." Hewlett-Packard Journal 42.4 (1991): 21-24. Abstract Only.

Laurent S et al., "Expert consensus document on arterial stiffness: methodological issues and clinical applications", European Heart Journal (2006) 27, 2588-2605.

Boutouyrie P et al., "Assessment of arterial stiffness for clinical and epidemiological studies: methodological considerations for validation and entry into the European Renal and Cardiovascular Medicine registry", Nephrol Dial Transplant (2014) 29: 232-239.

Stewart A D. et al., "Acute Reduction of Blood Pressure by Nitroglycerin Does Not Normalize Large Artery Stiffness in Essential Hypertension", Hypertension 2006, 48: 404-410.

Stewart A D. et al., "Effects of Inhibition of Basal Nitric Oxide Synthesis on Carotid-Femoral Pulse Wave Velocity and Augmentation Index in Humans", Hypertension 2003, 42: 915-918.

Avolio A P., et al., "Effects of aging on changing arterial compliance and left ventricular load in a northern Chinese urban community", Circulation 68, No. 1, 50-58, 1983.

Wilkinson, I B. et al., "ARTERY Society guidelines for validation of non-invasive haemodynamic measurement devices: Part 1, arterial pulse wave velocity" Artery Research (2010) 4, 34-40.

Avolio A P., et al. "Improved Arterial Distensibility in Normotensive Subjuects on a Low Salt Diet", Arteriosclerosis 6: 166-169, 1986.

(56) References Cited

OTHER PUBLICATIONS

Balkestein E J., et al., "The effect of weight loss with or without exercise training on large artery compliance in healthy obese men", J. Hypertens 1999, 17: 1831-1835.

Laurent S, et al., "Mesure de la Rigidite Arterielle" Dec. 2013.

Wiard, Richard M., et al. "Preliminary results from standing ballistocardiography measurements in microgravity." 2013 35th Annual International Conference of the IEEE Engineering in Medicine and Biology Society (EMBC). IEEE, 2013. Abstract only.

Inan, Omer T., et al. "Noninvasive measurement of physiological signals on a modified home bathroom scale." IEEE Transactions on Biomedical Engineering 59.8 (2012): 2137-2143. Abstract only.

Giovangrandi, Laurent, et al. "Preliminary results from BCG and ECG measurements in the heart failure clinic." 2012 Annual International Conference of the IEEE Engineering in Medicine and Biology Society. IEEE, 2012. Abstract only.

Park, Dookun, Omer T. Inan, and Laurent Giovangrandi. "A combined heartbeat detector based on individual BCG and IPG heartbeat detectors." 2012 Annual International Conference of the IEEE Engineering in Medicine and Biology Society. IEEE, 2012. Abstract only.

Etemadi, Mozziyar, et al. "Rapid assessment of cardiac contractility on a home bathroom scale." IEEE transactions on information technology in biomedicine 15.6 (2011): 864-869. Abstract only.

Giovangrandi, L., et al. "Ballistocardiography—a method worth revisiting." Conference proceedings: . . . Annual International Conference of the IEEE Engineering in Medicine and Biology Society. IEEE Engineering in Medicine and Biology Society. Annual Conference. vol. 2011. NIH Public Access, 2010.

Inan, Omer T., et al. "Multi-signal electromechanical cardiovascular monitoring on a modified home bathroom scale." 2011 Annual International Conference of the IEEE Engineering in Medicine and Biology Society. IEEE, 2011. Abstract only.

Wiard, R. M., et al. "Estimation of central aortic forces in the ballistocardiogram under rest and exercise conditions." Conference proceedings: . . . Annual International Conference of the IEEE Engineering in Medicine and Biology Society. IEEE Engineering in Medicine and Biology Society. Annual Conference. vol. 2009. NIH Public Access, 2008.

Etemadi, Mozziyar, et al. "Non-invasive assessment of cardiac contractility on a weighing scale." 2009 Annual International Conference of the IEEE Engineering in Medicine and Biology Society. IEEE, 2009. Abstract only.

Inan, Omer T., et al. "Non-invasive measurement of valsalva-induced hemodynamic changes on a bathroom scale ballistocardiograph." 2008 30th Annual International Conference of the IEEE Engineering in Medicine and Biology Society. IEEE, 2008. Abstract only.

Inan, Omer T., et al. "Unobtrusive Monitoring of Cardiovascular Health at Home Using a Modified Weighing Scale." 6th European Conference of the International Federation for Medical and Biological Engineering. Springer International Publishing, 2015. Abstract only.

McCall, Corey, et al. "Standing ballistocardiography measurements in microgravity." 2014 36th Annual International Conference of the IEEE Engineering in Medicine and Biology Society. IEEE, 2014. Abstract only.

Inan, Omer Tolga. Novel technologies for cardiovascular monitoring using ballistocardiography and electrocardiography. vol. 70. No. 10. 2009. Copy unavailable.

Wiard, Richard Matthew. Validation of Non-invasive Standing Arterial Stiffness Measurements Using Ballistocardriography and Photoplethysmography. 2012. Abstract only.

* cited by examiner

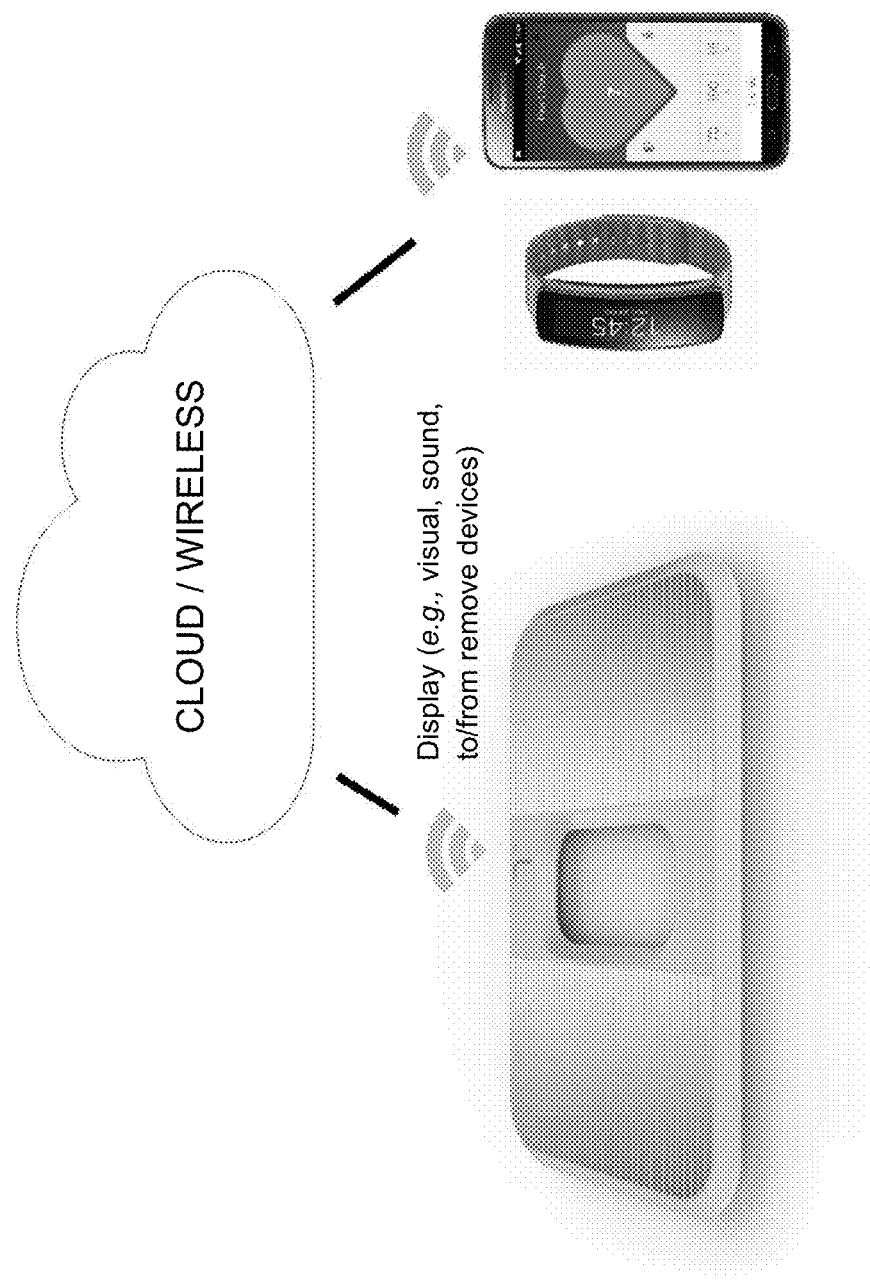

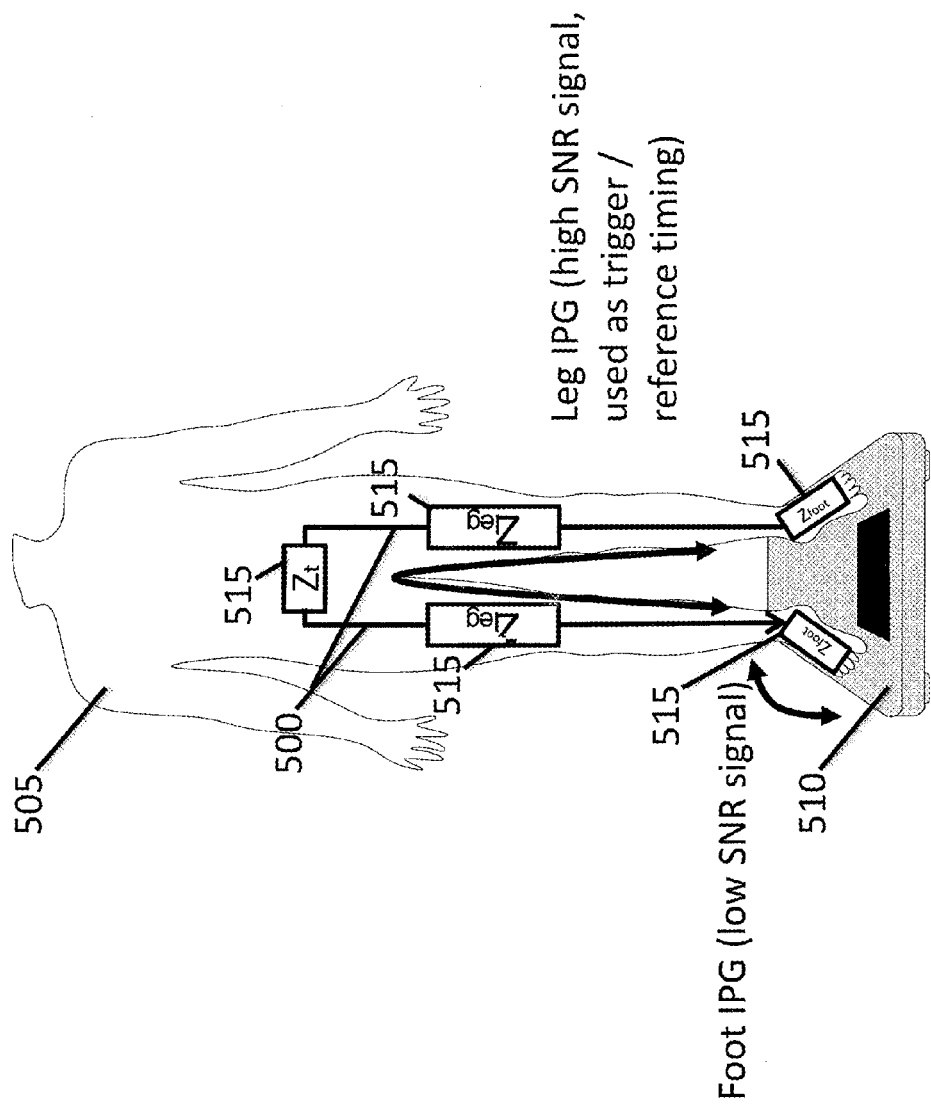

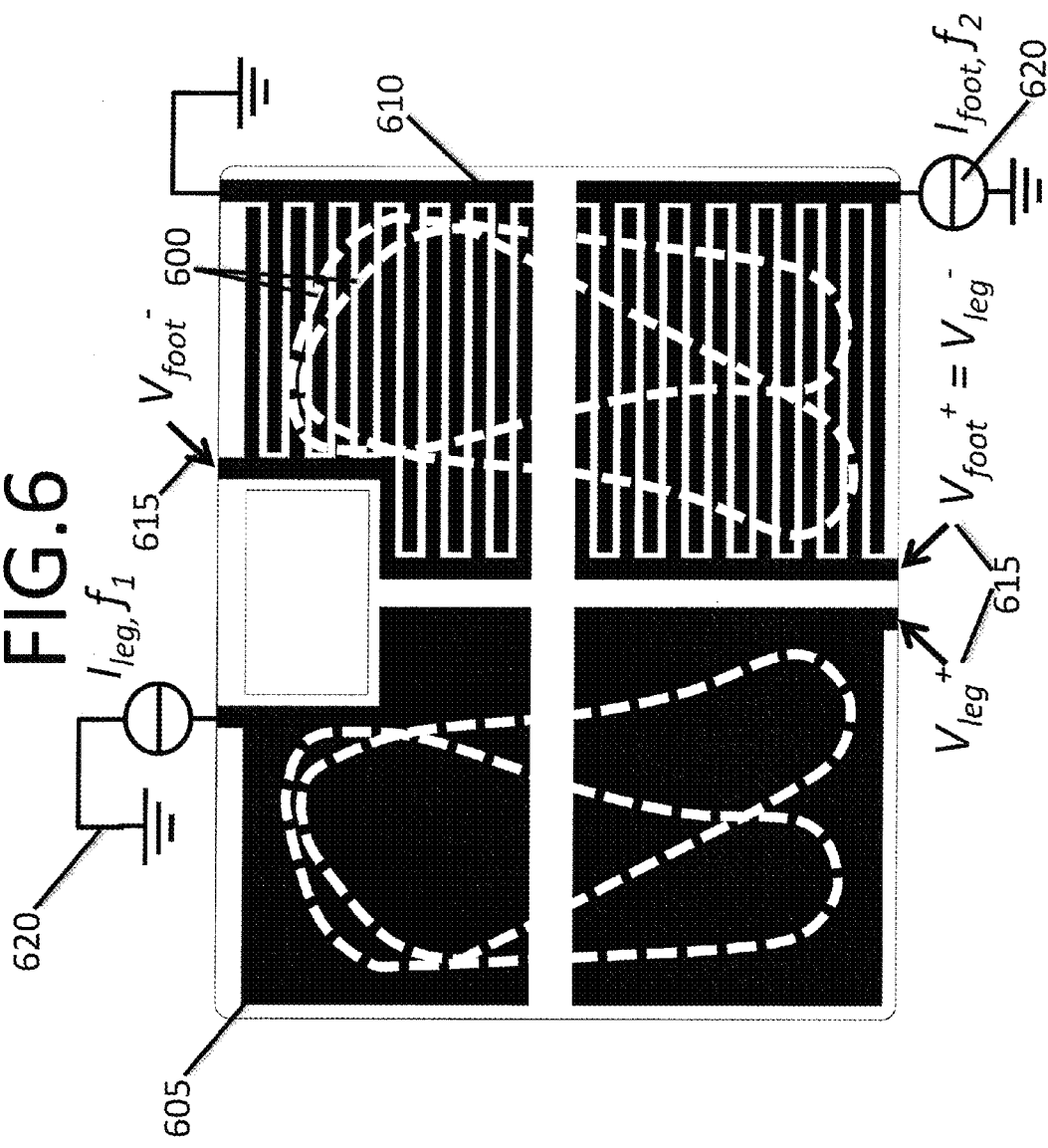

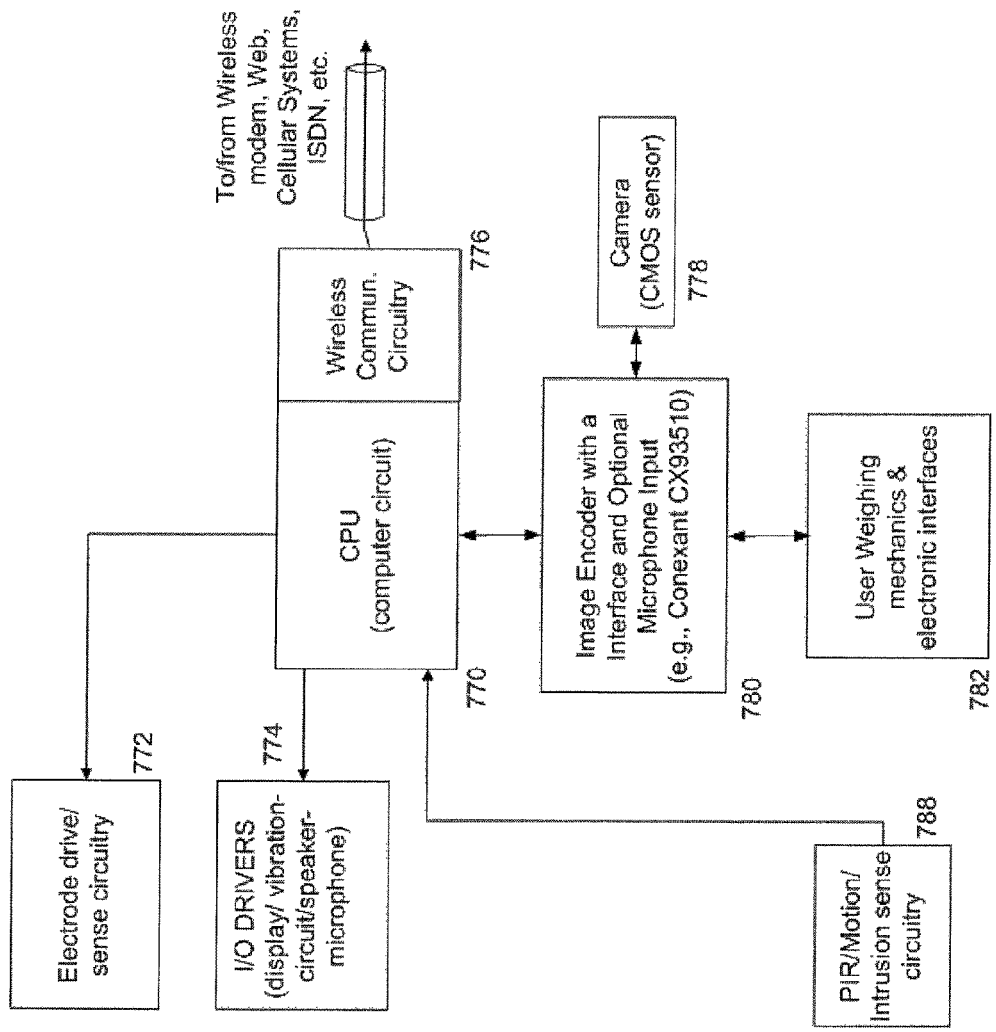

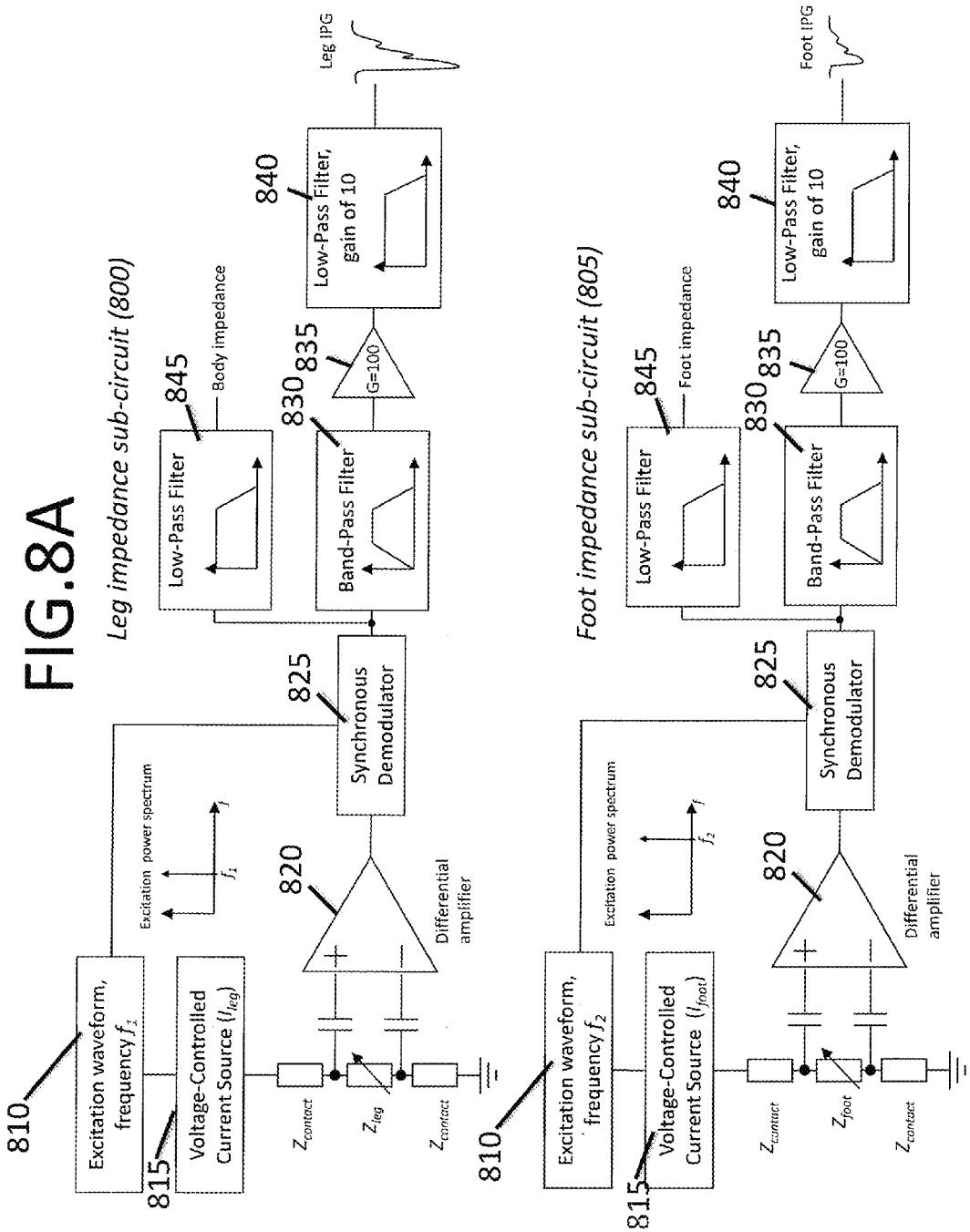

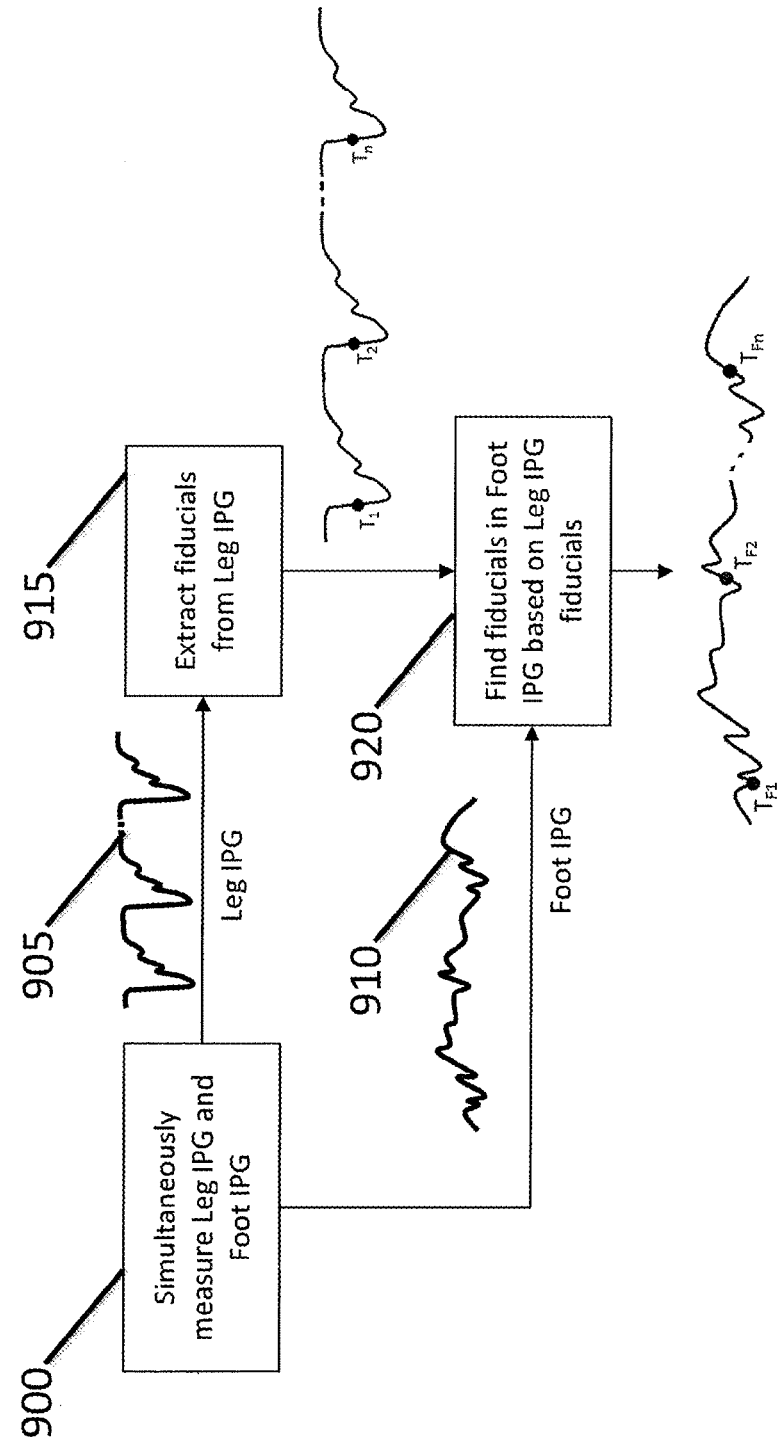

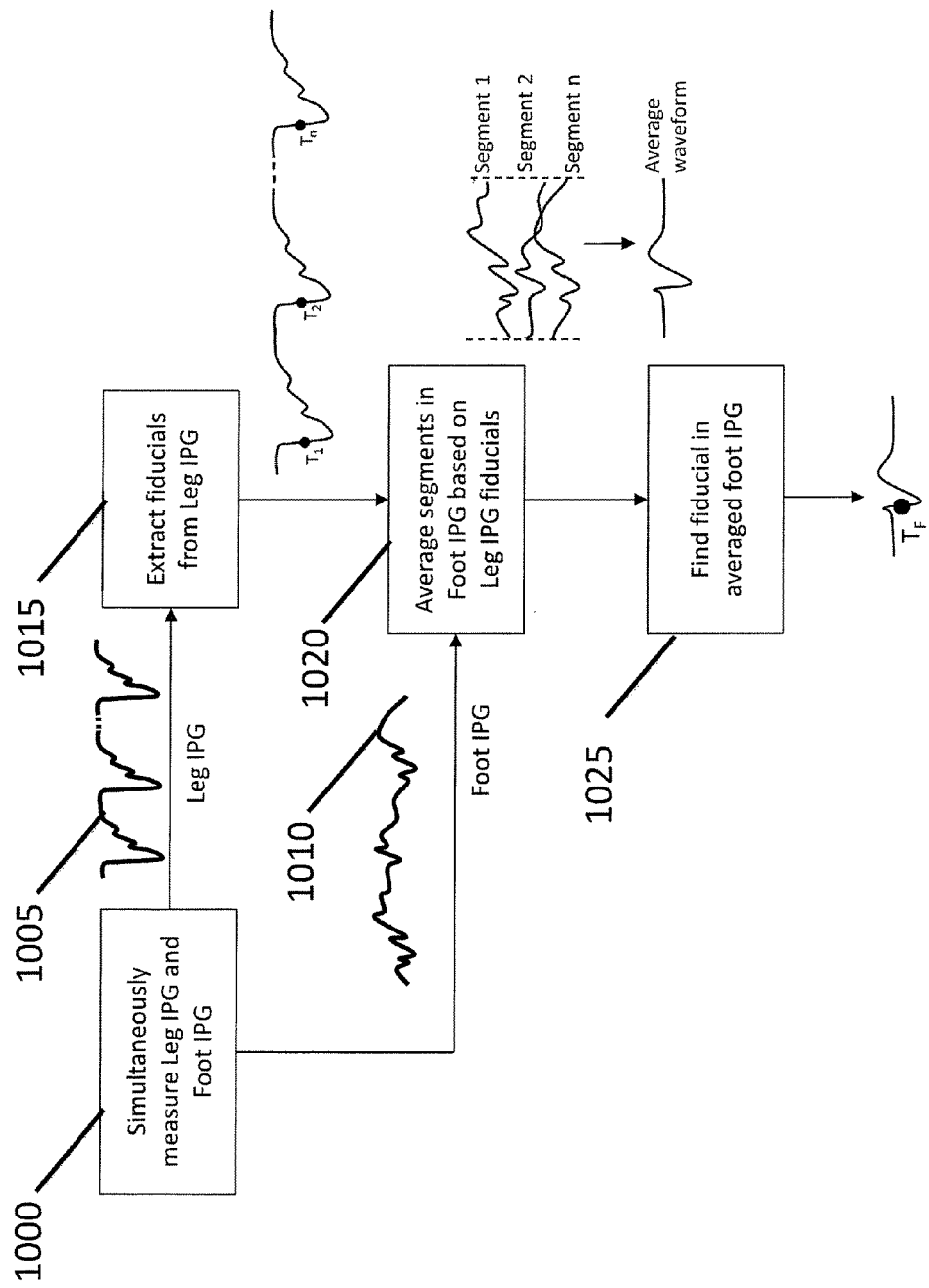

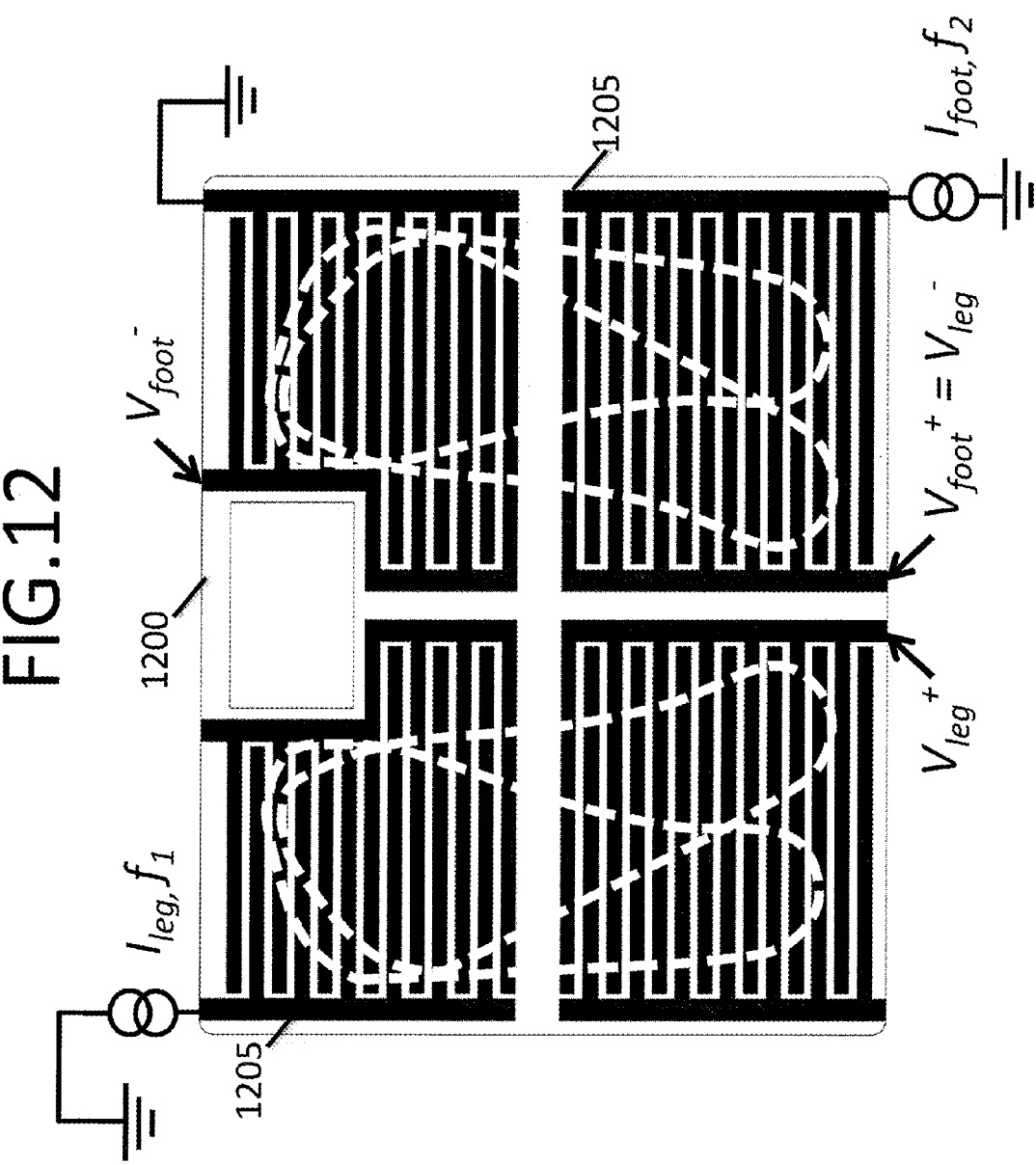

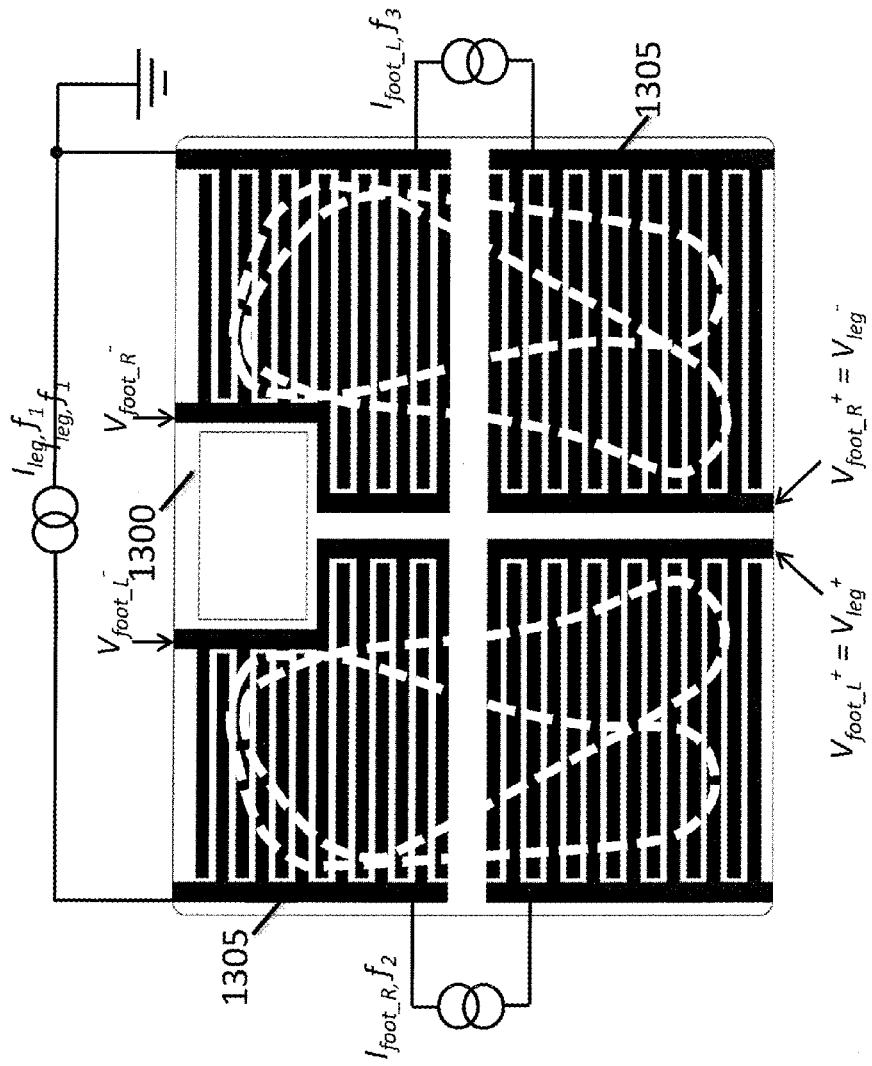

Transformer-coupled, grounded-load current source implementation

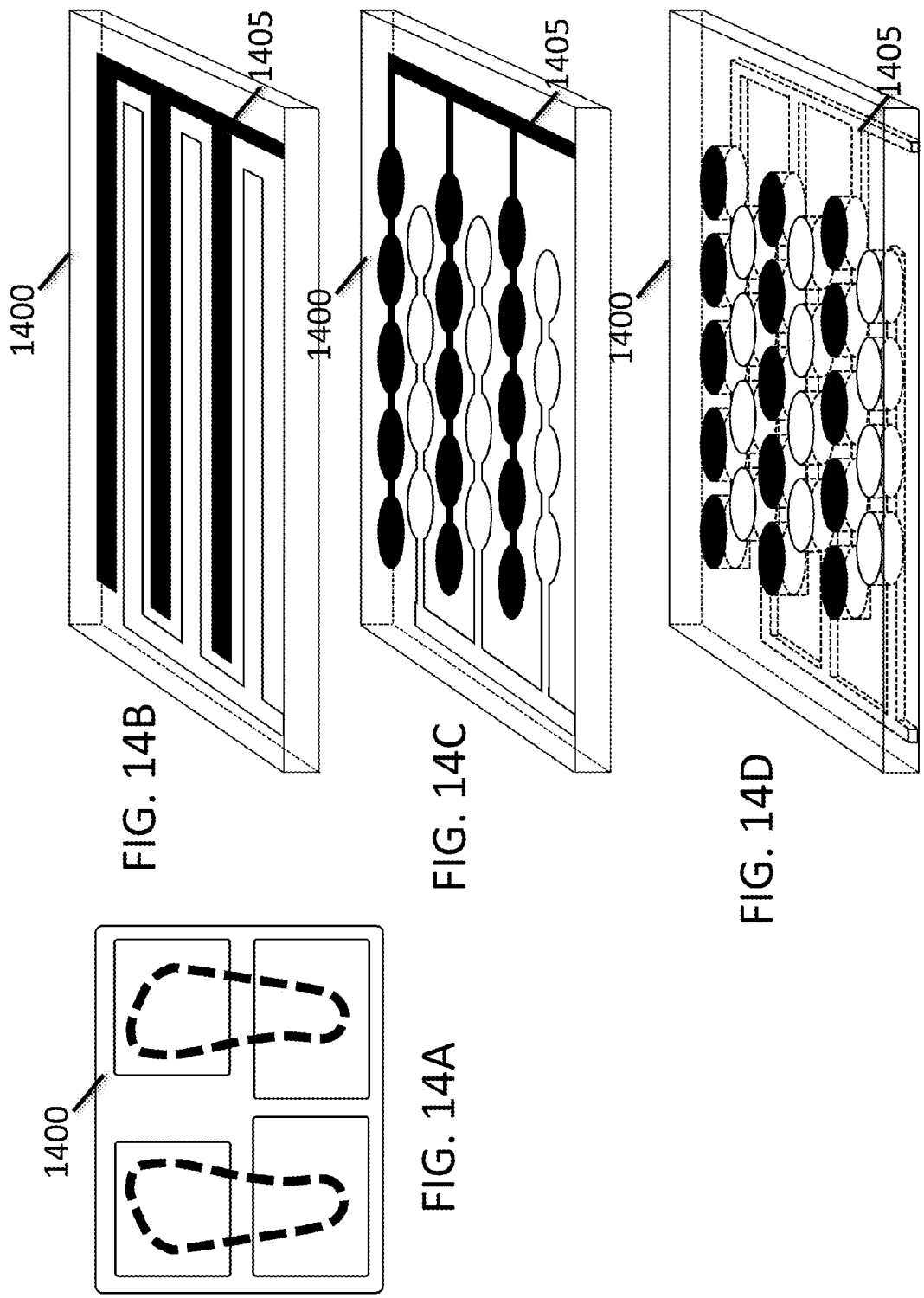

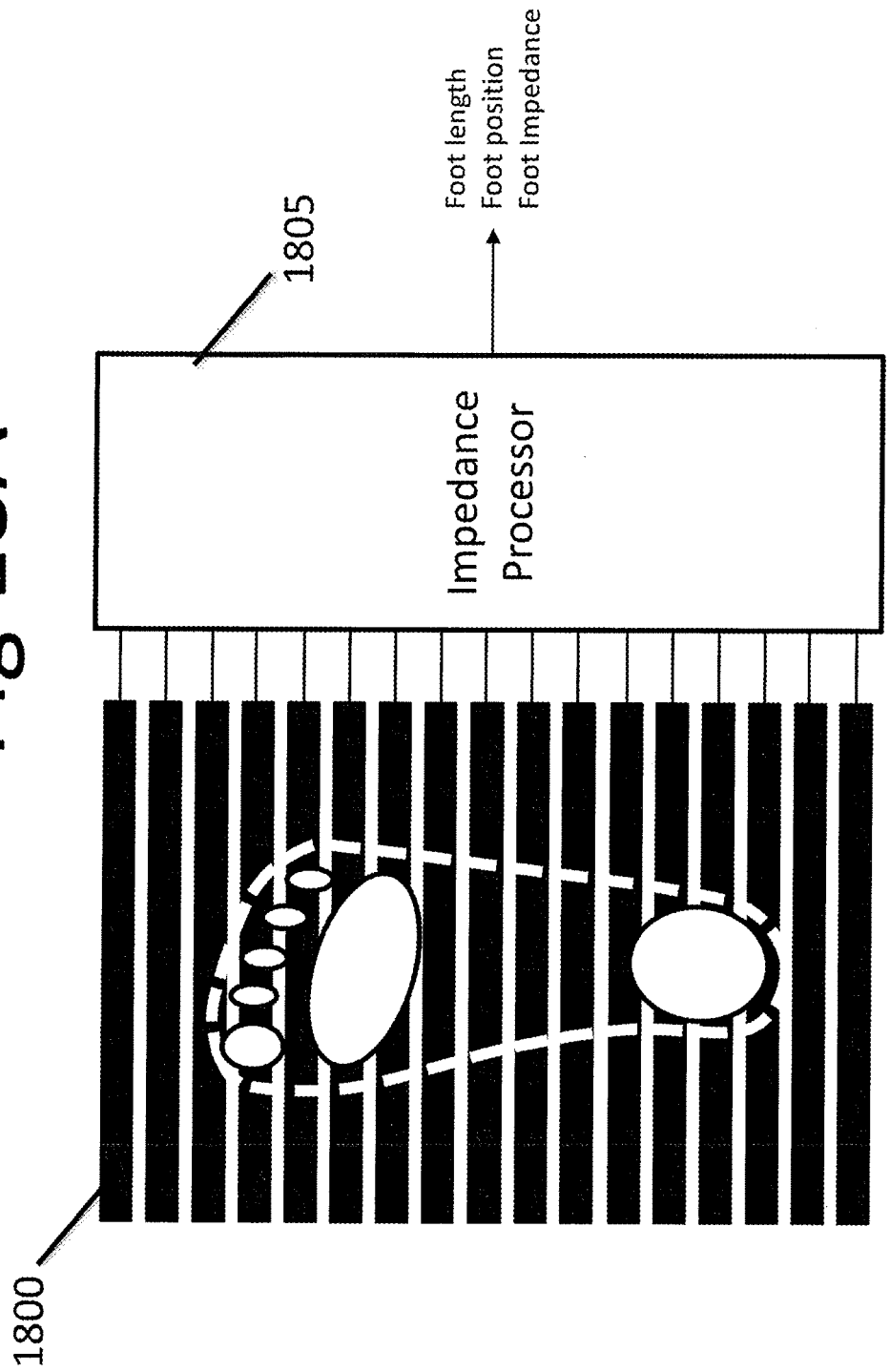

SYSTEM WITH USER-PHYSIOLOGICAL DATA UPDATES

RELATED PATENT DOCUMENTS

This patent document is a continuation under 35 U.S.C. §120 of U.S. patent application Ser. No. 14/618,623 filed on Feb. 10, 2015 (U.S. Pat. No. 9,498,137), which claims benefit under 35 U.S.C. §119(e) of U.S. Provisional Patent Application Ser. No. 62/034,582 filed on Aug. 7, 2014, and which includes three appendices (A through C); each of these patent documents is fully incorporated herein by reference in its entirety, as well as for the aspects specifically noted herein and for aspects readily recognized by the common disclosure and figures (e.g., the related teachings and discussion).

BACKGROUND

A variety of different physiological characteristics are monitored for many different applications. For instance, physiological monitoring instruments are often used to measure a number of patient vital signs, including blood oxygen level, body temperature, respiration rate and electrical activity for electrocardiogram (ECG) or electroencephalogram (EEG) measurements. For ECG measurements, a number of electrocardiograph leads may be connected to a patient's skin, and are used to obtain a signal from the patient.

Obtaining physiological signals can often require specialty equipment and intervention with medical professionals. For many applications, such requirements may be costly or burdensome. These and other matters have presented challenges to monitoring physiological characteristics.

SUMMARY

Various aspects of the present disclosure are directed toward a device and/or system that can be implemented to provide physiological data updates to a user. Various other aspects of the present disclosure are directed toward a user-support platform that can include and/or be implemented as a multi-function fitness scale and multisensory biometric weighing scale devices, systems and methods. Biometrics is a broad term wherein this application includes the measurements of body composition and cardiovascular information. Measurements (impedance based and otherwise) can be made through the feet to measure fat percentage, muscle mass percentage, and body water percentage. Additionally, cardiovascular measurements can be made for an electrocardiogram (ECG) and sensing the properties of blood pulsations in the arteries, also known as impedance plethysmography (IPG), where such techniques can be used to quantify heart rate and/or pulse arrival timings (PAT). Cardiovascular IPG measures the change in impedance through the corresponding arteries between the sensing electrode pair segments synchronous to each heartbeat.

Other aspects of the disclosure are directed to a user platform apparatus, such as a weighing (e.g., bathroom) scale specifically designed for monitoring and improvement, through feedback it provides to the user, of fitness. The scale is equipped to monitor some or all of the following measurements: weight (e.g., bodyweight), body composition, hydration level, ballistocardiogram (BCG), impedance cardiogram (ICG), electrocardiogram (ECG), pulse wave velocity (PWV), photoplethysmogram (PPG) (or others) and from these provide both an instantaneous assessment of fitness as well as feedback for improvement. One aspect of this system is directed to measuring physiological parameters in a resting state (e.g., after the user wakes up in the morning and while standing on the scale) and relative to a coached state of exertion. From the latter state, the system (e.g., platform apparatus) can monitor the user's physiological recovery to baseline, and the apparatus can estimate the user's level of cardiovascular fitness. Repeating such measurements over time can be used to provide trending and feedback for improvement.

A specific example embodiment is directed to an apparatus comprising a user wearable device and a weighing scale. The user wearable device includes a signal communication circuitry and output circuitry configured and arranged to communicate selected data to a user and to provide monitored selected data indicative of physiological parameters. The weighing scale includes a platform region configured and arranged with an area for the user to stand, user-targeted circuitry configured and arranged to communicate user-specific data between the user and the user-targeted circuitry, and a base unit. The base unit is configured and arranged to integrate a support structure and a display. The support structure includes the platform region and sensor circuitry including current-impedance electrodes (herein generally referred to as "electrodes" for ease of reference). The sensor circuitry is configured and arranged to obtain a plurality of impedance-measurement signals via the current-impedance electrodes and to determine physiological signals of the user using the plurality of impedance-measurement signals. The platform region configured and arranged to engage the user with the sensor circuitry while the user stands on the platform region, and to collect physiological data from the user via the sensor circuitry. The display is configured and arranged with the support structure for displaying data through the platform region for view by the user while the user stands on the platform region. Further, the display configured and arranged with the user-targeted circuitry to monitor a plurality of physiological signals of the user while the user is standing on the platform region, and select data indicative of a physiological parameter of the user, for display on one of the user wearable device and the display of the weighing scale, based on a threshold value and the plurality of physiological signals.

In another specific example embodiment, the user wearable device includes circuitry configured and arranged to monitor selected data indicative of physiological parameters, and signal communication circuitry and output circuitry configured and arranged to communicate the selected data to the weighing scale. In such embodiments, the weighing scale comprises a communication circuitry configured and arranged with a display of the weighing scale to receive the data indicative of the physiological parameters from the communication circuitry of the user wearable device, a platform region configured and arranged with an area for the user to stand, user-targeted circuitry configured and arranged to communicate user-specific data between the user and the user-targeted circuitry, and a base unit. The base unit is configured and arranged to integrate a support structure including the platform region and sensor circuitry therein. The sensor circuitry includes current-impedance electrodes configured and arranged to contact the user, and is configured and arranged to obtain a plurality of impedance-measurement signals via the current-impedance electrodes and to determine physiological signals of the user using the plurality of impedance-measurement signals. The platform region is configured and arranged to engage the user with the sensor circuitry while the user stands on the platform region, and to collect physiological data from the user via the sensor circuitry, and the display configured and arranged with the support structure for displaying data through the platform region for view by the user while the user stands on the platform region, configured and arranged with the user-targeted circuitry to: monitor a plurality of physiological signals of the user while the user is standing on the platform region, and select data indicative of a physiological parameter of the user, for display on one of the user wearable device and the display of the weighing scale, based on a threshold value and at least one of the plurality of physiological signals and the data indicative of the physiological parameters received from the user wearable device.

A specific example embodiment is directed to an apparatus comprising a platform region configured and arranged to support a user while the user stands on the platform region. The apparatus includes user-targeted circuitry and a base unit. The base unit is configured and arranged to integrate a support structure and a display. The support structure includes the platform region and sensor circuitry therein. The platform region is configured and arranged to engage the user with the sensor circuitry while the user stands on the platform region, and to collect physiological data from the user via the sensor circuitry. The display is configured and arranged with the support structure for displaying data through the platform region and is configured and arranged with the user-targeted circuitry to: monitor physiological parameters while the user is standing on the platform region, and communicate assessed fitness to the user as feedback, wherein the assessed fitness is based on one or more of the physiological parameters.

Another example apparatus includes a platform structure for supporting a user while the user stands on the platform structure, user-targeted circuitry, and a base structure. The base structure includes a housing to provide support for the person standing on the apparatus and for integrating with a support structure, a display structure, and a communication circuitry. The support structure includes a support frame, the platform structure, and the sensory circuitry. The platform structure includes a frame and sensor circuitry to engage the user with the sensor circuitry while the user stands on the platform structure, and for collecting physiological data from the user via the sensor circuitry. The display structure, including a display device, is arranged with the support structure for displaying data through the platform structure. Further, the display structure is configured and arranged with the user-targeted circuitry to: monitor physiological parameters of the user over a period of time, and assess a fitness of the user based on one or more of the physiological parameters. The communication circuitry, including a communication driver, provides information from the user-targeted circuitry to the display structure of the apparatus for viewing by the user through the platform structure. The information, in some embodiments, includes the assessed fitness.

The physiological parameters, in some embodiments, include recovery parameters. Recovery parameters are measured by the apparatus measuring physiological parameters while the user is standing on the platform structure in a resting state, and the apparatus instructing the user to enter an exertion state in response to the measured physiological parameters. Further, the apparatus measures physiological parameters while the user is standing on the platform structure in the exertion state. The apparatus measures physiological parameters, in various embodiments, in response to the platform structure engaging with the sensor circuitry. A recovery parameter is determined, by the apparatus, based on the physiological parameters in the resting state and the exertion state.

One specific example embodiment of the present disclosure may be implemented in accordance with the following operational flow. The user steps on the platform apparatus (e.g., scale) in a resting state and the scale measures (for example) bodyweight, body composition, BCG, PWV and/or heart rate. The display on the scale, or via an application on a user's connected mobile device (e.g., phone, tablet, laptop) then, or at a later time, coaches the user to take a fitness test. This test can involve going for a run outdoors, working out on an exercise machine (elliptical, treadmill, etc.) or doing some defined exercises to raise the heart rate (running on the spot, etc.). The user then steps on the scale, which first verifies that the heart rate was sufficiently above the previously measured resting rate to allow for meaningful measurements. If the heart rate is too low, the scale coaches the user to do additional exercise to raise their heart rate prior to repeating the measurements. Once this condition is met, the user is instructed, by the scale, to stay on the scale for one or more minutes, over which the measurement of BCG, PWV, heart rate and/or other parameters are carried out regularly and periodically until sufficient data is collected to allow computation of the changes due to exercise and importantly the rate that these parameters (or derivatives thereof) return toward baseline (although it will not typically be necessary to wait until the actual baseline range is reached). Collectively or individually, a "recovery rate" or time constant are calculated that indicate the relative level of fitness of the user's cardiovascular system (quicker return to baseline generally indicates a high level of fitness).

Over time, these recovery parameters, in concert with the other parameters measured, in accordance with some embodiments, are presented to the user to provide feedback for improving or maintaining their level of fitness. Through the use of coupled applications on a mobile device, computer or in the cloud, the user tracks their exercise history, for example, to allow correlations such as noting that extra aerobic exercise beyond their habitual amount does, or does not, produce noticeable benefits in terms of fitness. In addition, in a number of embodiments, these coupled applications import data such as heart rate, speed, altitude change and others which are gathered from wearable monitors (such as heart-rate straps or watches, accelerometers, mobile device, Global Positioning System (GPS) trackers, etc.) to further refine their measurements and feedback. But, a key aspect of the system is that fitness feedback is provided to a user without any of these sensors, devices or activities, in the minimum simply coaching the user to exercise, then measuring the changes and recovery in their measured physiological parameters.

As another optional aspect, the scale recognizes the user (e.g., via facial or foot recognition during a power start-up mode) and, based on a stored profile for the user, access the user's preferred coaching data. This stored coaching data changes over time based on the user's performance, heart rate, weight improvements, age, fitness, medical conditions (most all of which can be automatically retrieved or measured) and/or other criteria which the user inputs manually.

In some embodiments, a fitness of a user is assessed. For example, a fitness of a user is be assessed by monitoring physiological parameters of a user using an apparatus, the apparatus including circuitry configured and arranged to engage with the user and measure the physiological parameters. The physiological parameters include at least one of the group selected from: user weight (e.g., bodyweight), body composition, hydration level, ballistocardiogram (BCG), impedance cardiogram (ICG), electrocardiogram (ECG), pulse wave velocity (PWV), and photoplethysmogram (PPG). A fitness of the user is assessed based on one or more of the physiological parameters and the assessed fitness is communicated back to the user as feedback using the circuitry of the apparatus. The feedback to the user, in various embodiments, includes coaching, e.g., suggestions, to the user regarding fitness, health, dietary consideration, etc., based on the assessed fitness, physiological parameters, and/or other indicators.

This description is intended to be illustrative of one of many possible embodiments of the invention and not to be limiting. Various example embodiments may be more completely understood in consideration of the following detailed description in connection with the accompanying table, in which:

Table 1 is a chart showing category of users along the vertical axis and indications of one or more scale-provided physiological indication/measurements (e.g., pulse wave velocity ("PWV")) with an explanation of the physiological measurement(s) and, relating thereto, possible-action recommendation(s) along the horizontal axis. For example, the third row in the chart shows a category of users classified as fitness oriented, quantified self and in the age group of 25 to 40 years old ("25-40 y/o"). The term "red/yellow" zone (corresponding to traffic light warnings) indicates the healthiness of the charted physiological indication (green is safe to continue, yellow indicates to proceed with some degree of caution, and red is a recommendation to stop). The other related explanations are self-explanatory.

DESCRIPTION OF THE FIGURES

Various example embodiments may be more completely understood in consideration of this detailed description and in connection with the accompanying drawings, in which:

FIG. 1C shows an example apparatus comprising a platform region, user-targeted circuitry, and a base unit, consistent with various aspects of the present disclosure;

FIG. 5B shows current paths through the body for the IPG trigger pulse and Foot IPG, consistent with various aspects of the present disclosure;

FIG. 6 shows an example of the insensitivity to foot placement on scale electrodes with multiple excitation and sensing current paths, consistent with various aspects of the present disclosure;

TABLE 1

| | PWV | Meaning | Actions to be taken |
|---|---|---|---|
| Elderly (over 65) | Red Zone (>12 m/s) | Deviation from a healthy population and should be investigated | Investigate overall cardiovascular heatth (blood pressure, other possible tests depending on symptoms) Adjust exercise and diet Adjust medication with the aid of a physician |
| | Unfavorable trend - rapid (10-12 m/s & > +1 m/s change) | Condition deteriorating rapidly | Investigate causes: examples may include not taking medication, deteriorating heart or vascular condition |
| | Unfavorable trend slow (10-12 m/s & +0.5 m/s change) | Condition deteriorating slowly | Investigate causes: examples of actions include optimize medication (typical hypertensive patient on 3 medications), dietary changes, exercise changes |
| | Green zone (<10 m/s) | Normal arterial health | Maintain a healthy lifestyle |
| Worried, middle-aged (40-65 y/o) | Red/Yellow Zone (Age-dependant PWV) | Deviation from a healthy population and should be investigated | Consult physician but PWV and steps that can be taken to improve overall health. Possible actions include prescribing, a statin that has been shown to improve PWV, and changing diet and exercise habits |
| | Unfavorable trend Green zone | Accelerated arterial, aging Normal arterial health | Increase exercise and changes in diet Maintain a healthy lifestyle |
| Fitness oriented, quantified self (25-40 y/o) | Red/yellow zone | Deviation from a healthy population and should be investigated | Unlikely to be seen in this demographic, and should be cause for further investigation if found. May indicate excessive strength training. |
| | Favorable trend in green zone | Improving arterial stiffness | Indicates effective cardiovascular exercise regime |
| | Unfavorable trend in green zone | Increased arterial stiffness | May indicate less effective cardiovascular training, or increased strength training |

Figure 7B:
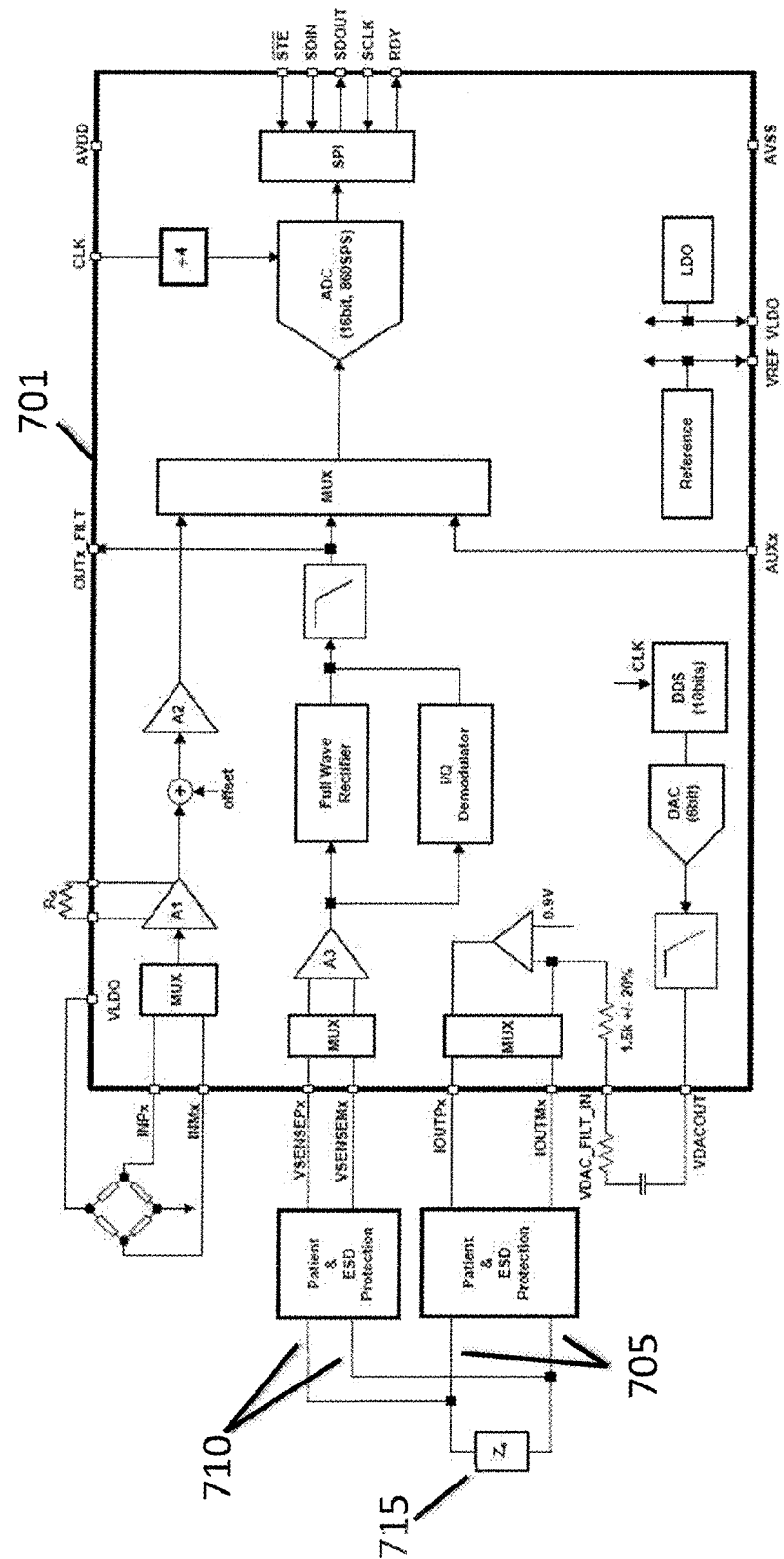
FIG. 7A depicts an example block diagram of circuitry for operating core circuits and modules, including, for example, those of FIGS. 8A-8B, used in various specific embodiments of the present disclosure.

FIG. 7B shows an exemplary block diagram depicting the circuitry for interpreting signals received from electrodes.

Figure 8B:
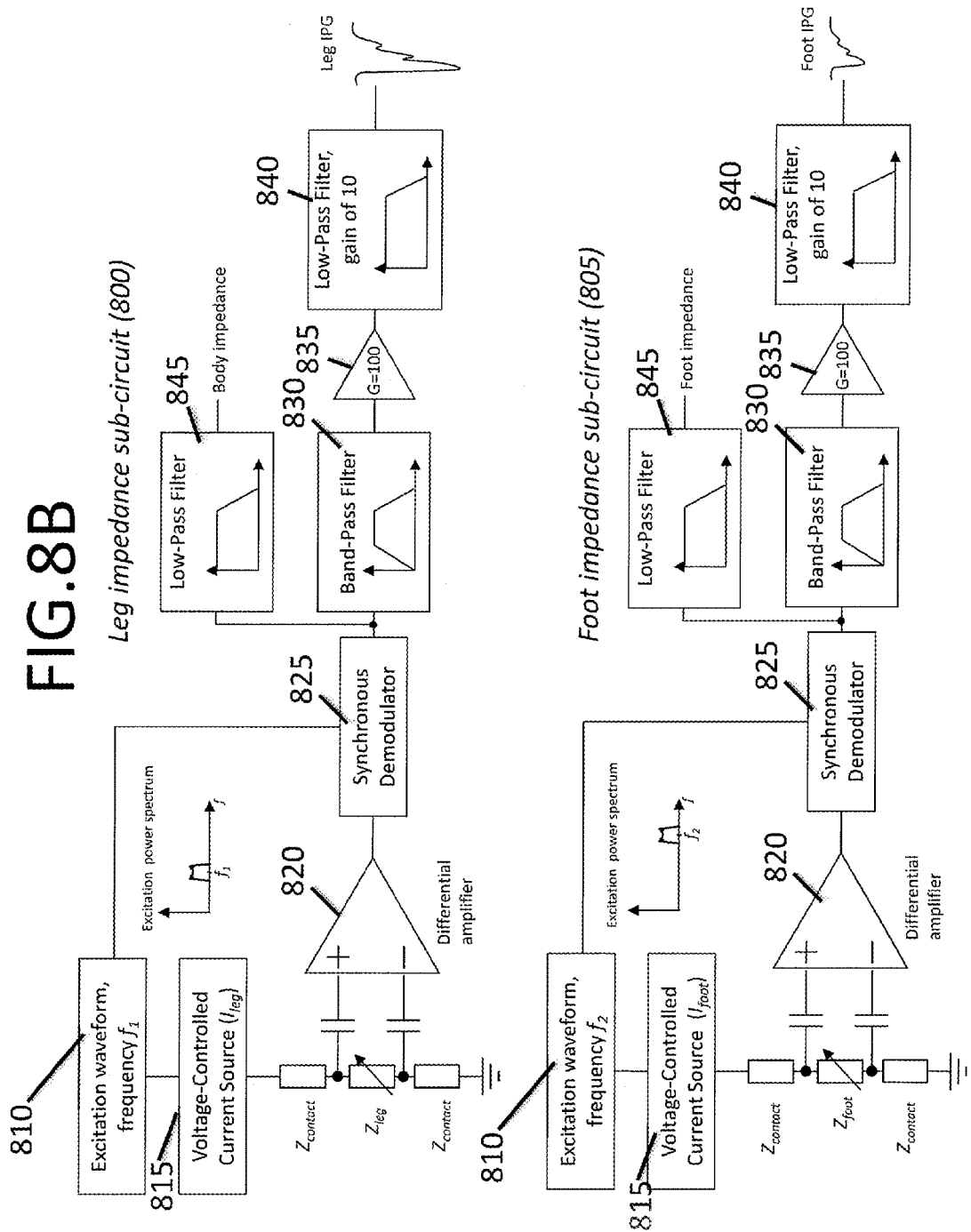
Figure 11:
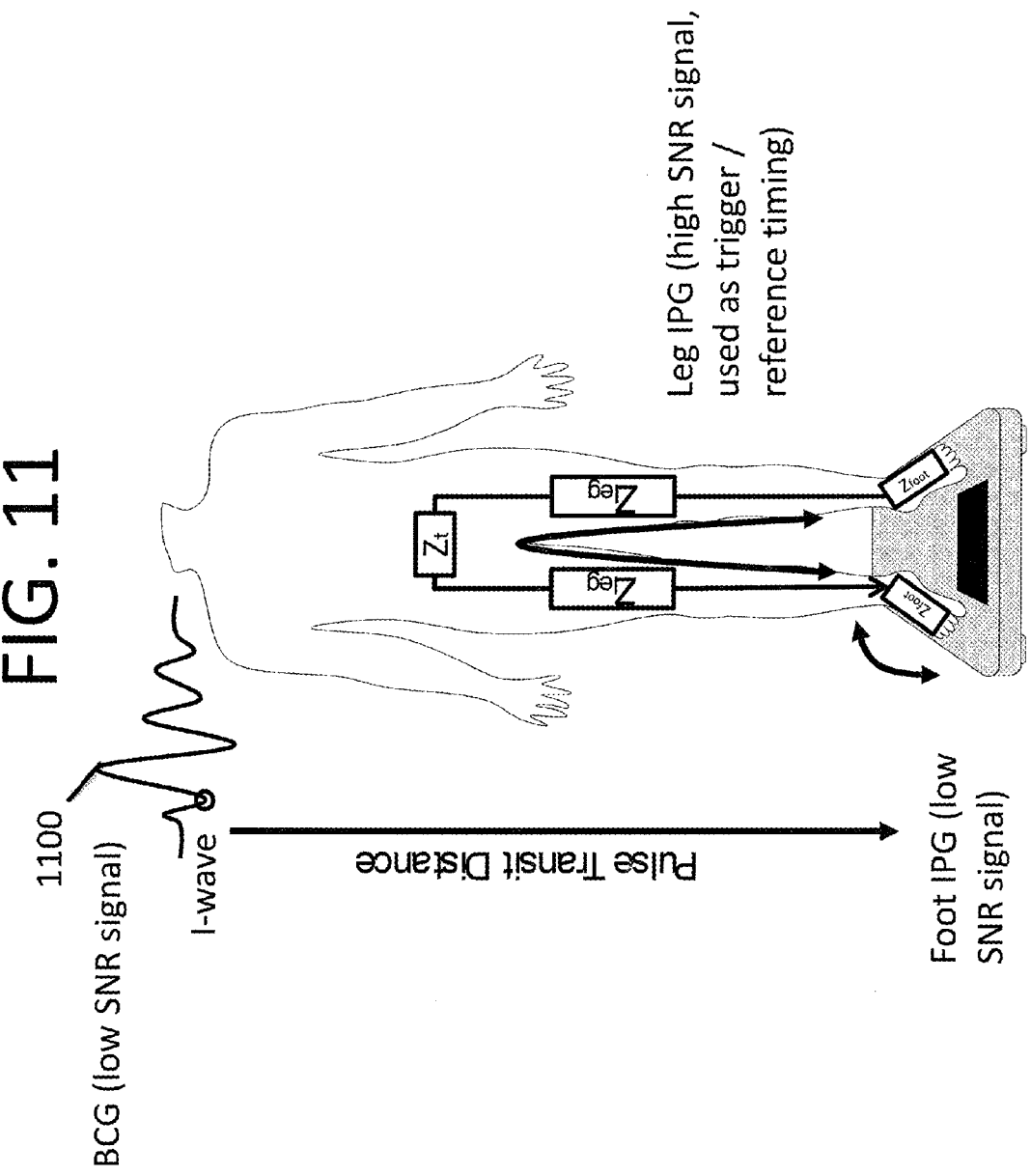
Figure 13A:
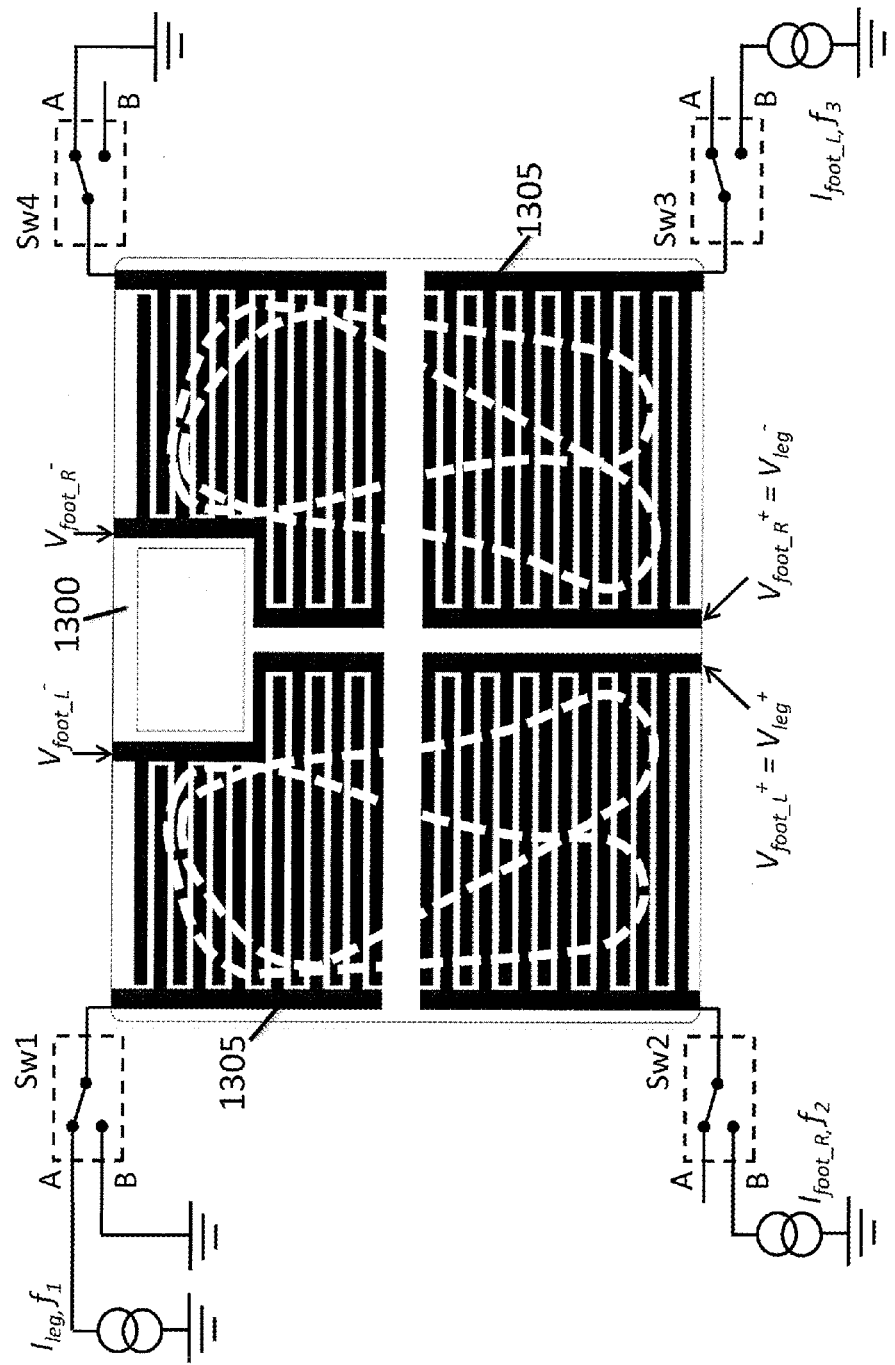
Figure 13C:
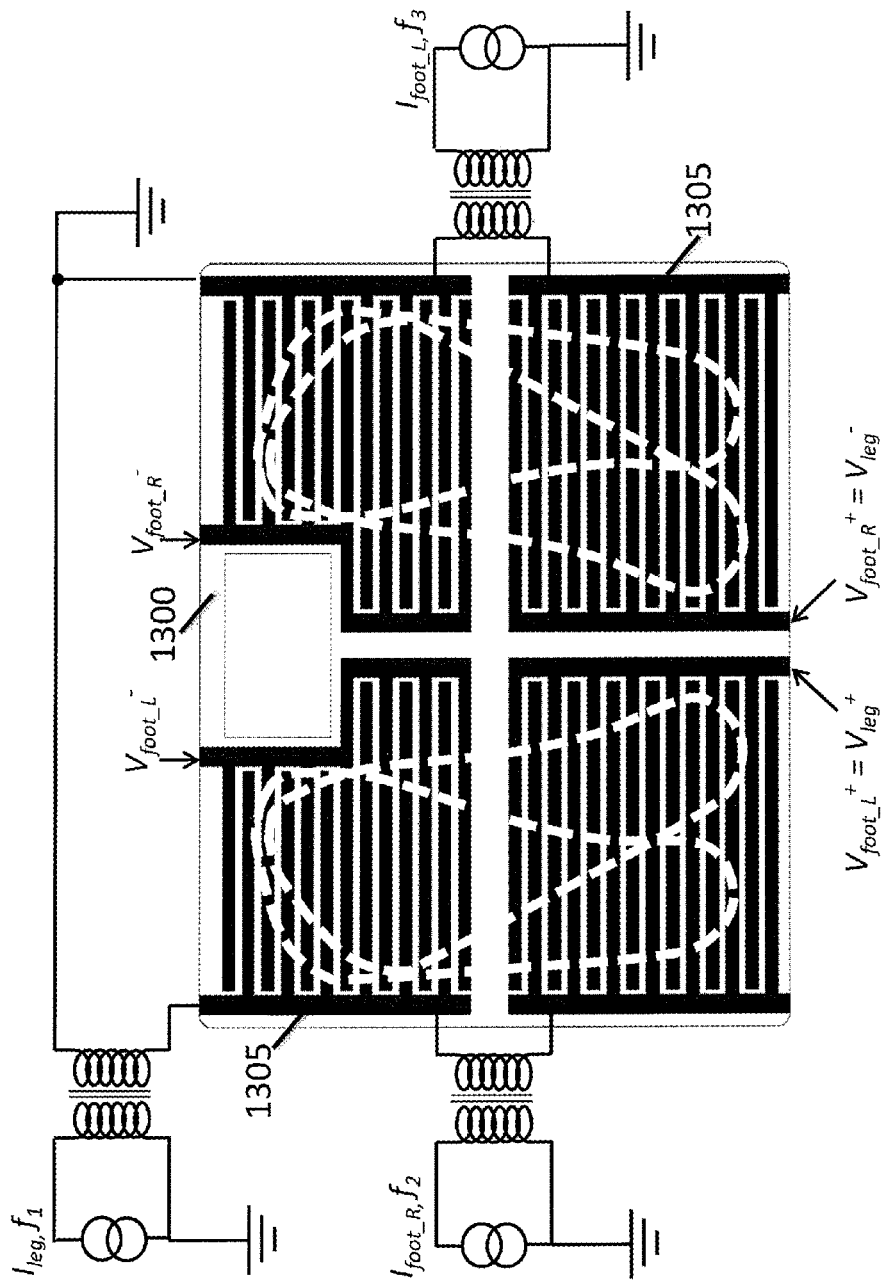
Figure 15:
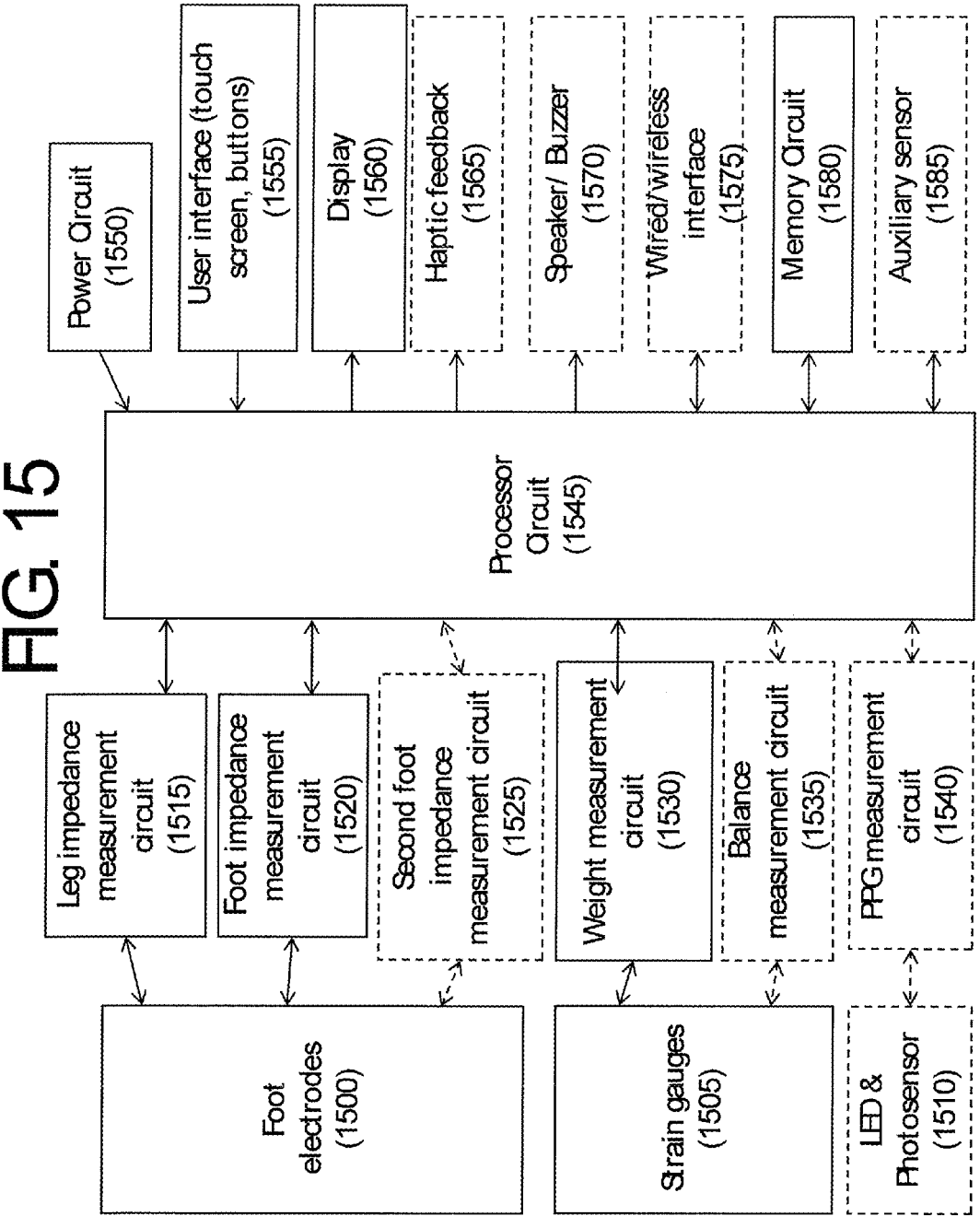
Figure 16:
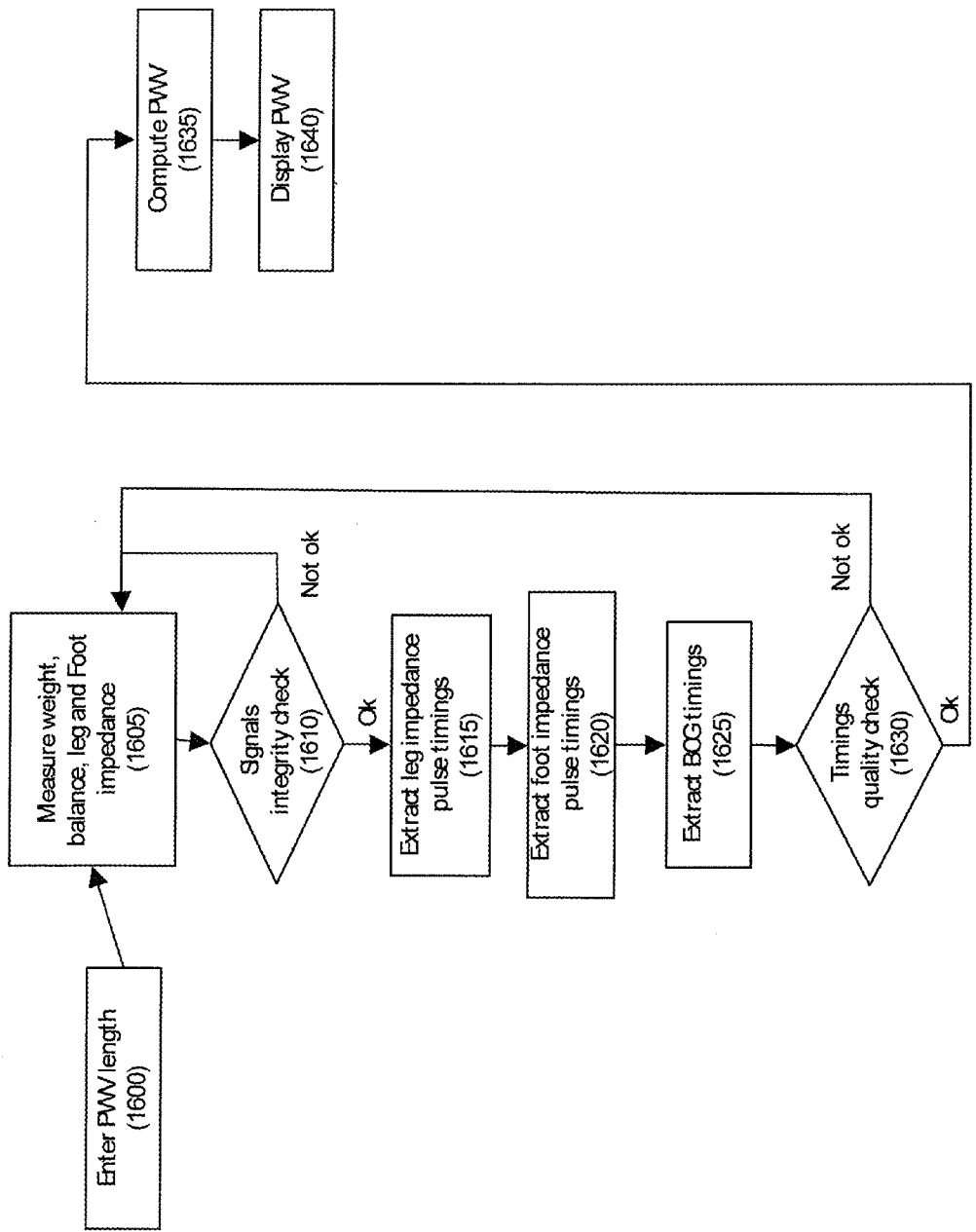
Figure 17:
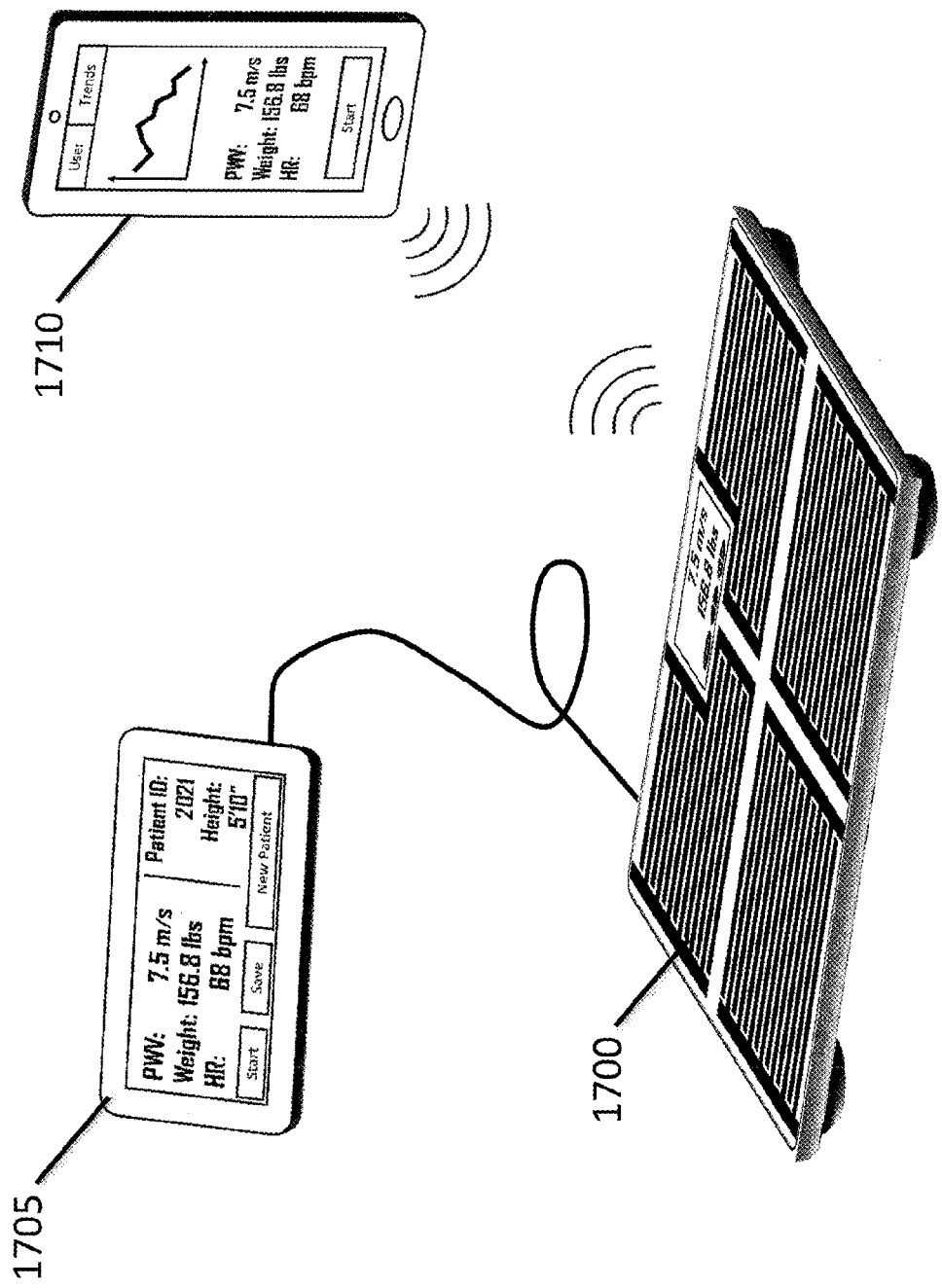
Figure 18B:
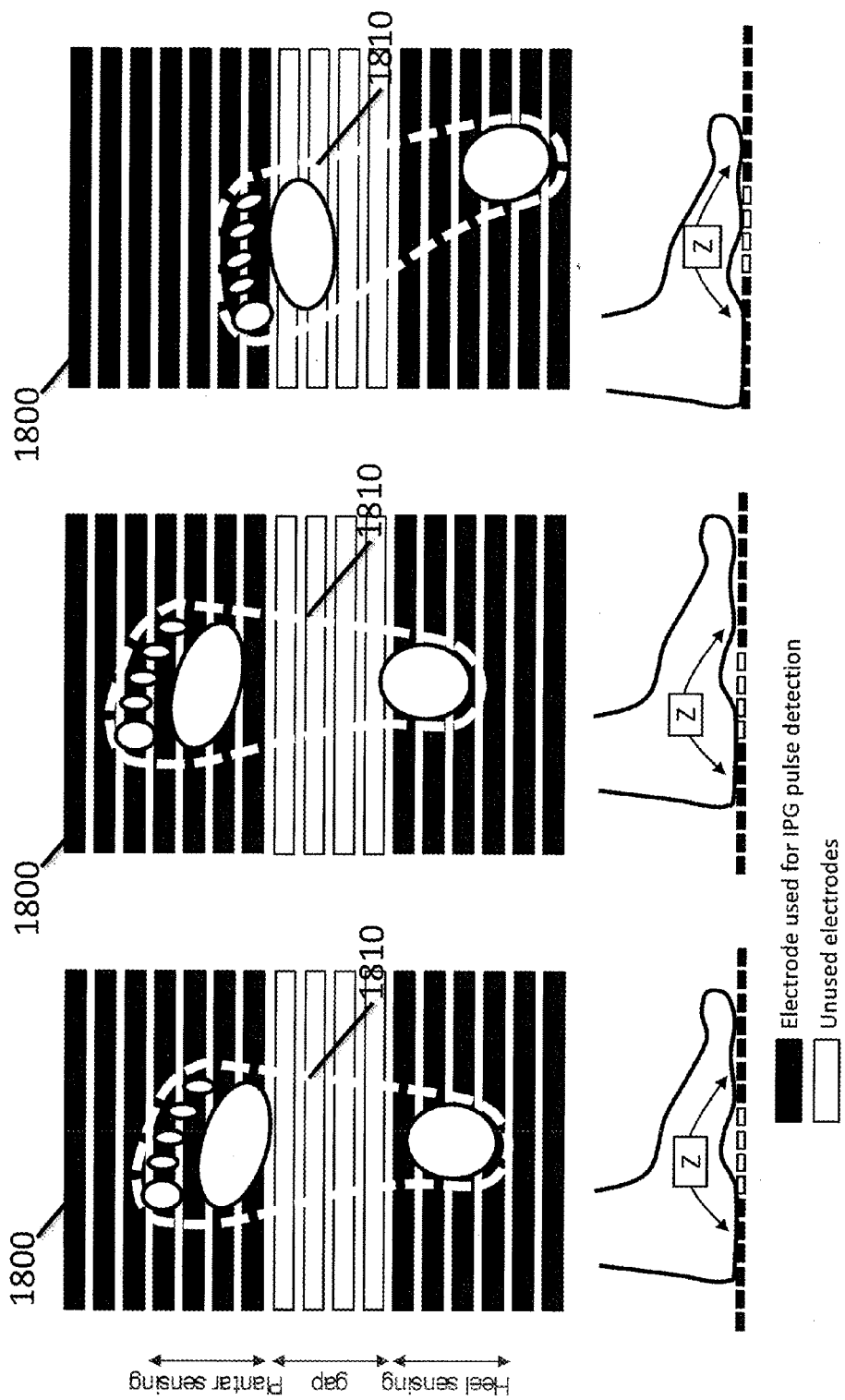
Figure 18C:
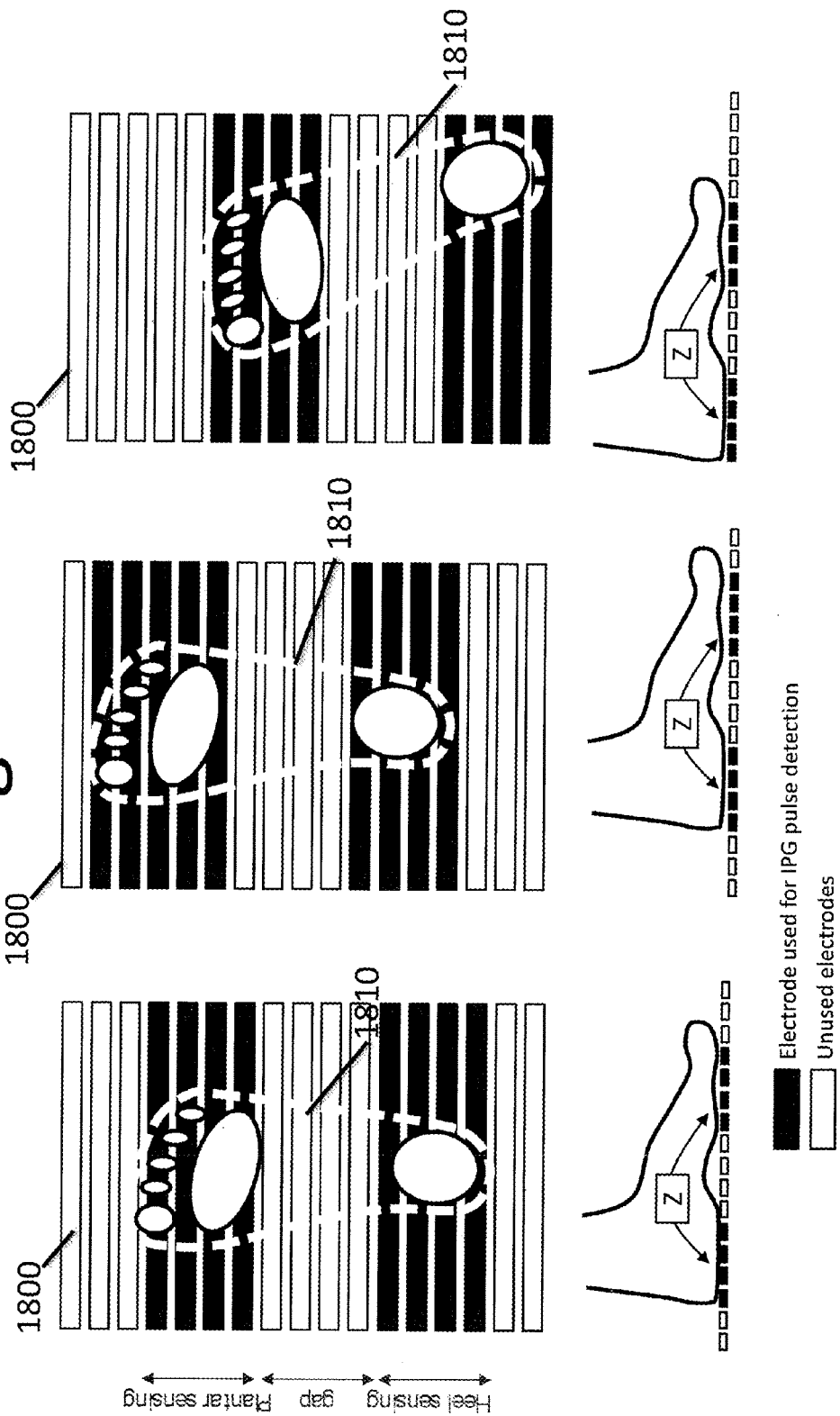
Figure 19:
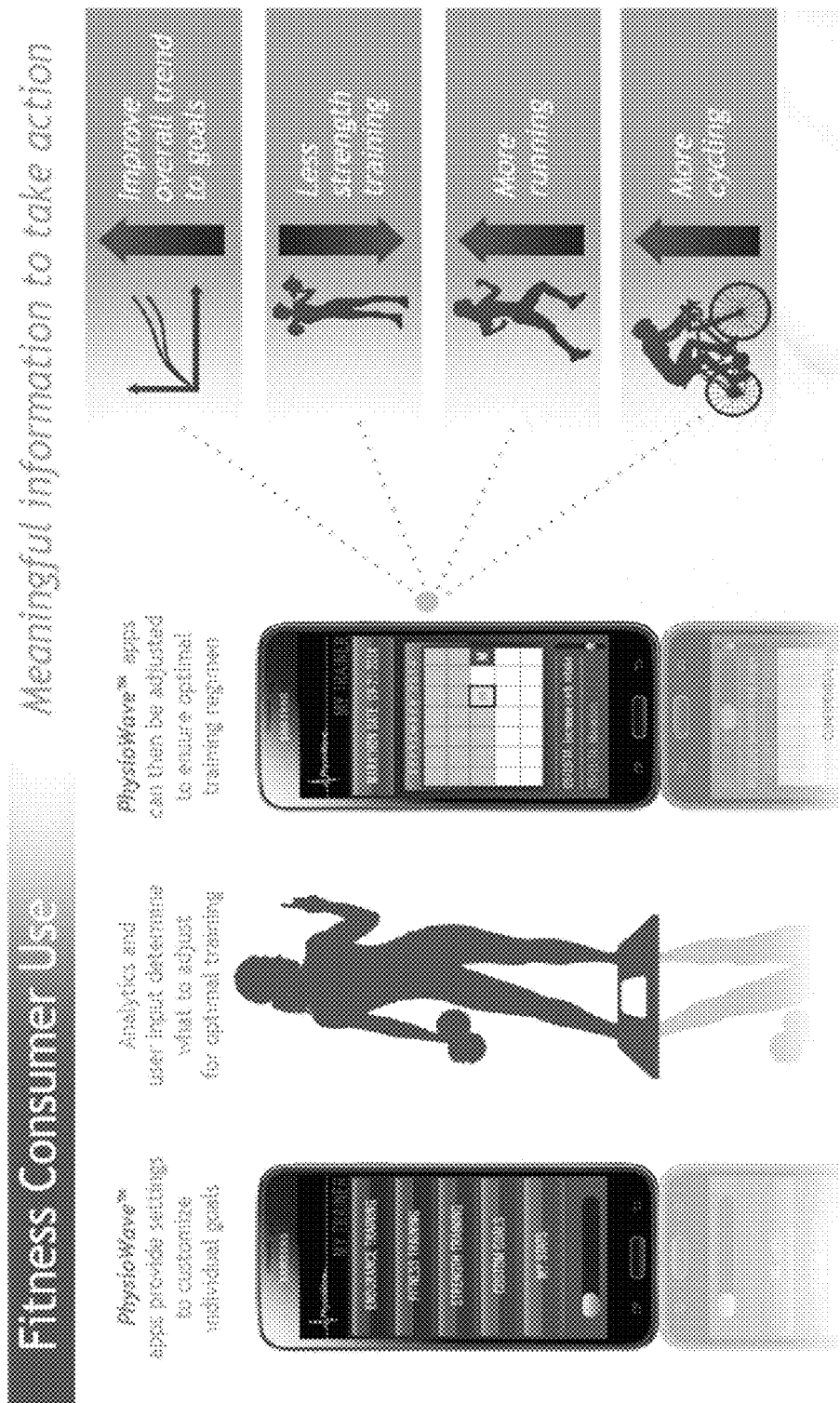
Figure 20:
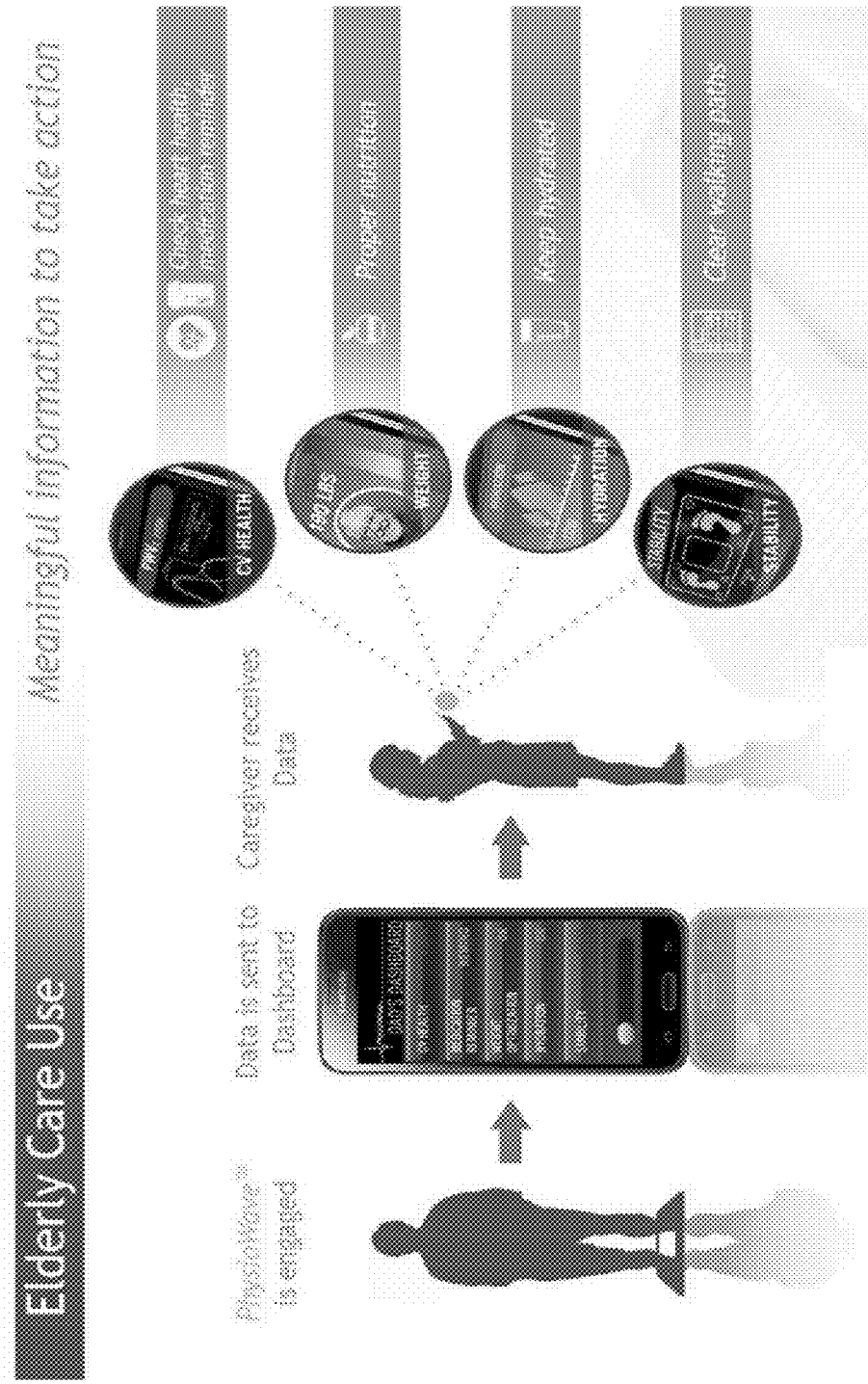
Figure 21:
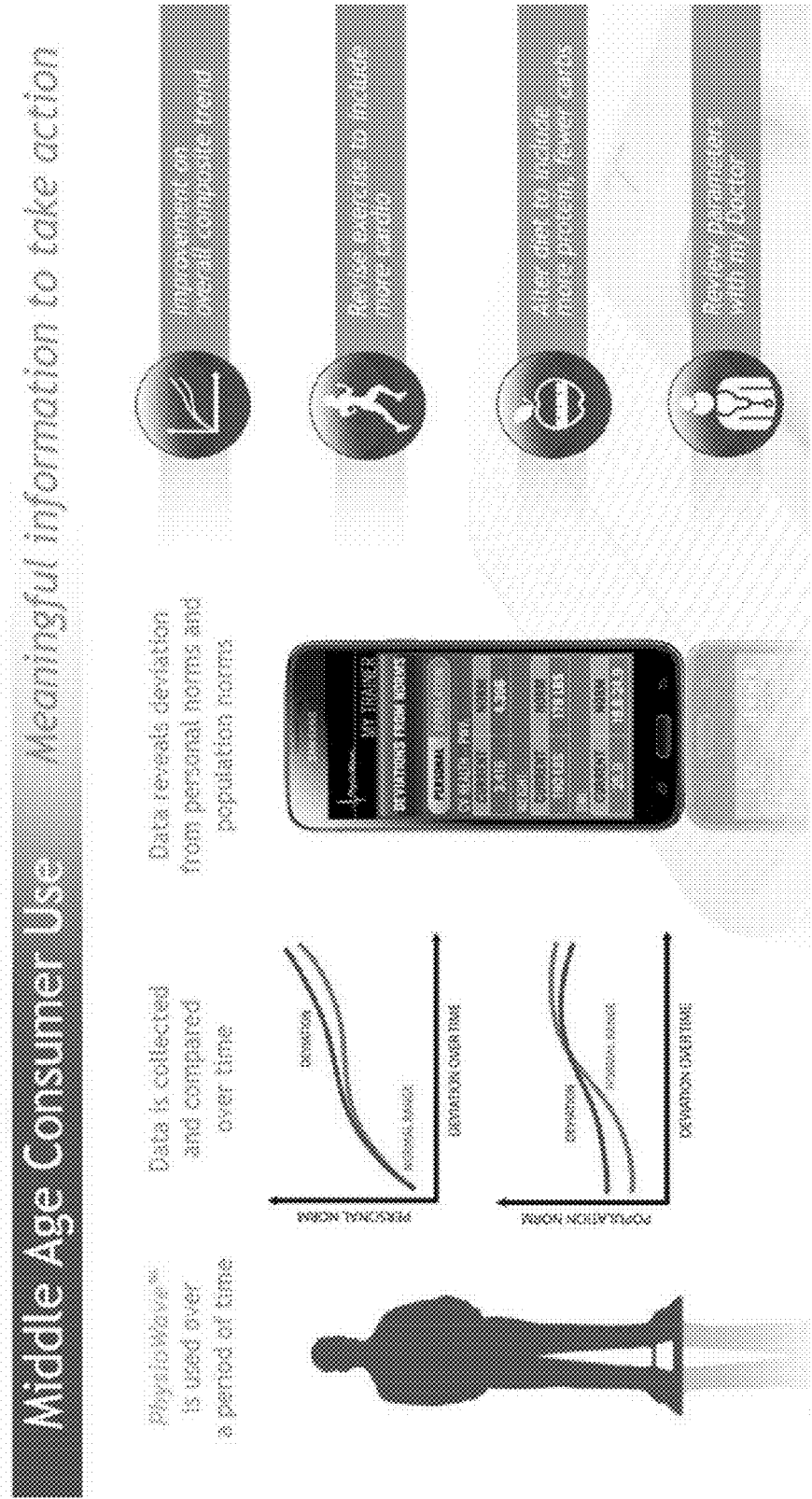

FIGS. 8A-8B show example block diagrams depicting the circuitry for sensing and measuring the cardiovascular time-varying IPG raw signals and steps to obtain a filtered IPG waveform, consistent with various aspects of the present disclosure;

FIG. 9 shows an example block diagram depicting signal processing steps to obtain fiducial references from the individual Leg IPG "beats," which are subsequently used to obtain fiducials in the Foot IPG, consistent with various aspects of the present disclosure;

FIG. 10 shows an example flowchart depicting signal processing to segment individual Foot IPG "beats" to produce an averaged IPG waveform of improved SNR, which is subsequently used to determine the fiducial of the averaged Foot IPG, consistent with various aspects of the present disclosure;

FIG. 11 shows an example configuration for obtaining the pulse transit time (PTT), using the first IPG as the triggering pulse for the Foot IPG and ballistocardiogram (BCG), consistent with various aspects of the present disclosure;

FIG. 12 shows another example of a scale with interleaved foot electrodes to inject and sense current from one foot to another foot, and within one foot, consistent with various aspects of the present disclosure;

FIG. 13A shows another example of a scale with interleaved foot electrodes to inject and sense current from one foot to another foot, and to measure Foot IPG signals in both feet, consistent with various aspects of the present disclosure;

FIG. 13B shows another example of a scale with interleaved foot electrodes to inject and sense current from one foot to another foot, and to measure Foot IPG signals in both feet, consistent with various aspects of the present disclosure;

FIG. 13C shows another example approach to floating current sources by using transformer-coupled current sources, consistent with various aspects of the present disclosure;

FIGS. 14A-D show an example breakdown of a scale with interleaved foot electrodes to inject and sense current from one foot to another foot, and within one foot, consistent with various aspects of the present disclosure;

FIG. 15 shows an example block diagram of circuit-based building blocks, consistent with various aspects of the present disclosure;

FIG. 16 shows an example flow diagram, consistent with various aspects of the present disclosure;

FIG. 17 shows an example scale communicatively coupled to a wireless device, consistent with various aspects of the present disclosure;

FIGS. 18A-C show example impedance as measured through different parts of the foot based on the foot position, consistent with various aspects of the present disclosure;

FIG. 19 shows an example of applications provided on an external device for customization of various health goals, training regimes, health diagnostics, and other modalities, consistent with various aspects of the present disclosure;

FIG. 20 shows an example of communicating feedback to an external device of a third party, consistent with various aspects of the present disclosure; and FIG. 21 shows an examples of communicating feedback to an external device, consistent with various aspects of the present disclosure.

While various embodiments discussed herein are amenable to modifications and alternative forms, aspects thereof have been shown by way of example in the drawings and will be described in detail. It should be understood, however, that the intention is not to limit the disclosure to the particular embodiments described. On the contrary, the intention is to cover all modifications, equivalents, and alternatives falling within the scope of the disclosure including aspects defined in the claims. In addition, the term "example" as used throughout this application is only by way of illustration, and not limitation.

DETAILED DESCRIPTION

Various aspects of the present disclosure are directed toward a multi-function scale with a large-area display to present results of the scale's multiple sensing functionalities, as well as other information pertinent to a user. In many embodiments, the multi-function scale is capable of a number of biometric and physiological measurements. Based on the measurements, a physiological condition(s) of the user is displayed on the large-area display between or beneath the user's feet.

In various embodiments a multi-function scale including a display is disclosed, the display being effectively the entire top surface of the scale. Support glass above the display transmits the weight of a user to a bezel along the perimeter of the scale (away from the display), while also transmitting touch-capacitive signals indicative of a user's position and movement on the support glass through the display to scale circuitry. The bezel houses load cells equally spaced along the perimeter of the scale. Each load cell outputs an electrical signal indicative of a mass transmitted from the user through the load cell to the scale circuitry. A support frame is attached to the bezel and supports the display within the bezel. A plurality of translucent electrode leads are embedded into the support glass to provide electrical signals to the scale circuitry; the electrical signals are interpreted by the scale circuitry as being indicative of a condition of a user, such a physiological condition being presented on the display for the user.

In some embodiments of the present disclosure, a display of a multi-function scale is touch-responsive or tilt-responsive. A user's feet (or hands) are sensed. In some embodiments, the user provides input for functional or aesthetic feedback via the display. A user may also change posture, shifting the weight distribution over the scale's load cells to provide user input. The user provided feedback allows for the selection of menu options, test selection, browsing information or articles presented on the display, or the input of test relevant user data such as age, medical conditions, etc. In various embodiments, the touch-responsive screen indicates to scale circuitry the location of a user's feet relative to a plurality of electrodes located across a top surface of the multi-function scale. This permits the processor to select appropriate electrodes for a designated biometric measurement, based, at least in part, on the real-time location of the user's feet on the scale.

In further, more specific, embodiments of the present disclosure, a multi-function scale is communicatively coupled with a user's external device, such as portable electronic devices, an internet router, or other home electronic devices. The scale then communicates and exchanges data with these devices for display and control by a user. In various embodiments, while the multi-function scale is conducting biometric and physiological measurements of the user, the user (by way of the touch-responsive screen) browses today's news communicated to the multi-function scale by the internet router, changes the station on the television or the song playing on a sound system, or reviews their schedule transmitted to the multi-function scale by the user's smartphone.

In yet further implementations of the disclosure directed to smart-homes, a multi-function scale user controls (via the touch-screen display) a plurality of other devices throughout the home such as a climate control system, security system, operation of the shower, etc. The electronic communications between the multi-function scale and the various devices, in some embodiments, include wireless and/or wired communications.

Aspects of the present disclosure are directed toward a multi-function scale that obtains a plurality of impedance-measurement signals while a set of at least three electrodes are concurrently contacting a user. Additionally, various aspects of the present disclosure include determining a plurality of pulse characteristic signals based on the plurality of impedance-measurement signals. One of the pulse characteristic signals is extracted from one of the impedance-measurement signals and is used as a timing reference to extract and process another of the pulse characteristic signals. The signals obtained by the scale are indicative of a physiological condition of the user, such as percentage: muscle mass percentage, body water percentage, among others. The physiological condition of the user is displayed on a large-area display beneath the user's feet, along with other information that is preprogrammed or requested by the user for display such as time of day, traffic conditions, weather, as well as a plurality of other pieces of information are collected.

In another embodiment, an apparatus includes a base unit including a platform area. The apparatus also includes a set of electrodes including a plurality of electrodes over the platform area for contacting one foot of a user and including at least one other electrode configured and arranged for contacting the user at a location along a lower limb (e.g., other foot) that does not include the one foot. Additionally, the apparatus includes pulse-processing circuitry communicatively coupled to, and configured with, the set of electrodes to obtain a plurality of (first and second) impedance-measurement signals while each of the electrodes is concurrently contacting the user and to determine a plurality of (first and second) pulse characteristic signals based on the plurality of (first and second) impedance-measurement signals. At least one of the (first) impedance-measurement signals is obtained within the one foot and another of the (second) impedance-measurement signals is obtained between the one foot and the other location. One of the (first and second) pulse characteristic signals is extracted from one of the impedance-measurement signals and is used as a timing reference to extract and process another of the pulse characteristic signals.

Various aspects of the disclosure are directed to a multi-function scale with a large-area display. The large-area display is programmed to display aesthetically pleasing screen savers, both when in use, or idle. For example, images, animations, and videos, may be presented on the display with overlaid information (as may be selected by the user). In some specific embodiments of the present disclosure, where the multi-function scale, and based on its measurements, has determined a physiological condition in the user indicative of increased stress levels (as indicated by high blood pressure, heart rate, etc.), for example; the multi-function scale displays images or video, such as waves lapping over sand and play accompanying sounds or music, among other sensory devices, intended to calm and sooth the user. In yet further embodiments, based on an assessed condition, as indicated by the multi-function scale measurements, the multi-function scale suggests audibly or visually (through the scale's display) activities, dietary restrictions, or in the case where the indicated condition is life-threatening (e.g., measurements indicating an imminent heart attack or stroke, etc.), calls an ambulance for the user.

Another embodiment is directed to an apparatus having a base unit including a platform area, a set of electrodes and pulse-processing circuitry. The electrodes include a plurality of electrodes over the platform area for contacting a user at a limb extremity (being the hand or foot) and one or more other electrodes for contacting the user at a different location. The pulse-processing circuitry is communicatively coupled to, and configured with, the set of electrodes to obtain a plurality of (first and second) impedance-measurement signals while each of the electrodes is concurrently contacting the user and to determine a plurality of (first and second) pulse characteristic signals based on the plurality of (first and second) impedance-measurement signals. At least one of the (first) impedance-measurement signals is obtained within the limb extremity and another of the (second) impedance-measurement signals is obtained between the limb extremity and the other location. One of the (first and second) pulse characteristic signals is extracted from one of the impedance-measurement signals and is used as a timing reference to extract and process another of the pulse characteristic signals.

Another embodiment of the present disclosure is directed to an apparatus having a platform structure for supporting a user while the user stands on the platform structure, user-targeted circuitry, and a base structure. The base structure includes housing for structurally supporting a person standing on the apparatus and for integrating with a support structure, a display structure, and a communication circuit. The support structure includes a support frame, the platform structure, and sensor circuitry. The platform structure includes a frame and sensor circuitry to engage the user with the sensor circuitry while the user stands on the platform structure, and for collecting physiological data from the user via the sensor circuitry. The display structure, including a display device, is arranged with the support structure for displaying data through the platform structure. Further, the display structure is configured and arranged with the user-targeted circuitry to: monitor physiological parameters of the user over a period of time, and assess a fitness of the user based on one or more of the physiological parameters. The communication circuit, including a communication driver, provides information, including the assessed fitness, from the user-targeted circuitry to the display structure of the apparatus for viewing by the user through the platform structure.

Example display devices include a touch responsive screen located across the top surface of the apparatus and/or other display devices located underneath the platform structure. In various embodiments, the display structure includes a capacitive matrix on its surface and/or is conductively coupled to the platform structure to prevent excessive weight from being exerted on the display structure.

The base structure including the support structure, in some embodiments, includes a set of electrodes, and a pulse-processing circuitry. The pulse-processing circuitry is communicatively coupled to, and configured with, the set of electrodes to obtain impedance-measurement signals while each of the electrodes is concurrently contacting the user, as discussed further herein. The supports structure includes the platform region and sensor circuitry. The support structure is located around the perimeter of the apparatus and transfers the weight of the user on the platform structure through load cells in each corner of the support structure. The platform structure engages with the sensor circuitry while the user stands on the platform structure and physiological data is collected from the user via the sensor circuitry. One way for platform structure to engage with the sensor circuitry while the user stands on the platform structure and for collecting physiological data includes the set of electrodes to contact the platform structure with the sensor circuitry.

In various embodiments of the present disclosure, a multi-function scale includes circuitry such as a camera and image processing circuitry. The camera is directed either at the floor below the scale, flush with the top of the scale, or the surrounding area. Based on the images processed (by the image circuitry) of the area surrounding the scale, the multi-function scale's large-area display depicts an image that mimics the surrounding area when idle. For example, in some embodiments, the scale depicts an image indicative of the flooring below the scale or flush with the top of the scale, minimizing any detraction of aesthetics of the scale. The result is that, when the multi-function scale is idle, the scale is effectively camouflaged from view or at a glance. In other embodiments, the camera is directed at an upward angle, providing a view of the room in which the multi-function scale is located. Based on image data collected by the camera and processed by image processing circuitry, the display presents the prominent colors and patterns found in the room, minimizing the aesthetic detraction of the multi-function scale.

The above discussion/summary is not intended to describe each embodiment or every implementation of the present disclosure. The figures and detailed description that follow also exemplify various embodiments.

Figure 1A:
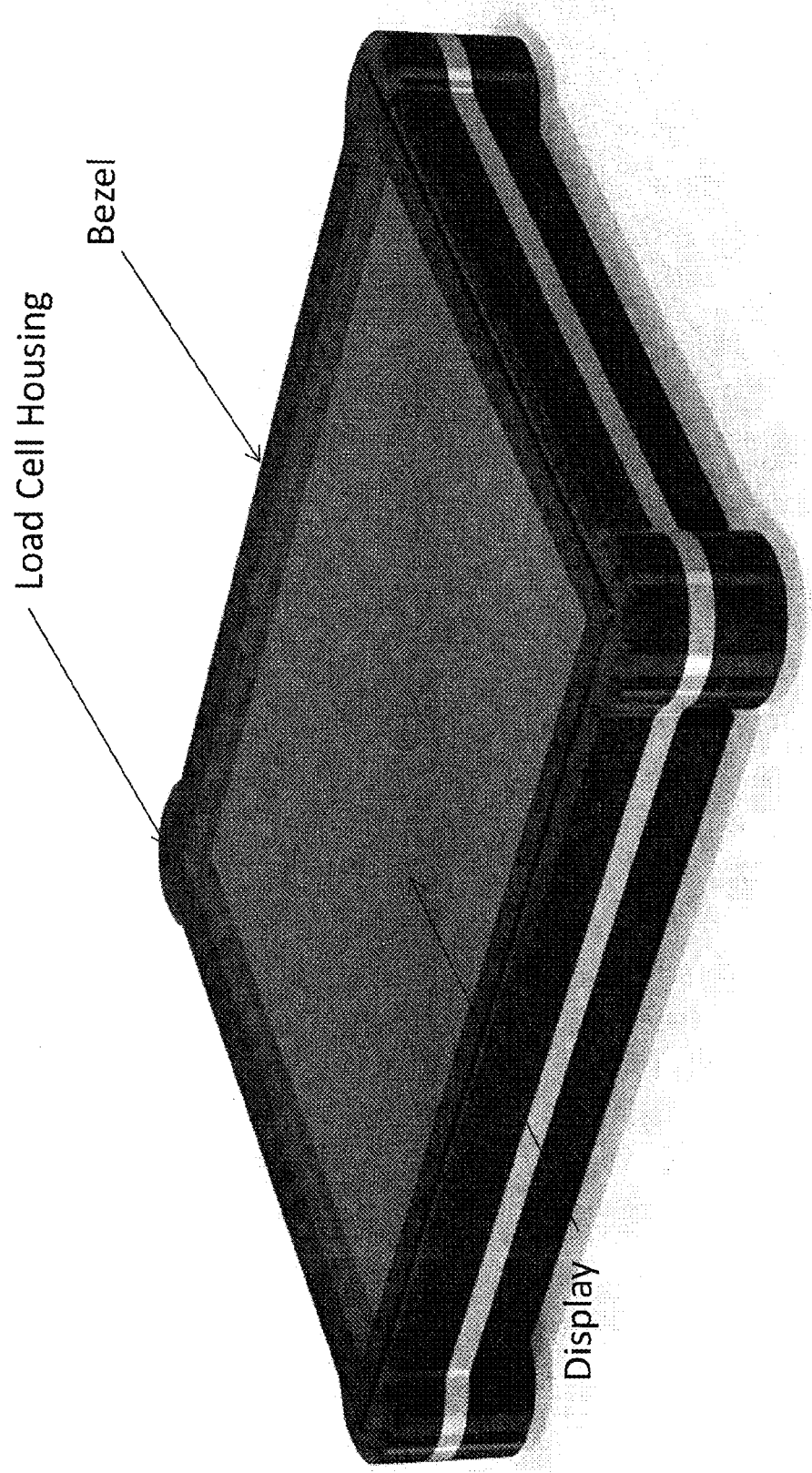
FIG. 1A shows an isometric view of a multi-function scale with large-area display, consistent with various aspects of the present disclosure.
Figure 1B:
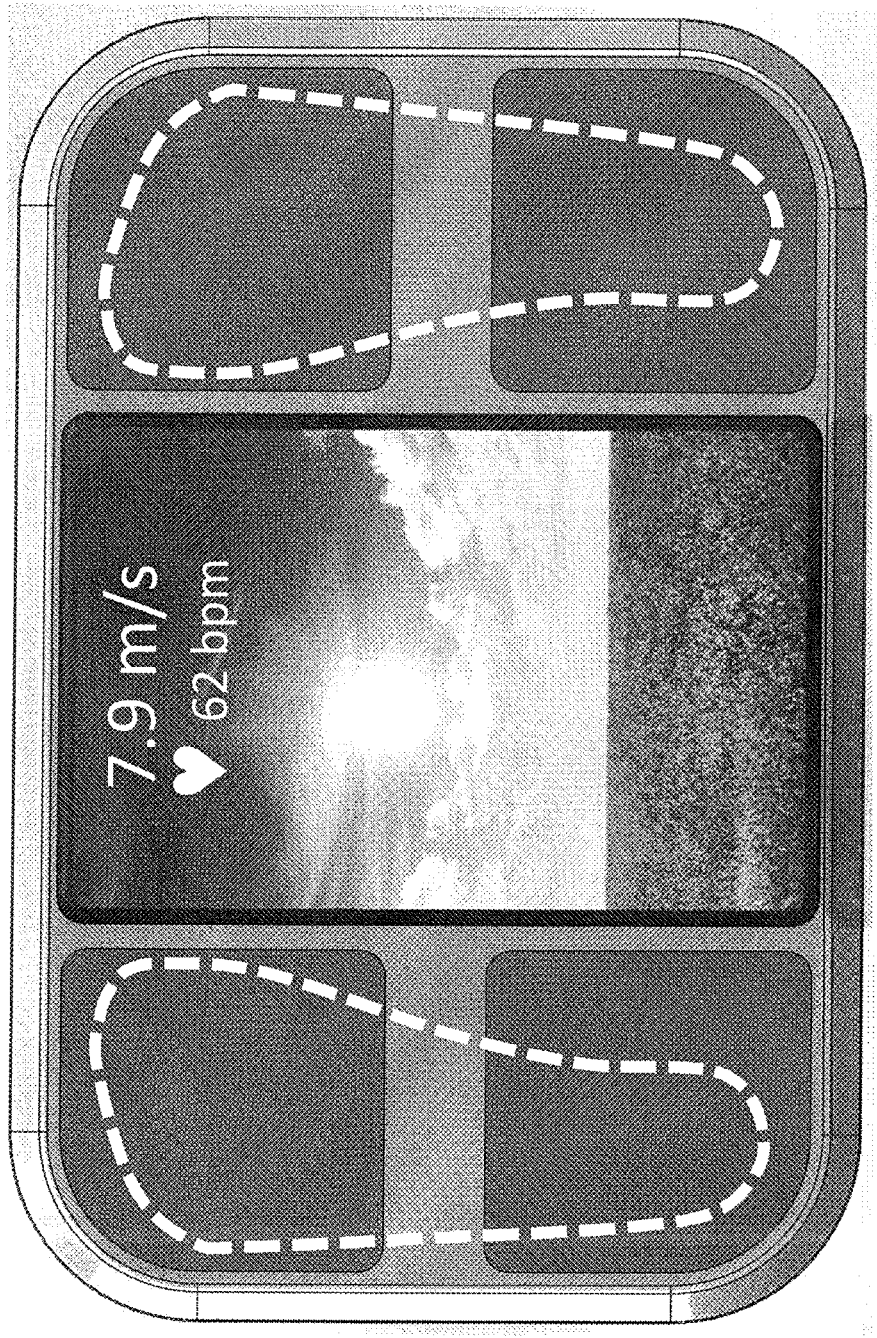
FIG. 1B shows an isometric view of a multi-function scale with large-area display, consistent with various aspects of the present disclosure.

Turning now to the figures, FIG. 1A-1C, illustrate additional aspects pertaining to the categories of users such as discussed above. As is apparent, FIG. 1A-1C provide illustrations of an apparatus (e.g., a scale), and these Figures illustrate and depict communications to users in one or more of the user categories as discussed in Table 1 and this disclosure.

FIG. 1A shows an isometric view of a multi-function scale with a large-area display, consistent with various aspects of the present disclosure. In this particular embodiment, the scale has a primarily rectangular shape with a bezel around the perimeter of the scale that transfers the weight of a user from a top surface of the scale through load cells in each corner. It is to be understood that the aesthetic design of the multi-function scale may take on a plurality of shapes and sizes (based on the needs of the users, e.g., weight requirements, their aesthetic preferences, etc.). A feature of the multi-function scale is the large-area display that makes up the majority of the top surface of the scale. The display, in some embodiments, presents the user with a myriad of information, such as the results of physiological and biometric test results conducted by the scale, entertainment information (while the scale is conducting tests or a weight measurement), and aesthetic screen savers.

In certain specific embodiments of the present disclosure, as shown in FIG. 1B, a large-area display is implemented on the top surface of a multi-function scale, where the display is full length in one direction, but not full width. This display size is closer in dimensions to a tablet computing device (such as an iPad). The electrodes (for physiological and biometric sensing) are on the left and right sides of the display. As discussed above in reference to FIG. 1B and in more detail below in reference to FIGS. 5A-D, the display is capable of presenting a myriad of information to the user.

FIG. 1C shows an apparatus that has a display in the center region, and a user wearable device. The user wearable device includes signal communication circuitry and output circuitry to communicate selected data to a user and provide monitored selected data indicative of physiological parameters. The signal communication circuitry, in various embodiments, includes a wireless signal communication circuitry configured to wirelessly communicate (e.g., send and receive) with other devices. In some embodiments, the user wearable device includes circuitry configured and arranged to monitor selected data indicative of physiological parameters and signal communication circuitry and output circuitry to communicate the selected data to the weighing scale. The weighing scale, in some embodiments, can display the selected data on the display of the weighing scale.

In various embodiments, different user wearable devices are used. In some embodiments, as illustrated by FIG. 1C, the user wearable device includes a wearable wrist device that measures physiological data such as heart rate. In various embodiments, one or more commercially available wrist wearable devices, such as Gear Fit, available from Samsung, and Garmin Forerunner 305, are modified with common protocol data specific to passing the physiological data between the wearable wrist device and the weighing scale. The Garmin Forerunner 305 can provides features including: a training assistant that provides athletes (and users) with precise speed, distance and pace data; training center software which allows users to download workout data for detailed analysis; applications for varying types of sports, such as cycling, cross country skiing, and windsurfing; motion-based mapping, GPS and route sharing capabilities as part of the data acquisition. Such user wearable devices are useful for sharing heart-based data with the scale apparatus as shown in the Figures. In other embodiments, a user wearable device includes a neck wearable device (e.g., an emergency alert system for the elderly) and/or a shoe wearable device.

As illustrated by FIG. 1C, and as further illustrated by FIGS. 2-6, some embodiments include an apparatus comprising a platform region, user-targeted circuitry, and a base unit. The apparatus includes a weighing scale. The base unit integrates the support structure and a display. The support structure includes the platform region and sensor circuitry. The platform region is configured and arranged to support a user while the user stands on the platform region. Further, the platform region engages the user with the sensor circuitry while the user stands on the platform region. The sensor circuitry, in various embodiments, includes electrodes configured and arranged to contact the user. The sensor circuitry collects physiological data from the user. For example, the sensor circuitry obtains a plurality of impedance-measurement signals via the electrodes and determines physiological signals of the user using the impedance-measurement signals. For instance, the platform region engages the user with the sensor circuitry while the user stands on the platform region, and collect physiological data from the user via the sensor circuitry. The display is configured and arranged with the support structure for displaying data through the platform region.

The display is configured and arranged with user-targeted circuitry to monitor a plurality of physiological signals (e.g., determined using the impedance-measurement signals) of the user while the user is standing on the platform region and select data indicative of a physiological parameter of the user based on a threshold value and the plurality of physiological signals. The physiological signals include a plurality of BCG signals and the physiological parameter can include a BCG, in various embodiments. In accordance with some embodiments, at least one of the measured physiological signals may have a signal integrity below a threshold value. That is, the integrity of the signal can be low. A signal integrity, in some embodiments, includes a signal to noise ratio, among other integrity measurements. Thereby, in some embodiments, a threshold value, as used herein, can include a value of a signal integrity.

In various embodiments, the display is configured and arranged with the user-targeted circuitry to determine a signal integrity of each of the plurality of physiological signals and use the determined signal integrities to select the data indicative of the physiological parameter. For example, in response to one of the plurality of physiological signals having a signal integrity that is below the threshold value, the particular physiological signals is disregarded. Disregarding a physiological signals can include not selecting the physiological signal as data indicative of the physiological parameter. Data that is not indicative of the physiological parameter, in various embodiments, may not be sent to the user wearable device. By determining the integrity of the signals prior to sending the data to the user wearable device, in accordance with various embodiments, the user wearable device may process less data. The weighing scale, in various embodiments, can include more processing resources and/or power source than the user wearable device. In some embodiments, the weighing scale can average a subset of the plurality of physiological signals that have signal integrities above the threshold value and select the average as the data indicative of the physiological parameter.

The weighing scale, in various embodiments, includes communication circuitry configured and arranged with the display. The communication circuitry is used to output a signal that includes the data indicative of the physiological parameter to the user wearable device. The user wearable device, in some embodiments, receives the data using the wireless signal receive circuitry. In some embodiments, the user wearable device can include a display to communicate the physiological parameter to the user. Further, the user wearable device can include circuitry configured and arranged to update physiological data of the user based on the communicated physiological parameter. The physiological data can include a plurality of physiological parameters, exercise habits, eating habits, sleeping habits, and/or other data. The physiological data can include data associated with the user that is tracked over time. Alternatively and/or in addition, in some embodiments, the communication circuitry of the weighing scale received selected data indicative of physiological parameters from the user wearable device, as discussed further herein.

In some embodiments, the physiological data is stored on the user wearable device and/or an external device. For example, the user wearable device can include (e.g., wireless) signal communication circuitry configured and arranged to communicate (e.g., wirelessly) with other device. The user wearable device can communicate with the external device, such as an external server, to store the physiological data using the external device and/or to receive particular physiological data. Further, in some embodiments, the user wearable device can use the signal communication circuitry to communicate selected data with the weighing scale. The selected data can include exercise habits, dietary habits, sleeping habits, correlations, tracked physiological data, and/or other data. The data is some embodiments may be used by the weighing scale to perform other functions, such as providing the information to the user using the display, updating a calculation and/or determining correlations, as further discussed herein.

In various embodiments, the user wearable device includes circuitry to monitor selected data indicative of physiological parameters and communicate the selected data to the weighing scale using the signal communication circuitry and output circuitry. In such embodiments, the weighing scale comprises a communication circuitry configured and arranged with a display of the weighing scale to receive the data indicative of the physiological parameters from the signal communication circuitry of the user wearable device. The display is configured and arranged with the user-targeted circuitry to: monitor a plurality of physiological signals of the user while the user is standing on the platform region, and select data indicative of a physiological parameter of the user, for display on one of the user wearable device and the display of the weighing scale, based on a threshold value and at least one of the plurality of physiological signals and the data indicative of the physiological parameters received from the user wearable device.

In some embodiments, the display is configured and arranged with user-targeted circuitry to monitor physiological parameters while the user is standing on the platform region, and communicate an assessed fitness to the user as feedback. In a number of embodiments, the display configured and arranged with the user-targeted circuitry assesses the fitness of the user based on one or more of the physiological parameters. Alternatively, an external device assesses the fitness based on the one or more physiological parameters (e.g., communicated to the external device) and communicates the assessed fitness to the apparatus using a wireless or wired communication. In various embodiments, the physiological parameters of the user are measured when the user is in a resting state and an exertion state, as discussed further herein.

The apparatus, e.g., scale, has display capabilities, e.g., visual and/or sound, and the measurement devices shown in this Figure communicate user physiological data wirelessly (and via the Cloud) to and from an external device (e.g., a portable remote devices such as a smart tablets and cell phones). For example, applications (e.g., apps) are provided on the external devices (e.g., smart phones, tablets, etc.) for customization of various user health goals, training regimes, health diagnostics and other modalities, responsive to the communicated user data.

In some embodiments, the apparatus tracks physiological parameters of the user over time. The apparatus includes interface circuity driving the display. The interface circuitry is located on the apparatus and/or on an external device. The display outputs a signal indicative of the measured physiological parameters to the interface circuit. The interface circuit, responsive to the output signal, tracks physiological parameters of the user over time.

The tracking of physiological parameters is used to assess a fitness of the user. For example, the physiological parameters, tracked over time, are compared to prior-assessed user norms (e.g., prior physiological parameters of the user and/or average value of tracked physiological parameters) or other baselines/population norms (e.g., average values of a particular demographic population). Feedback to the user can include indications of a change in one or more recovery parameters, a deviation from prior-assessed user norms, other baseline/population norms, and a combination thereof.

In various embodiments, the physiological parameters monitored and/or tracked include recovery parameters. Recovery parameters are the user's physiologic recovery to baseline parameters. In some embodiments, the recovery parameters are used to estimate the user's level of cardiovascular fitness. Further, the recovery parameters are measured over time to provide trending and feedback for improvement of the user's fitness. The apparatus can communicate the cardiovascular fitness to the user via the display of the apparatus and/or to one or more external devices.

The recovery parameters are determined by measuring physiological parameters while the user is standing on the platform region in a resting state. The physiological parameters measured during the resting state are indicative of baseline values. In response to measuring the physiological parameters during the resting state, the apparatus (e.g., the scale) and/or an external device instructs the user to enter an exertion state. Further, in response to the user standing on the platform region of the apparatus after the instruction to enter the exertion state, the apparatus (e.g., the scale) measures physiological parameters while the user is standing on the platform region in the exertion state and determines one or more recovery parameters based on the physiological parameters in the resting state and the exertion state. The recovery parameters include a rate of returning to the physiologic parameters in the resting state from the physiological parameters in the exertion state. The physiological parameters, discussed above, are measured while the user is engaged with the sensor circuitry of the apparatus via the platform region of the apparatus (e.g., a scale).

In accordance with some embodiments, the apparatus verifies that the user is in the exertion state based on a comparison of a heart rate of the user in the resting state and a heart rate of the user after the user is instructed to enter the exertion state. The apparatus, for instance, first verifies that the heart rate was sufficiently above, e.g., a threshold value above, the previously measured resting state heart rate. If the heart rate was too low from the previously measured resting state heart rate, the apparatus instructs, e.g., coaches, the user to do additional exercise to raise the user's heart rate prior to repeating the measurements. For example, a weighing scale, using the display, instructs the user to further exercise in response to the heart rate of the user measured after the instruction to enter the exertion state that is below a threshold heart rate value.

In accordance with some embodiments, the apparatus receives information from an external source, such as from an external device, indicative of health habits of the user. The health habits include information such as exercise habits, dietary habits, sleeping habits, etc. The apparatus, using interface circuitry, correlates the health habits with changes in physiological parameters over time. The correlation is communicated to the circuitry, e.g., user-targeted circuitry, of the apparatus and provided as fitness feedback to the user. For example, if a user indicates they have increased their exercise habits, the apparatus displays a correlation between the increase in exercise and changes in physiological parameters and/or fitness of the user. Thereby, the interface circuit determines correlations to the user of benefits of changes in exercise habits based on the tracked physiological parameters and outputs the determined correlation to the user-targeted circuitry arranged with the display of the apparatus.

As further illustrated by FIG. 1C (further illustrated by FIG. 19), the apparatus, in some embodiments, is in communication with at least one other sensor. Such sensor can include an external device, such as a wrist wearable device, a cell phone, a tablet, etc. The apparatus uses data communicated from the at least one other sensor to monitor the one or more physiological parameters. For example, the data communicated is used to refine measurements made by the apparatus.

In many embodiments, the apparatus and/or external source compares a user's physiological parameters to a health metric. Some examples of health metrics include physiological parameters of an average individual of the same sex, age, height, weight, etc., or physiological parameters indicative of a level of fitness to which the user wishes to achieve (e.g., run a marathon, or climb Mount Everest). In one specific embodiment, user-targeted circuitry of the apparatus accesses current physiological parameters of the user and the health metric associated with at least one of a number of the user-specific physiological parameters stored in the data-access circuit (sex, age, height, weight of the user). Current physiological parameters may, for example, be obtained by sensing physiological data of the user and assessing the physiological parameters of the user, as discussed in more detail below, or by accessing recent physiological parameters of the user stored in a data-access circuit. The user-targeted circuitry compares the current physiological parameters to the stored health metric to determine a fitness of the user.

In many embodiments, the apparatus (e.g., a scale) determines (and displays) action(s) to encourage improvement of the fitness, after determining the fitness of the user. For example, where a user's determined physiological parameters are indicative of a lack of cardiovascular fitness, the apparatus suggests that the user add a one mile jog into his or her daily fitness routine. In many embodiments, the user-targeted circuitry transmits (via the data-access circuit) to an external device (e.g., personal electronic device) associated with the user, the physiological parameters, physiological data, recommended physical regimens, and/or other data indicative of the physical health of the user. In some embodiments, the external device stores such data and/or further analyzes the data in view of other stored data such as data indicative of diet and caloric intake of the user or the current physical regimen of the user. The external device instructs the user to adjust his or her diet and/or physical regimen accordingly. In further embodiments, the external device transmits stored data indicative of the diet and caloric intake of the user, the current physical regimen of the user, or other health related data. The user-targeted circuitry considers such data when determining the physiological parameters of the user to further improve the accuracy of such determined physiological parameters.

Figure 2:
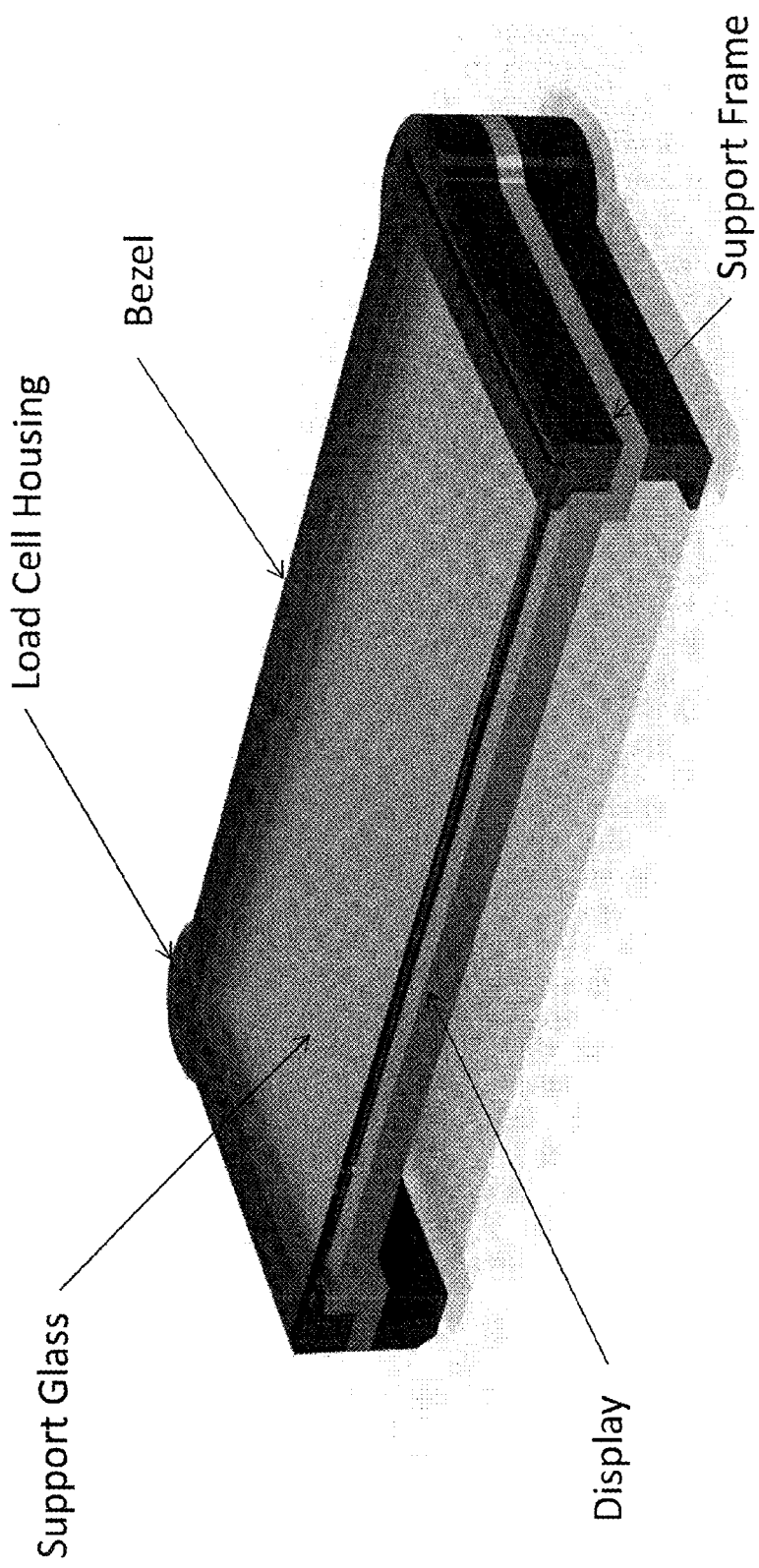
FIG. 2 shows an isometric, cross-sectional view of a multi-function scale with large-area display, consistent with various aspects of the present disclosure.

FIG. 2 shows an isometric, cross-sectional view of a multi-function scale with a large-area display, consistent with various aspects of the present disclosure. Support glass above a display transmits the weight of a user to a bezel along the perimeter of the scale (away from the display), while also transmitting touch-capacitive signals indicative of a user's position and/or movement on the support glass, through the display to scale circuitry. A support frame is attached to the bezel and supports the display within the bezel. The bezel support frame houses load cells equally spaced along the perimeter of the scale. Each load cell outputs an electrical signal indicative of a mass transmitted from the user through the load cell to the scale circuitry (which interprets the electrical signals and presents the weight of the user on the display). A plurality of translucent electrode leads are embedded into the support glass to provide electrical signals to the scale circuitry, and the electrical signals are interpreted by the scale circuitry as being indicative of a condition of a user, with the condition being presented on the display for the user.

Load bearing characteristics of the multi-function scale provides both functionality and longevity. The support glass, in conjunction with the bezel and support frame, minimizes the load transfer to the display while still maintaining sufficient conductivity through the support glass to the display to allow for touch-screen functionality. If the support glass is too compliant, under the user's weight, excessive force exerted on the display may cause damage. If the glass is not conductively coupled to the display (e.g., due to a gap there-between), touch-screen functionality of the scale may be challenging or inapplicable. Accordingly, one or more embodiments address such issues with a support frame for a display that allows for minimal compliance, by which the display remains conductively coupled to the support glass while preventing excessive force from being exerted on the display (that would otherwise cause damage).

Figure 3A:
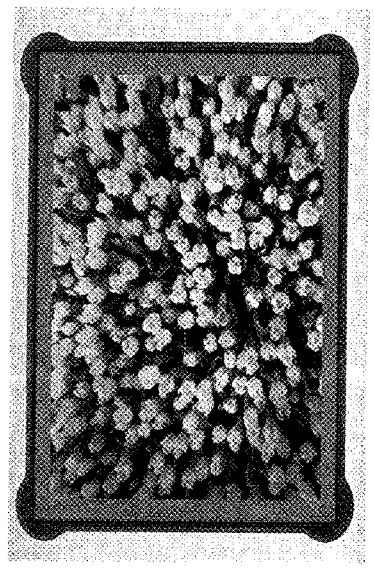
FIGS. 3A-D show top views of a number of multi-function scale displays, consistent with various aspects of the present disclosure.

FIG. 3A-D shows top views of a number of multi-function scale displays, consistent with various aspects of the present disclosure. FIG. 3A presents an exemplary image that is selected by a user as a "screen saver," and displayed by the scale when not in use. In further embodiments, the scale, when not in use, presents a slide-show of images selected by the user, such as family-photos. In more specific embodiments of the present disclosure, a camera is communicatively coupled to the multi-function scale and operates with facial recognition software for identifying the user. Based on the identified user, the scale operates in accordance with user-specific aspects as relate to physiology or preferences such as for a "screen saver." For instance, biometric and physiological tests are conducted, with the test results saved to the identified user's file (and/or the results sent to a user's doctor for further review and analysis), as well as a number of other functionalities, such as playing the user's favorite musical artist and the pertinent information is loaded to the display to present the user with the pertinent information.

Figure 3B:
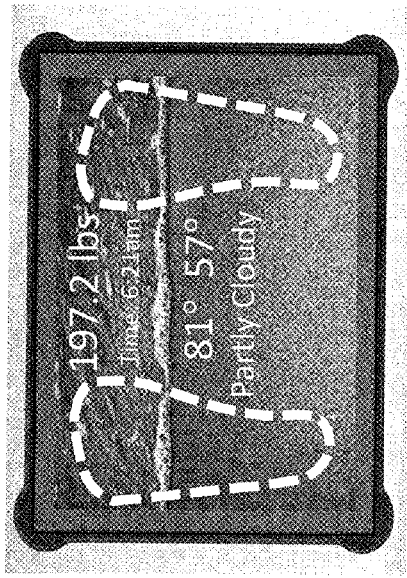
Figure 3C:
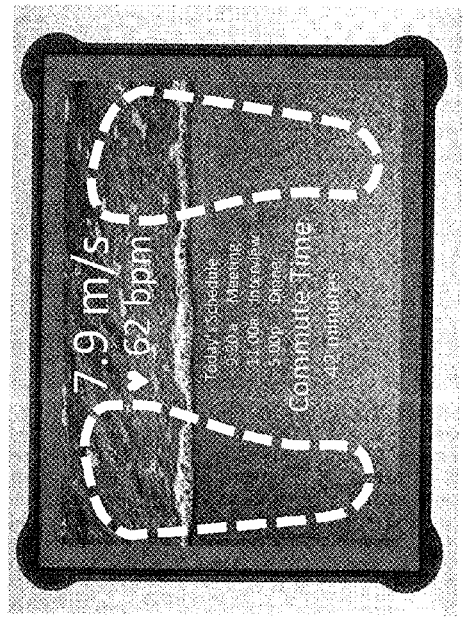
Figure 3D:
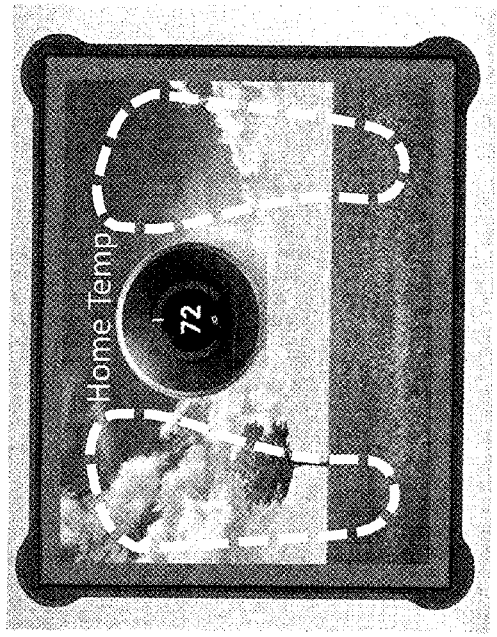

As shown in FIG. 3B, a relaxing ambience is provided to the room where the multi-function scale is located, such as by displaying a video of waves lapping over sand. In some embodiments, the scale plays an audio track associated with the video. In FIGS. 3B-D, while the scale conducts tests on the user (e.g., weight measurements, biometric and physiological tests) at a time programmable by the user, and/or other times, the user is able to access other information from the scale such as the user's current weight, pulse rate, and time of day, among other user-configurable information. In further more specific embodiments (as shown in FIGS. 3B-D), the scale displays weather conditions, home climate, commute times, user's daily schedule, personal reminders, or other information as is collected by the scale via a wired and/or wireless connection to the internet, or to a smart device (e.g., a hand-held mobile phone). As shown in FIG. 3D, in implementations of the disclosure directed to smart-homes, a multi-function scale user controls (via the touch-screen display) a plurality of other devices throughout the home such as a climate control system, security system, operation of the shower, etc. The electronic communications between the multi-function scale and the various devices includes a wireless and/or wired communications.

Figure 4:
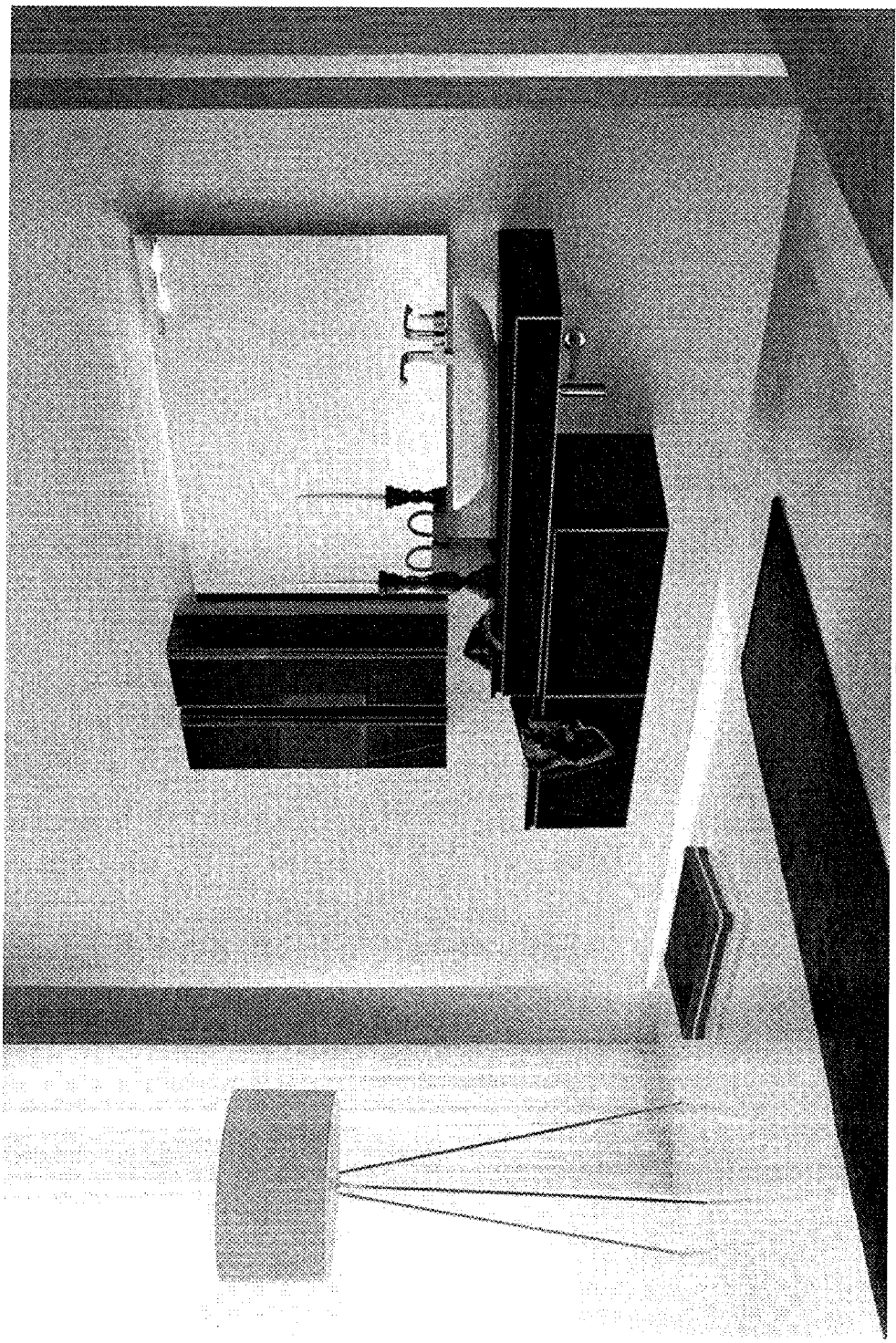
FIG. 4 shows a multi-function scale with a large-area display, consistent with various aspects of the present disclosure.

FIG. 4 shows a multi-function display with large-area display (e.g., for a bathroom), consistent with various aspects of the present disclosure. In the present embodiment, the multi-function scale includes circuitry, such as a camera and image processing circuitry. The camera may be directed at the floor below the scale, flush with the top of the scale, or the surrounding area. Based on the images processed (by the image processing circuitry) of the area surrounding the scale, the multi-function scale's large-area display depicts an image that mimics the surrounding area when idle. As shown in FIG. 4, the room is primarily furnished in black and white. The image processing circuitry identifies this black and white room theme based on the images captured by the camera and selects a color or combination of colors in a pattern or design that would mimic the décor of the room. As a result, the scale is more likely to blend into the room and minimize the likelihood that the scale will detract from the ambiance. In embodiments where the camera is directed at the surrounding floor, the scale depicts an image indicative of the flooring below the scale or flush with the top of the scale, which minimizes detraction of aesthetics of the scale. In either embodiment discussed above, when the multi-function scale is idle, from a glance the scale is effectively camouflaged. In other embodiments, the user and/or another person, such as an interior designer, selects a theme for the display based on the desired look for the room where the multi-function scale is placed.

Figure 5A:
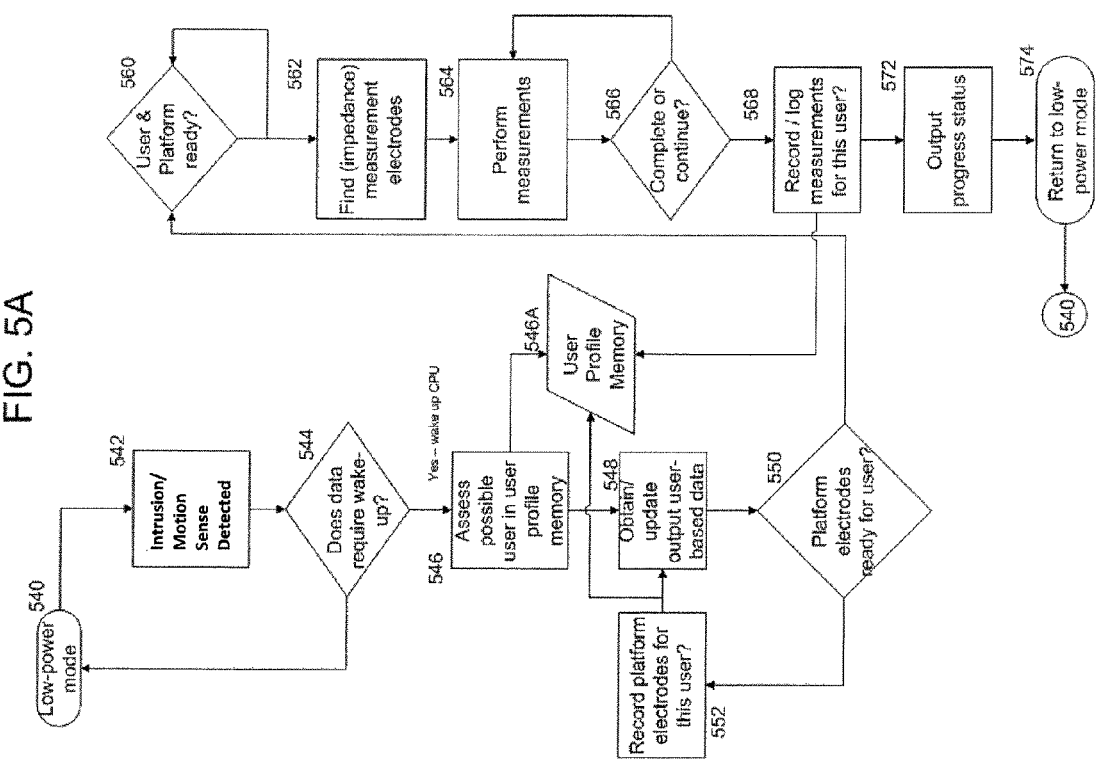
FIG. 5A is a flow chart illustrating an example manner in which a user-specific physiologic meter/scale is programmed to provide features consistent with aspects of the present disclosure.

FIG. 5A is a flow chart depicting an example manner in which a user specific physiologic meter or scale is programmed in accordance with the present disclosure. This flowchart uses a computer processor circuit (or CPU) along with a memory circuit shown herein as user profile memory 546A. With the coaching information, such as that shown in TABLE 1, the user profile memory is automatically updated by the CPU to coincide with the user's health progress/performance, age, weight, various cardiovascular criteria (e.g., as measured by the PVW), and/or other related conditions. The CPU operates in a low-power consumption mode, which may be in off mode or a low-power sleep mode, and at least one other higher power consumption mode of operation. As exemplary circuits for transitioning between such a low-power and higher power modes, the CPU is integrated with presence and/or motion sense circuits, such as a passive infrared (PIR) circuit and/or gyro PIR circuit. In a typical application, the PIR circuit provides a constant flow of data indicative of amounts of radiation (e.g., body heat or bio thermal) sensed in a field of view directed by the PIR circuit. For instance, the PIR circuit can be installed behind a transparent upper surface of the platform (such as through the display screen of the platform apparatus) and installed at an angle so that the motion of the user, as the user approaches the platform apparatus, is sensed. Radiation from the user, upon reaching a certain detectable level, wakes up the CPU which then transitions from the low-power mode, as depicted in block 540, to a regular mode of operation. In alternative embodiments, the CPU transitions from the low-power mode of operation in response to another remote/wireless input used as an intrusion to awaken the CPU. In other embodiments, motion can be sensed with a single integrated microphone or microphone array, to detect the sounds of a user approaching, or user motion is detected by an accelerometer integrated in the scale.

Accordingly, from block 540, flow proceeds to block 542 where the user or other presence is sensed as data is received at the platform apparatus. At block 544, the circuitry assesses whether the received data qualifies as requiring a wake up. If not, flow turns to block 540. If however, wake up is required, flow proceeds from block 544 to block 546 where the CPU assesses whether a possible previous user has approached the platform apparatus. This assessment is performed by the CPU accessing the user profile memory 546A and comparing data stored therein for one or more such previous users with criteria corresponding to the received data that caused the wake up. Such criteria includes, for example, the time of the day (early morning or late morning), the pace at which the user approached the platform apparatus as sensed by the motion detection circuitry, the height of the user as indicated by the motion sensing circuitry and/or a camera installed and integrated with the CPU, and/or more sophisticated bio-metric data provided by the user and/or automatically by the circuitry in the platform apparatus.

As discussed herein, in various embodiments, such circuitry includes one or more of the following user-specific attributes: foot length, type of foot arch, weight of user, manner and speed at which the user steps onto the platform apparatus, and/or sounds made by the user's motion or by speech. As is also conventional, facial or body-feature recognition is used in connection with the camera and comparisons of images therefrom to images in the user profile memory.

From block 546, flow proceeds to block 548 where the CPU obtains and/or updates user corresponding data in the user profile memory. As a learning program is developed in the user profile memory, each access and use of the platform apparatus is used to expand on the data and profile for each such user. From block 548, flow proceeds to block 550 where a decision is made regarding whether the set of electrodes at the upper surface of the platform is ready for the user, which, in some embodiments, is based on the data obtained from the user profile memory. For example, delays may ensue from the user moving his or her feet about the upper surface of the platform apparatus, as may occur while certain data is being retrieved by the CPU (whether internally or from an external source such as a program or configuration data updates from the Internet cloud) or when the user steps over a certain area configured for providing display information back to the user. If the electrodes are not ready for the user, flow proceeds from block 550 to block 552 to accommodate this delay.

Once the CPU determines that the electrodes are ready for use while the user is standing on the platform surface, flow proceeds to block 560. Stabilization of the user on the platform surface may be ascertained by injecting current through the electrodes via the interleaved arrangement thereof. Where such current is returned via other electrodes for a particular foot and/or foot size, and is consistent for a relatively brief period of time (e.g., a few seconds), the CPU assumes that the user is standing still and ready to use the electrodes and related circuitry.

At block 560, a decision is made that both the user and the platform apparatus are ready for measuring impedance and certain segments of the user's body, including at least one foot.

The remaining flow of FIG. 5A includes the application and sensing of current through the electrodes for finding the optimal electrodes (562) and for performing impedance measurements (block 564). These measurements are continued until completed at block 566 and the measurements are recorded and are logged in the user profile memory for this specific user, at block 568. At block 572, the CPU generates output data to provide feedback as to the completion of the measurements. The feedback, in some embodiments, is indicated as a request via the user profile for this user, as an overall report on the progress for the user relative to previous measurements made for this user and that are stored in the user profile memory. In such embodiments, the feedback is shown on the display, through a speaker with co-located apertures in the platform's housing for audible reception by the user, and/or by vibration circuitry which, upon vibration under control of the CPU, the user can sense through one or both feet while standing on the scale. From this output at block 572, flow returns to the low-power mode as indicated at block 574 with the return to the beginning of the flow at block 540.

FIG. 5B shows current paths 500 through the body of a user 505 standing on a scale 510 for the IPG trigger pulse and Foot IPG, consistent with various aspects of the present disclosure. Impedance measurements 515 are measured when the user 505 is standing and wearing clothing articles over the feet such as socks or shoes, within the practical limitations of capacitive-based impedance sensing, with energy limits considered safe for human use. The measurements 515 can also be made with non-clothing material placed between the user's bare feet and contact electrodes, such as thin films or sheets of plastic, glass, paper or wax paper, whereby the electrodes operate within energy limits considered safe for human use. The IPG measurements are also sensed in the presence of callouses on the user's feet that normally diminish the quality of the signal.

As shown in FIG. 5B, the user 505 is standing on a scale 510, where the tissues of the user's body is modeled as a series of impedance elements, and where the time-varying impedance elements change in response to cardiovascular and non-cardiovascular movements of the user. ECG and IPG measurements are sensed through the feet. Measuring ECG and IPG measurements is challenging due to small impedance signals with (1) low SNR, and because they are (2) frequently masked or distorted by other electrical activity in the body such as the muscle firings in the legs to maintain balance. The human body is unsteady while standing still, and constant changes in weight distribution occur to maintain balance. As such, cardiovascular signals that are measured with weighing scale-based sensors typically yield signals with poor SNR, such as the Foot IPG and standing BCG. Thus, such scale-based signals use a stable and high quality synchronous timing reference, to segment individual heartbeat-related signals for signal averaging to yield an averaged signal with higher SNR versus respective individual measurements.

The ECG, in accordance with various embodiments, is used as the reference (or trigger) signal to segment a series of heartbeat-related signals measured by secondary sensors (optical, electrical, magnetic, pressure, microwave, piezo, etc.) for averaging a series of heartbeat-related signals together, to improve the SNR of the secondary measurement. The ECG has an intrinsically high SNR when measured with body-worn gel electrodes, or via dry electrodes on handgrip sensors. In contrast, the ECG has a low SNR when measured using foot electrodes while standing on said scale platforms; unless the user is standing perfectly still to eliminate electrical noises from the leg muscles firing due to body motion. As such, ECG measurements at the feet while standing are considered to be an unreliable trigger signal (low SNR). Therefore, it is often difficult to obtain a reliable cardiovascular trigger reference timing when using ECG sensors incorporated in base scale platform devices. Both Inan, et al. (IEEE Transactions on Information Technology in Biomedicine, 14:5, 1188-1196, 2010) and Shin, et al. (Physiological Measurement, 30, 679-693, 2009) have shown that the ECG component of the electrical signal measured between the two feet while standing was rapidly overpowered by the electromyogram (EMG) signal resulting from the leg muscle activity involved in maintaining balance.

The accuracy of cardiovascular information obtained from weighing scale platforms is influenced by measurement time. The number of beats obtained from heartbeat-related signals for signal averaging is a function of measurement time and heart rate. The Mayo Clinic cites that typical resting heart rates range from 60 to 100 beats per minute. Therefore, short signal acquisition periods may yield a low number of beats to average, which may cause measurement uncertainty, also known as the standard error in the mean (SEM). SEM is the standard deviation of the sample mean estimate of a population mean. Where, SE is the standard error in the samples N, which is related to the standard error or the population S.

$$SE = \frac{S}{\sqrt{N}}$$

For example, a five second signal acquisition period may yield a maximum of five to eight beats for ensemble averaging, while a 10 second signal acquisition could yield 10-16 beats. However, the number of beats available for averaging and SNR determination is usually reduced for the following factors; (1) truncation of the first and last ensemble beat in the recording by the algorithm, (2) triggering beats falsely missed by triggering algorithm, (3) cardiorespiratory variability, (4) excessive body motion corrupting the trigger and Foot IPG signal, and (5) loss of foot contact with the measurement electrodes.

Sources of noise can use multiple solutions for overall SNR improvements for the signal being averaged. Longer measurement times increase the number of beats lost to truncation, false missed triggering, and excessive motion. Longer measurement times also reduce variability from cardiorespiratory effects. Therefore, if shorter measurement times (e.g., less than 30 seconds) are used for scale-based sensor platforms, sensing improvements need to tolerate body motion and loss of foot contact with the measurement electrodes.

The human cardiovascular system includes a heart with four chambers, separated by valves that return blood to the heart from the venous system into the right side of the heart, through the pulmonary circulation to oxygenate the blood, which then returns to the left side of the heart, where the oxygenated blood is pressurized by the left ventricles and is pumped into the arterial circulation, where blood is distributed to the organs and tissues to supply oxygen. The cardiovascular or circulatory system is designed to ensure maintenance of oxygen availability and is often the limiting factor for cell survival. The heart normally pumps five to six liters of blood every minute during rest and maximum cardiac output during exercise can increase up to seven-fold, by modulating heart rate and stroke volume. The factors that affect heart rate include the degree of autonomic innervation, fitness level, age and hormones. Factors affecting stroke volume include heart size, fitness level, contractility or pre-ejection period, ejection duration, preload or end-diastolic volume, and afterload or systemic resistance. The cardiovascular system is constantly adapting to maintain a homeostasis (set point) that minimizes the work done by the heart to maintain cardiac output. As such, blood pressure is continually adjusting to minimize work demands during rest. Cardiovascular disease encompasses a variety of abnormalities in (or that affect) the cardiovascular system that degrade the efficiency of the system, which include but are not limited to chronically elevated blood pressure, elevated cholesterol levels, edema, endothelial dysfunction, arrhythmias, arterial stiffening, atherosclerosis, vascular wall thickening, stenosis, coronary artery disease, heart attack, stroke, renal dysfunction, enlarged heart, heart failure, diabetes, obesity and pulmonary disorders.

Each cardiac cycle results in a pulse of blood being delivered into the arterial tree. The heart completes cycles of atrial systole, delivering blood to the ventricles, followed by ventricular systole delivering blood into the lungs and the systemic arterial circulation, where the diastole cycle begins. In early diastole the ventricles relax and fill with blood, then in mid-diastole the atria and ventricles are relaxed and the ventricles continue to fill with blood. In late diastole, the sinoatrial node (the heart's pacemaker) depolarizes then contracts the atria, the ventricles are filled with more blood and the depolarization then reaches the atrioventricular node and enters the ventricular side, beginning the systole phase. The ventricles contract, and the blood is pumped from the ventricles to the arteries.

The ECG is the measurement of the heart's electrical activity and can be described in five phases. The P-wave represents atrial depolarization, the PR interval is the time between the P-wave and the start of the QRS complex. The QRS wave complex represents ventricular depolarization. The QRS complex is the strongest wave in the ECG and is frequently used as the de facto timing reference for the cardiovascular cycle. Atrial repolarization is masked by the QRS complex. The ST interval then follows which represents the period of zero potential between ventricular depolarization and repolarization. The cycle concludes with the T-wave representing ventricular repolarization.

The blood ejected into the arteries creates vascular movements due to the blood's momentum. The blood mass ejected by the heart first travels headward in the ascending aorta and travels around the aortic arch then travels down the descending aorta. The diameter of the aorta increases significantly during the systole phase due to the high compliance (low stiffness) of the aortic wall. Blood traveling in the descending aorta then bifurcates in the iliac branch, which then transitions into a stiffer arterial region due to the muscular artery composition of the leg arteries. The blood pulsation continues down the leg and foot. All along the way, the arteries branch into arteries of smaller diameter until reaching the capillary beds where the pulsatile blood flow turns into steady blood flow, delivering oxygen to the tissues. The blood then returns to the venous system terminating in the vena cava, where blood returns to the right atrium of the heart for the subsequent cardiac cycle.

Surprisingly, high quality simultaneous recordings of the Leg IPG and Foot IPG are attainable in a practical manner (e.g., a user operating the device correctly simply by standing on the impedance body scale foot electrodes), and is used to obtain reliable trigger fiducial timings from the Leg IPG signal. This acquisition is less sensitive to motion-induced noise from the Leg EMG than often compromises Leg ECG measurements. Furthermore, interleaving the two Kelvin electrode pairs for a single foot results in a design that is insensitive to foot placement within the boundaries of the overall electrode area. As such, the user is no longer constrained to comply with accurate foot placement on conventional single foot Kelvin arrangements, which are prone to introducing motion artifacts into the IPG signal, or result in a loss of contact if the foot is slightly misaligned. Interleaved designs begin when one or more electrode surfaces cross over a single imaginary boundary line separating an excitation and sensing electrode pair. The interleaving is configured to maintain uniform foot surface contact area on the excitation and sensing electrode pair, regardless of the positioning of the foot over the combined area of the electrode pair.

Various aspects of the present disclosure include a weighing scale platform (e.g., scale 110) of an area sufficient for an adult of average size to stand comfortably still and minimize postural swaying. The nominal scale length (same orientation as foot length) is 12 inches and the width is 12 inches. The width can be increased to be consistent with the feet at shoulder width or slightly broader (e.g., 14 to 18 inches, respectively).

FIG. 6 shows an example of the insensitivity to foot placement 600 on scale electrode pairs 605/610 with multiple excitation paths 620 and sensing current paths 615, consistent with various aspects of the present disclosure. An aspect of the platform is that it has a thickness and strength to support a human adult of at least 200 pounds without fracturing. Another aspect of the device platform is comprised of at least six electrodes, where the first electrode pair 605 is solid and the second electrode pair 610 is interleaved. Another aspect is that the first and second interleaved electrode pairs 605/610 are separated by a distance of at least 40+/−5 millimeters, where the nominal separation of less than 40 millimeters has been shown to degrade the single Foot IPG signal. Another key aspect is the electrode patterns are made from materials with low resistivity such as stainless steel, aluminum, hardened gold, ITO, index matched ITO (IMITO), carbon printed electrodes, conductive tapes, silver-impregnated carbon printed electrodes, conductive adhesives, and similar materials with resistivity lower than 300 ohms/sq. In the certain embodiments, the resistivity is below 150 ohms/sq. The electrodes are connected to the electronic circuitry in the scale by routing the electrodes around the edges of the scale to the surface below, or through at least one hole in the scale (e.g., a via hole).

Suitable electrode arrangements for dual Foot IPG measurements can be realized in other embodiments. In certain embodiments, the interleaved electrodes are patterned on the reverse side of a thin piece (e.g., less than 2 mm) of high-ion-exchange (HIE) glass, which is attached to a scale substrate and used in capacitive sensing mode. In certain embodiments, the interleaved electrodes are patterned onto a thin piece of paper or plastic which are rolled up or folded for easy storage. In certain embodiments, the interleaved electrodes are integrated onto the surface of a tablet computer for portable IPG measurements. In certain embodiments, the interleaved electrodes are patterned onto a kapton substrate that is used as a flex circuit.

In certain embodiments, the scale area has a length of 10 inches with a width of eight inches for a miniature scale platform. Alternatively, the scale may be larger (up to 36 inches wide) for use in bariatric class scales. In certain embodiments, the scale platform with interleaved electrodes is incorporated into a floor tile that is incorporated into a room such as a bathroom. In certain embodiments, the scale folds in half with a hinge for improved portability and storage. Alternatively, the scale platform is comprised of two separable halves, one half for the left foot and the other half for the right foot, for improved portability and storage. In certain embodiments for ambulatory measurements, the interleaved excitation and sensing electrode pairs are incorporated into a shoe insert for the detection of heart rate and a corresponding pulse arrival time (PAT). Alternatively, the interleaved excitation and sensing electrode pairs are incorporated into a pair of socks, to be worn for the detection of heart rate and a corresponding PAT.

In some embodiments, the leg and foot impedance measurements are simultaneously carried out using a multi-frequency approach, in which the leg and foot impedances are excited by currents modulated at two different frequencies, and the resulting voltages are selectively measured using a synchronous demodulator. This homodyning approach is used to separate signals (in this case, the voltage drop due to the imposed current) with accuracy and selectivity.

This measurement configuration is based on a four-point configuration in order to minimize the impact of the contact resistance between the electrode and the foot, a practice well-known in the art of impedance measurement. In this configuration the current is injected from a set of two electrodes (the "injection" and "return" electrodes), and the voltage drop resulting from the passage of this current through the resistance is sensed by two separate electrodes (the "sense" electrodes), usually located in the path of the current. Since the sense electrodes are not carrying any current (by virtue of their connection to a high-impedance differential amplifier), the contact impedance does not significantly alter the sensed voltage.

In order to sense two distinct segments of the body (the legs and the foot), two separate current paths are defined by way of electrode positioning. Therefore two injection electrodes are used, each connected to a current source modulated at a different frequency. The injection electrode for leg impedance is located under the plantar region of the left foot, while the injection electrode for the Foot IPG is located under the heel of the right foot. Both current sources share the same return electrode located under the plantar region of the right foot. This is an illustrative example; other configurations may be used.

The sensing electrodes can be localized so as to sense the corresponding segments. Leg IPG sensing electrodes are located under the heels of each foot, while the two foot sensing electrodes are located under the heel and plantar areas of the right foot. The inter-digitated nature of the right foot electrodes ensures a four-point contact for proper impedance measurement, irrespective of the foot position, as already explained.

FIG. 7A depicts an example block diagram of circuitry for operating core circuits and modules of the multi-function scale, used in various specific embodiments of the present disclosure. Consistent with yet further embodiments of the present disclosure, FIG. 7A depicts an example block diagram of circuitry for operating core circuits and modules, including, for example, the operation of a CPU with the related and more specific circuit blocks/modules in FIGS. 8A-8B. As shown in the center of FIG. 7A, the main computer circuit 770 is shown with other previously-mentioned circuitry in a generalized manner without showing some of the detailed circuitry such as for amplification and current injection/sensing (772). The computer circuit 770 can be used as a control circuit with an internal memory circuit for causing, processing and/or receiving sensed input signals as at block 772. As discussed, these sensed signals are responsive to injection current and/or these signals are sensed at least for initially locating positions of the foot or feet on the platform area, by less complex grid-based sense circuitry surrounding the platform area as is conventional in capacitive touch-screen surfaces which, in certain embodiments, the platform area includes.

As noted, the memory circuit is used not only for the user profile memory, but also to provide configuration and/or program code and/or other data such as user-specific data from another authorized source such as from a user monitoring his/her logged data and/or profile from an external device, such as a remote desk-top. The external device communicates with and access such data via a wireless communication circuit 776 via a wireless modem, router, ISDN channel, cellular systems, Bluetooth and/or other broadband pathway or private channel. For example, the wireless communication circuit 776 provides an interface between an application on the user's cellular telephone/tablet (e.g., phablet, IPhone and/or IPad) and the platform apparatus, wherefrom the IPhone output/input interface for the platform (scale) apparatus including, for example, an output display, speaker and/or microphone, and vibration circuitry; each of these I/O aspects and components being discussed herein in connection with other example embodiments.

A camera 778 and image encoder circuit 780 (with compression and related features) can also be incorporated as an option. As discussed above, the weighing scale components, as in block 782, are also optionally included in the housing which encloses and/or surrounds the platform apparatus.

For long-lasting battery life in the platform apparatus (batteries not shown), at least the CPU 770, the wireless communication circuit 776, and other current draining circuits are inactive unless and until activated in response to the intrusion/sense circuitry 788. As shown, one specific implementation employs a Conexant chip (e.g., CX93510) to assist in the low-power operation. This type of circuitry is specifically designed for motion sensors configured with a camera for visual verification and image and video monitoring applications (such as by supporting JPEG and MJPEG image compression and processing for both color and black and white images). When combined with an external CMOS sensor, the chip retrieves and stores compressed JPEG and audio data in an on-chip memory circuit (e.g., 256 KB/128 KB frame buffer) so as to alleviate the necessity of external memory. The chip uses a simple register set via the microprocessor interface and allows for wide flexibility in terms of compatible operation with another microprocessor.

In one specific embodiment, a method of using the platform with the plurality of electrodes concurrently contacting a limb of the user, includes operating such to automatically obtain measurement signals from the plurality of electrodes. As noted above, these measurement signals may be through less-complex (e.g., capacitive grid-type) sense circuitry. Before or while obtaining a plurality of measurement signals by operating the circuitry, the signal-sense circuitry 788 is used to sense wireless-signals indicative of the user approaching the platform and, in response, cause the CPU circuitry 770 to transition from a reduced power-consumption mode of operation and at least one higher power-consumption mode of operation. After the circuitry is operating in the higher power-consumption mode of operation, the CPU accesses the user-corresponding data stored in the memory circuit and thereafter causes a plurality of impedance-measurement signals to be obtained by using the plurality of electrodes while they are contacting the user via the platform; therefrom, the CPU generates signals corresponding to cardiovascular timings of the user.

This method employs the signal-sense circuit as a passive infrared detector and with the CPU programmed (as a separate module) to evaluate whether radiation from the passive infrared detector is indicative of a human. For example, in response to a sensed levels of radiation that corresponds to a live being that has a size which is less than a person of a three-foot height, and/or not being sensed as moving for more than a couple seconds, the sensed levels of radiation is assessed as being a non-human.

Accordingly, in response to user be recognized as human, the CPU is activated and begins to the discernment process of which user might be approaching. This is performed by the CPU accessing the user-corresponding data stored in the memory circuit (the user profile memory). If the user is recognized based on parameters such as discussed above (e.g., time of morning, speed of approach, etc.), the CPU also selects one of a plurality of different types of user-discernible visual/audible/tactile information and for presenting the discerned user with visual/audible/tactile information that was retrieved from the memory as being specific to the user. For example, user-selected visual/audible data is outputted for the user. Also, responsive to the motion detection indication, the camera is activated to capture at least one image of the user while the user is approaching the platform (and/or while the user is on the platform to log confirmation of the same user with the measured impedance information). As shown in block 774 of FIG. 7A, where a speaker is also integrated with the CPU, the user can simply command the platform apparatus to start the process and activation accordingly proceeds.

In another such method, the circuitry of FIG. 7A is used with the plurality of electrodes being interleaved and engaging the user, as a combination weighing scale (via block 782) and a physiologic user-specific impedance-measurement device. By using the impedance-measurement signals and obtaining at least two impedance-measurement signals between one foot of the user and another location of the user, the interleaved electrodes assist the CPU in providing measurement results that indicate one or more of the following user-specific attributes as being indicative or common to the user: foot impedance, foot length, and type of arch, and wherein one or more of the user-specific attributes are accessed, by being read or stored, in the memory circuit and identified as being specific to the user. This information, in some embodiments, is later retrieved by the user, medical and/or security personnel, according to a data-access authorization protocol as might be established upon initial configuration for the user.

FIG. 7B shows an exemplary block diagram depicting the circuitry for interpreting signals received from electrodes. The input electrodes 705 transmit various electrical signals through the patient's body (depending on the desired biometric and physiological test to be conducted) and output electrodes 710 receive the modified signal as affected by a user's electrical impedance 715. Once received by the output electrodes 710, the modified signal is processed by processor circuitry 701 based on the selected test. Signal processing conducted by the processor circuitry 701 is discussed in more detail below (with regard to FIGS. 8A-B). In certain embodiments of the present disclosure, the circuitry within 701 is provided by Texas Instruments part # AFE4300.

FIGS. 8A-8B show example block diagrams depicting the circuitry for sensing and measuring the cardiovascular time-varying IPG raw signals and steps to obtain a filtered IPG waveform, consistent with various aspects of the present disclosure. The example block diagrams shown in FIGS. 8A-8B are separated into a leg impedance sub-circuit 800 and a foot impedance sub-circuit 805.

Excitation is provided by way of an excitation waveform circuit 810. The excitation waveform circuit 810 provides an excitation signal by way of various types of frequency signals (as is shown in FIG. 8A) or, more specifically, a square wave signal (as shown in FIG. 8B). As is shown in FIG. 8B, the square wave signal is a 5 V at a frequency between 15,625 Hz and 1 MHz is generated from a quartz oscillator (such as an ECS-100AC from ECS International, Inc.) divided down by a chain of toggle flip-flops (e.g. a CD4024 from Texas Instruments, Inc.), each dividing stage providing a frequency half of its input (i.e., 1 Mhz, 500 kHz, 250 kHz, 125 kHz, 62.5 kHz, 31.250 kHz and 15.625 kHz). This (square) wave is then AC-coupled, scaled down to the desired amplitude and fed to a voltage-controlled current source circuit 815. The generated current is passed through a decoupling capacitor (for safety) to the excitation electrode, and returned to ground through the return electrode (grounded-load configuration). Amplitudes of 1 and 4 mA peak-to-peak are typically used for Leg and Foot IPGs, respectively.

The voltage drop across the segment of interest (legs or foot) is sensed using an instrumentation differential amplifier (e.g., Analog Devices AD8421) 820. The sense electrodes on the scale are AC-coupled to the input of the differential amplifier 820 (configured for unity gain), and any residual DC offset is removed with a DC restoration circuit (as exemplified in Burr-Brown App Note Application Bulletin, SBOA003, 1991, or Burr-Brown/Texas Instruments INA118 datasheet).

The signal is then demodulated with a synchronous demodulator circuit 825. The demodulation is achieved in this example by multiplying the signal by 1 or −1 synchronously with the current excitation. Such alternating gain is provided by an operational amplifier and an analog switch (SPST), such as an ADG442 from Analog Devices. More specifically, the signal is connected to both positive and negative inputs through 10 kOhm resistors. The output is connected to the negative input with a 10 kOhm resistor as well, and the switch is connected between the ground and the positive input. When open, the gain of the stage is unity. When closed (positive input grounded), the stage acts as an inverting amplifier of the gain −1. Alternatively, other demodulators such as analog multipliers or mixers can be used.

Once demodulated, the signal is band-pass filtered (0.4-80 Hz) with a first-order band-pass filter circuit 830 before being amplified with a gain of 100 with a non-inverting amplifier circuit 835 (e.g., using an LT1058 operational amplifier from Linear Technologies). The amplified signal is further amplified by 10 and low-pass filtered (cut-off at 30 Hz) using a low-pass filter circuit 840 such as 2-pole Sallen-Key filter stage with gain. The signal is then ready for digitization and further processing. In certain embodiments, the amplified signal is passed through an additional low-pass filter circuit 845 to determine body or foot impedance.

In certain embodiments, the generation of the excitation voltage signal, of appropriate frequency and amplitude, is carried out by a microcontroller, such as MSP430 (Texas Instruments, Inc.). The voltage waveform is generated using the on-chip timers and digital input/outputs or pulse width modulation (PWM) peripherals, and scaled down to the appropriate voltage through fixed resistive dividers, active attenuators/amplifiers using on-chip or off-chip operational amplifiers, as well as programmable gain amplifiers or programmable resistors. Alternatively, the waveforms is directly generated by on- or off-chip digital-to-analog converters (DACs).

In certain embodiments, the shape of the excitation is not square, but sinusoidal. Such configuration reduces the requirements on bandwidth and slew rate for the current source and instrumentation amplifier. Harmonics, potentially leading to higher electromagnetic interference (EMI), are also reduced. Such excitation also reduce electronics noise on the circuit itself. Lastly, the lack of harmonics from sine wave excitation may provide a more flexible selection of frequencies in a multi-frequency impedance system, as excitation waveforms have fewer opportunities to interfere between each other. Due to the concentration of energy in the fundamental frequency, sine wave excitation are also more power-efficient.

In certain embodiments, the shape of the excitation is not square, but trapezoidal. The trapezoidal waves (or square waves whose edges have been smoothed out by a limited bandwidth or slew rate) provide an advantage in term of EMI and electronic noise due to the reduced harmonics.

To further reduce potential EMI, other strategies may be used, such as by dithering the square wave signal (i.e., introducing jitter in the edges following a fixed or random pattern) which leads to so-called spread spectrum signals, in which the energy is not localized at one specific frequency (or a set of harmonics), but rather distributed around a frequency (or a set of harmonics). An example of a spread-spectrum circuit suitable for Dual-IPG measurement is shown in FIG. 8B. Because of the synchronous demodulation scheme, phase-to-phase variability introduced by spread-spectrum techniques does not affect the impedance measurement. Such a spread-spectrum signal can be generated by, but not limited to, specialized circuits (e.g., Maxim MAX31C80, SiTime SiT9001), or generic microcontrollers (see Application Report SLAA291, Texas Instruments, Inc.). These spread-spectrum techniques can be combined with clock dividers to generate lower frequencies as well.

As may be clear to one skilled in the art, these methods of simultaneous measurement of impedance in the leg and foot are used for standard Body Impedance Analysis (BIA), with the aim of extracting relative content of total water, free-water, fat mass and others. Impedance measurements for BIA are typically done at frequencies ranging from kilohertz up to several megahertz. The multi-frequency measurement methods described above are readily used for such BIA, provided the circuit is modified so that the DC component of the impedance is not canceled by the instrumentation amplifier (no DC restoration circuit used). The high-pass filter can be implemented after the instrumentation amplifier, enabling the measurement of the DC component used for BIA. This multi-frequency technique can also be combined with traditional sequential measurements often used for BIA, in which the impedance is measured at several frequencies sequentially. These measurements can be repeated in several body segments for segmental BIAs, using a switch matrix to drive the current into the desired body segments.

While FIG. 6 shows a circuit and electrode configuration suitable to measure two different segments (legs and one foot), this approach is not readily extendable to more segments due to the shared current return electrode (ground). To overcome this limitation, and in particular to provide simultaneous measurements in both feet, the system is augmented with analog switches to provide time-multiplexing of the impedance measurements in the different segments. This multiplexing includes a one-time sequencing (each segment is measured once), or interleaved at a high-enough frequency so that the signal is simultaneously measured on each segment. The minimum multiplexing rate for proper reconstruction is twice the bandwidth of the measured signal, based on signal processing theory, which equals to about 100 Hz for the impedance signal considered here. The rate also allows for the signal path to settle in between switching, usually limiting the maximum multiplexing rate. Referring to FIG. 13A, as an example, one cycle starts the measurement of the leg impedance and left foot impedances (similarly to previously described, sharing a common return electrode), but then follow with a measurement of the right foot after reconfiguring the switches. Typical switch configurations for the various measurements are shown in the table which follows.

|  | Switch #1 (Sw1) | Switch #2 (Sw2) | Switch #3 (Sw3) | Switch #4 (Sw4) |
|---|---|---|---|---|
| Legs | A | A or B | A or B | A |
| Right Foot | A | A or B | B | A |
| Left Foot | B | B | A or B | B |

Since right and left feet are measured sequentially, in some embodiments, a unique source (at the same frequency) is used to measure both, providing that the current source is not connected to the two feet simultaneously through the switches, in which case the current would be divided between two paths. Another example embodiment includes a fully-sequential measurement, using a single current source (at a single frequency) successively connected to the three different injection electrodes, with the proper switch configuration sequence (no split current path).

In certain embodiments, the measurement of various body segments, and in particular the legs, right foot and left foot, is achieved simultaneously due to as many floating current sources as segments to be measured, running at separate frequency so they can individually be demodulated. Such configuration is exemplified in FIG. 13B for three segments (legs, right and left feet). Such configuration provides true simultaneous measurements without the added complexity of time-multiplexing/demultiplexing, and associated switching circuitry. An example of such floating current source can be found in Plickett, et al., Physiological Measurement, 32 (2011). Another approach to floating current sources is the use of transformer-coupled current sources (as depicted in FIG. 13C). Using transformers to inject current into the electrodes enables the use of simpler, grounded-load current sources on the primary, while the electrodes are connected to the secondary. Turn ratio is typically 1:1, and since frequencies of interest for impedance measurement are typically in the 10-1000 kHz (occasionally 1 kHz for BIA), relatively small transformers are used. In order to limit the common mode voltage of the body, one of the electrodes in contact with the foot is grounded.

While certain embodiments presented in the above specification use current sources for excitation, it should be clear to a person skilled in the art that the excitation can also be performed by a voltage source, where the resulting injection current is monitored by a current sense circuit so that impedance is derived by the ratio of the sensed voltage (on the sense electrodes) over the sensed current (injected in the excitation electrodes).

It should be noted that broadband spectroscopy methods can also be used for measuring impedances at several frequencies. Such technique has a lower EMI and simultaneous measurement of impedances at numerous frequencies. These methods typically use a chirp signal, a noise signal or an impulse signal to excite the load (impedance) at many frequencies simultaneously, while sampling the resulting response at high frequency so as to allow the computation (usually in the frequency domain) of the impedance over the desired frequency range. Combined with time-multiplexing and current switching described above, multi-segment broadband spectroscopy can be readily achieved.

Various aspects of the present disclosure are directed toward robust timing extraction of the blood pressure pulse in the foot which is achieved by means of a two-step processing. In a first step, the usually high-SNR Leg IPG is used to derive a reference (trigger) timing for each heart pulse. In a second step, a specific timing in the lower-SNR Foot IPG is extracted by detecting its associated feature within a restricted window of time around the timing of the Leg IPG. Such guided detection leads to a naturally more robust detection of foot timings.

FIG. 9 shows an example block diagram depicting signal processing steps to obtain fiducial references from the individual Leg IPG "beats," which are subsequently used to obtain fiducials in the Foot IPG, consistent with various aspects of the present disclosure. In the first step, as shown in block 900, the Leg IP and the Foot IPG are simultaneously measured. As shown at 905, the Leg IPG is low-pass filtered at 20 Hz with an 8-pole Butterworth filter, and inverted so that pulses have an upward peak. The location of the pulses is determined by taking the derivative of this signal, integrating over a 100 ms moving window, zeroing the negative values, removing the large artifacts by zeroing values beyond 15× the median of the signal, zeroing the values below a threshold defined by the mean of the signal, and searching for local maxima. Local maxima closer than a defined refractory period of 300 ms to the preceding ones are dismissed. The result is a time series of pulse reference timings.

As is shown in 910, the foot IPG is low-pass filtered at 25 Hz with an 8-pole Butterworth filter and inverted (so that pulses have an upward peak). Segments starting from the timings extracted (915) from the Leg IPG (reference timings) and extending to 80% of the previous pulse interval, but no longer than one second, are defined in the Foot IPG. This defines the time windows where the Foot IPG is expected to occur, avoiding misdetection outside of these windows. In each segment, the derivative of the signal is computed, and the point of maximum positive derivative (maximum acceleration) is extracted. The foot of the IPG signal is computed using an intersecting tangent method, where the fiducial (920) is defined by the intersection between a first tangent to the IPG at the point of maximum positive derivative and a second tangent to the minimum of the IPG on the left of the maximum positive derivative within the segment.

The time series resulting from this two-step extraction is used in conjunction with another signal to facilitate additional processing. In the present disclosure, these timings are used as reference timings to improve the SNR of BCG signals to subsequently extract intervals between a timing of the BCG (typically the I-wave) and the Foot IPG for the purpose of computing the PWV, as previously disclosed in U.S. 2013/0310700 (Wiard). In certain embodiments, the timings of the Leg IPG are used as reference timings to improve the SNR of BCG signals, and the foot IPG timings are used to extract intervals between timing fiducials of the improved BCG (typically the I-wave) and the Foot IPG for the purpose of computing the PTT and the (PWV).

In certain embodiments, the processing steps include an individual pulse SNR computation after individual timings are extracted, either in Leg IPG or Foot IPG. Following the computation of the SNRs, pulses with a SNR below a threshold value are eliminated from the time series, in order to prevent propagating noise in subsequent processing steps. The individual SNRs are computed in a variety of methods known to a person skilled in the art. For instance, an estimated pulse is computed by ensemble averaging segments of signal around the pulse reference timing. The noise associated with each pulse is defined as the difference between the pulse and the estimated pulse. The SNR is the ratio of the root-mean-square (RMS) value of the estimated pulse over the RMS value of the noise for that pulse.

In certain embodiments, the time interval between the Leg IPG pulses, (as detected by the above-mentioned methods), and the Foot IPG pulses, also detected by the above-mentioned methods, is extracted. The Leg IPG measuring a pulse occurring earlier in the legs is compared to the pulse from the Foot IPG, the interval between these two being related to the propagation speed in the lower body, i.e., the peripheral vasculature. This provides complementary information to the interval extracted between the BCG and the Foot IPG, for instance, and can be used to decouple central versus peripheral vascular properties. It is also complementary to information derived from timings between the BCG and the Leg ICG.

In FIG. 10, the Leg IP and the Foot IPG are simultaneously measured (1000), the Leg IPG is low-pass filtered (1005), the foot IPG is low-pass filtered (1010), and segments starting from the timings are extracted (1015) from the Leg IPG (reference timings). The segments of the Foot IPG extracted based on the Leg IPG timings are ensemble-averaged (1020) to produce a higher SNR Foot IPG pulse. From this ensemble-averaged signal, the start of the pulse is extracted using the same intersecting tangent approach as described earlier. This approach enables the extraction of accurate timings in the Foot IPG even if the impedance signal is dominated by noise. These timings are used together with timings extracted from the BCG for the purpose of computing the PTT and (PWV). Timings derived from ensemble-averaged waveforms and individual waveforms are both extracted, for the purpose of comparison, averaging and error-detection.

Specific timings that can be extracted from the IPG pulses (from either leg or foot) are related (but not limited) to the peak of the pulse, to the minimum preceding the peak, or to the maximum second derivative (maximum rate of acceleration) preceding the point of maximum derivative. An IPG pulse and the extraction of a fiducial (1025) in the IPG can also be performed by several other signal processing methods, including (but not limited to) template matching, cross-correlation, wavelet-decomposition, or short window Fourier transform.

In certain embodiments, a dual-Foot IPG is measured, allowing the detection of blood pressure pulses in both feet. Such information is used for diagnostic of peripheral arterial diseases (PAD) by comparing the relative PATs in both feet to look for asymmetries. It is be used to increase the robustness of the measurement by allowing one foot to have poor contact with electrodes (or no contact at all). SNR measurements are used to assess the quality of the signal in each foot, and to select the best signal for downstream analysis. Timings extracted from each foot are compared and set to flag potentially inaccurate PWV measurements due to arterial peripheral disease, in the event these timings are different by more than a defined threshold. Alternatively, timings from both feet are pooled to increase the overall SNR if their difference is below a defined threshold.

In certain embodiments, a PWV is measured, where the IPG is augmented by the addition of BCG sensing into the weighing scale to determine characteristic fiducials between the BCG and Leg IPG trigger, or the BCG and Foot IPG. The BCG sensors are comprised typically of the same strain gage set used to determine the bodyweight of the user. The load cells are typically wired into a bridge configuration to create a sensitive resistance change with small displacements due to the ejection of the blood into the aorta, where the circulatory or cardiovascular force produce movements within the body on the nominal order of 1-3 Newtons. BCG forces can be greater than or less than the nominal range in cases such as high or low cardiac output.

FIG. 11 shows an example configuration to obtain the PTT, using the first IPG as the triggering pulse for the Foot IPG and BCG, consistent with various aspects of the present disclosure. The I-wave of the BCG 1100 as illustrated normally depicts the headward force due to cardiac ejection of blood into the ascending aorta which can be used as a timing fiducial indicative of the pressure pulse initiation of the user's proximal aorta relative to the user's heart. The J-wave is also indicative of timings in the systole phase and also incorporates information related to the strength of cardiac ejection and the ejection duration. The K-Wave also provides systolic and vascular information of the user's aorta. In some embodiments, the characteristic timings of these and other BCG waves are used as fiducials that are related to fiducials of the IPG signals of the present disclosure.

FIG. 12 shows another example of a scale 1200 with interleaved foot electrodes 1205 to inject and sense current from one foot to another foot, and within one foot, consistent with various aspects of the present disclosure. FIG. 13A-C3 shows various examples of a scale 1300 with interleaved foot electrodes 1305 to inject and sense current from one foot to another foot, and measure Foot IPG signals in both feet, consistent with various aspects of the present disclosure. FIGS. 14A-D shows an example breakdown of a scale 1400 with interleaved foot electrodes 1405 to inject and sense current from one foot to another foot, and within one foot, consistent with various aspects of the present disclosure.

FIG. 15 shows an example block diagram of circuit-based building blocks, consistent with various aspects of the present disclosure. The various circuit-based building blocks shown in FIG. 15, in accordance with some embodiments, are implemented in connection with the various aspects discussed herein. In the example shown, the block diagram includes foot electrodes 1500 that collects the IPG signals. Further, the block diagram includes strain gauges 1505, and an LED/photosensor 1510. The foot electrodes 1500 is configured with a leg impedance measurement circuit 1515, a foot impedance measurement circuit 1520, and an optional second foot impedance measurement circuit 1525. The leg impedance measurement circuit 1515, the foot impedance measurement circuit 1520, and the optional second foot impedance measurement circuit 1525 report the measurements collected to a processor circuit 1545.

The processor circuit 1545 also collects data from a weight measurement circuit 1530 and an optional balance measurement circuit 1535 that are configured with the strain gauges 1505. Further, an optional photoplethysmogram (PPG) measurement circuit 1540, which collects data from the LED/photosensor 1510, provides data to the processor circuit 1545.

The processor circuit 1545 is powered via a power circuit 1550. Further, the processor circuit 1545 also collects user input data from a user interface 1555 that can include a touch screen and/or buttons. The data collected/measured by the processor circuit 1545 is shown to the user via a display 1560. Additionally, the data collected/measured by the processor circuit 1545 is stored in a memory circuit 1580. Further, the processor circuit 1545 can optionally control a haptic feedback circuit 1565, a speaker or buzzer 1570, a wired/wireless interface 1575, and an auxiliary sensor 1585.

FIG. 16 shows an example flow diagram, consistent with various aspects of the present disclosure. As shown in block

1600, a PWV length is entered. As is shown in block 1605, a user's weight, balance, leg, and foot impedance are measured (as is consistent with various aspects of the present disclosure). As is shown at block 1610, the integrity of signals is checked (e.g., signal to noise ratio). If the signal integrity check is not met, the user's weight, balance, leg, and foot impedance are measured again (block 1605). If the signals integrity check is met, the leg impedance pulse timings are extracted (as is shown at block 1615). As is shown at block 1620, foot impedance and pulse timings are extracted, and as is shown at block 1625, BCG timings are extracted. As is shown at block 1630, a timings quality check is performed. If the timings quality check is not validated, the user's weight, balance, leg and foot impedance are again measured (block 1605). If the timings quality check is validated, the PWV is calculated (as is shown at block 1635). Finally, as is shown at block 1640, the PWV is displayed to the user.

FIG. 17 shows an example scale 1700 communicatively coupled to a wireless device, consistent with various aspects of the present disclosure. As described herein, a display 1705 displays the various aspects measured by the scale 1700. The scale can also wirelessly broadcast the measurements to a wireless device 1710.

FIGS. 18A-C show example impedance as measured through different parts of the foot based on the foot position, consistent with various aspects of the present disclosure. For instance, example impedance measurement configurations are implemented using a dynamic electrode configuration for measurement of foot impedance and related timings, consistent with various aspects of the present disclosure. Dynamic electrode configuration are implemented using independently-configurable electrodes to optimize the impedance measurement. As shown in FIG. 18A, interleaved electrodes 1800 are connected to an impedance processor circuit 1805 to determine foot length, foot position, and/or foot impedance. As is shown in FIG. 18B, an impedance measurement is determined regardless of foot position 1810 based on measurement of the placement of the foot across the electrodes 1800. This is based in part in the electrodes 1800 that are engaged (blackened) and in contact with the foot (based on the foot position 1810), which is shown in FIG. 18C.

More specifically regarding FIG. 18A, the configuration includes connection/de-connection of the individual electrodes 1800 to the impedance processor circuit 1805, their configuration as current-carrying electrodes (injection or return), sense electrodes (positive or negative), or both. The configuration can either be preset based on user information, or updated at each measurement (dynamic reconfiguration) to optimize a given parameter (impedance SNR, measurement location). The system, for instance, algorithmically determines which electrodes under the foot to use in order to obtain the highest SNR in the pulse impedance signal. Such optimization algorithm includes iteratively switching configurations and measuring the resulting impedance, then selecting the best-suited configuration. Alternatively, the system first, through a sequential impedance measurement between each individual electrode 1800 and another electrode in contact with the body (such as an electrode in electrode pair 205 on the other foot), determines which electrodes are in contact with the foot. By determining the two most apart electrodes, the foot size is determined. Heel location is determined in this manner, as can other characteristics such as foot arch type. These parameters, in some embodiments, are used to determine programmatically (in an automated manner by CPU/logic circuitry) which electrodes are selected for current injection and return (as well as sensing if a Kelvin connection issued) in order to obtain the best foot IPG.

In various embodiments involving the dynamically reconfigurable electrode array 1800/1805, an electrode array set is selected to measure the same portion (or segment) of the foot, irrespective of the foot location on the array. FIG. 18B illustrates the case of several foot positions on a static array (a fixed set of electrodes are used for measurement at the heel and plantar/toe areas, with a fixed gap of an inactive electrode or insulating material between them). Depending on the position of the foot, the active electrodes are contacting the foot at different locations, thereby sensing a different volume (or segment) of the foot. If the IPG is used by itself (e.g., for heart measurement), such discrepancies may be non-consequential. However, if timings derived from the IPG are referred to other timings (e.g., R-wave from the ECG, or specific timing in the BCG), such as for the calculation of a PTT or PWV, the small shifts in IPG timings due to the sensing of slightly different volumes in the foot (e.g., if the foot is not always placed at the same position on the electrodes) introduces an error in the calculation of the interval. Such location variations can occur in the day-to-day use of the scale. With respect to FIG. 18B for instance, the timing of the peak of the IPG from the foot placement on the right (sensing the toe/plantar region) is later than from the foot placement on the left, which senses more of the heel volume (the pulse reaches first the heel, then the plantar region). Factors influencing the magnitude of these discrepancies include foot shape (flat or not) and foot length.

Various embodiments address challenges relating to foot placement. FIG. 18C shows an example embodiment involving dynamic reconfiguration of the electrodes to reduce such foot placement-induced variations. As an example, by sensing the location of the heel first (as described above), only a subset of electrodes under the heel are activated, and another subset of electrodes separated by a fixed distance (1800). The other electrodes (e.g., unused electrodes) are left disconnected. The sensed volume is therefore the same, producing consistent timings. The electrode configuration leading to the most consistent results are informed by the foot impedance, foot length, the type of arch (all of which can be measured by the electrode array as shown above), but also by the user ID (foot information can be stored for each user, then looked up based on automatic user recognition or manual selection (e.g., in a look-up-table stored for each user in a memory circuit accessible by the CPU circuit in the scale)).

Accordingly, in certain embodiments, the impedance-measurement apparatus measures impedance using a plurality of electrodes contacting one foot and with at least one other electrode (typically many) at a location distal from the foot. The plurality of electrodes (contacting the one foot) is arranged on the platform and in a pattern configured to inject current signals and sense signals in response thereto, for the same segment of the foot so that the timing of the pulse-based measurements does not vary simply because the user placed the one foot at a slightly different position on the platform or scale. Thus, in FIG. 18A, the foot-to-electrode locations for the heel are different locations than that shown in FIGS. 18B and 18C. As this different foot placement occurs from day to day for the user, the timing and related impedance measurements are the same (internal) segment of the foot. By having the computer processor circuit inject current and sense responsive signals to first locate the foot on the electrodes (e.g., sensing where positions of the foot's heel plantar regions and/or toes), the pattern of foot-to-electrode locations permits the foot to move laterally, horizontally and both laterally and horizontally via the different electrode locations, while collecting impedance measurements relative to the same segment of the foot.

The BCG/IPG system, in some embodiments, is used to determine the PTT of the user, by identification of the average I-Wave or derivative timing near the I-Wave from a plurality of BCG heartbeat signals obtained simultaneously with the Dual-IPG measurements of the present disclosure to determine the relative PTT along an arterial segment between the ascending aortic arch and distal pulse timing of the user's lower extremity. In certain embodiments, the BCG/IPG system is used to determine the PWV of the user, by identification of the characteristic length representing the length of the user's arteries, and by identification of the average I-Wave or derivative timing near the I-Wave from a plurality of BCG heartbeat signals obtained simultaneously with the Dual-IPG measurements of the present disclosure to determine the relative PTT along an arterial segment between the ascending aortic arch and distal pulse timing of the user's lower extremity. The system of the present disclosure and alternate embodiments is suitable for determining the arterial stiffness (or arterial compliance) and/or cardiovascular risk of the user regardless of the position of the user's feet within the bounds of the interleaved electrodes. In certain embodiments, the weighing scale system incorporates the use of strain gage load cells and six or eight electrodes to measure a plurality of signals including: bodyweight, BCG, body mass index, fat percentage, muscle mass percentage, and body water percentage, heart rate, heart rate variability, PTT, and PWV measured simultaneously or synchronously when the user stands on the scale to provide a comprehensive analysis of the health and wellness of the user.

In other certain embodiments, the PTT and PWV are computed using timings from the Leg IPG or Foot IPG for arrival times, and using timings from a sensor located on the upper body (as opposed to the scale measuring the BCG) to detect the start of the pulse. Such sensor may include an impedance sensor for impedance cardiography, a hand-to-hand impedance sensor, a photoplethysmogram on the chest, neck, head, arms or hands, or an accelerometer on the chest (seismocardiograph) or head.

Communication of the biometric information is another aspect of the present disclosure. The biometric results from the user are stored in the memory on the scale and displayed to the user via a display on the scale, audible communication from the scale, and/or the data is communicated to an external device such as a computer, smart phone, or tablet computing device. The communication occurs directly to the external device with a wired connection, or is sent to the external device through wireless communication protocols such as Bluetooth or WiFi. Computations such as signal analyses described therein may be carried out locally on the scale, in a smartphone or computer, or in a remote processor (cloud computing).

Other aspects of the present disclosure are directed toward apparatuses or methods that include the use of at least two electrodes that contact feet of a user. Further, circuitry is provided to determine a pulse arrival time at the foot based on the recording of two or more impedance signals from the set of electrodes. Additionally, a second set of circuitry is provided to extract a first pulse arrival time from a first impedance signal and use the first pulse arrival time as a timing reference to extract and process a second pulse arrival time in a second impedance signal.

As disclosed herein and in connection with Table 1 (and this appendix), the example apparatuses and processes involve generating data relevant to the user and/or provide feedback with respect to the user's physiological health and fitness level. Based on such information, in some embodiments, health-monitoring alerts and recommendations is provided to the user and other personnel.

One might appreciate that the fitness assessment, as described above in connection with FIGS. 1A-1C, can be performed alone or in combination with the number of embodiments and/or specific features described herein, for example as described in FIGS. 2-18. Further embodiments include the apparatus communicating with external devices. For example, as shown in FIG. 19 applications (e.g., apps) are provided on the external devices (e.g., smart phones, tablets, etc.) for customization of various user health goals, training regimes, health diagnostics and other modalities, responsive to the communicated user data.

FIG. 20 depicts such wireless communications via measurement devices on behalf of an elderly user, in which the user's physiological data is sent to an external device (e.g., dashboard) and is received by a caregiver. The communicated data, in some embodiments, includes health profiles and treatment regimes. FIG. 21 is commensurate with FIG. 20 with respect to the measurement devices and communication of physiological data, with applications directed to a middle-aged user. This figure also discloses that the user data is collected and compared over time, and deviations from personal norms and population norms are measured and captured in this data, among other measurement criteria.

In some embodiments, as previously discussed, the apparatus tracks physiological parameters of the user over time. The apparatus includes interface circuitry driving the display. The interface circuitry is be located on the apparatus and/or on an external device. The display outputs a signal indicative of the measured physiological parameters to the interface circuit. The interface circuit, responsive to the output signal, tracks physiological parameters of the user over time. In various embodiments, the physiological parameters monitored and/or tracked include recovery parameters.

FIGS. 19, 20 and 21, illustrate different external devices that the data can be communicated to. FIG. 19 illustrates communicating the feedback to an external device of the user, e.g., a cell phone. The user can customize individual goals and/or adjust an optimal training regimen using the external device. Example external devices include a wearable wrist device, a portable remote device, e.g. a cell phone, a tablet, a laptop computer, and a combination thereof. FIG. 20 illustrates communicating the feedback to an external device of a third party, e.g., a caregiver. In such embodiments, the third party can evaluate and/or monitor the health of the user. FIG. 21 illustrates communicating the feedback to the external device of the user. The user, in such embodiments, can evaluate and/or monitor their own health. That is, in various embodiments, the apparatus is used to train for fitness purposes and/or monitor the health of the user.

A variety of physiological and user categories directed to aspects in connection with Table 1 and implemented using the apparatuses and/or methods described herein are provided below. Collectively, it will be appreciated that FIGS. 19-21, along with Table 1 and the remaining disclosure herein provide a wide range of implementations and embodiments. Accordingly, aspects of the present disclosure are directed to inter alia, the following physiological and user categories:

Elder Care
    Comprehensive trending of wellness in elderly with security information delivered to caregiver including:
        Cardiovascular health (PWV, heart rate)
        Weight optimization
        Hydration
        Medication reminder
    Example Analytic concepts:
        Deviations from population norm (screening)
        Deviation from personal norm (trending, alerting)
    Information Provided to Caregiver leading to:
        Evaluate heart health, dietary optimization, de-cluttering environment to prevent falls, reminders to hydrate and take medication
    Example uses:
        Multi-generational home
        Independent elderly home
        Nursing home
        Rehabilitation
General Health & Wellbeing
    Actionable Feedback for Optimizing Health and Screening:
        Cardiovascular health (PWV and heart rate)
        Weight optimization
        Body composition analysis-muscle, fat, hydration
    Example Analytic concepts:
        Deviations from population norm (screening)
        Deviation from personal norm (trending, alerting)
    Meaningful information about:
        Exercise, diet change, and heart health
    Example Uses:
        Home
        General practice medical office
        Health club/gym
Fitness uses
    Individualized coaching for training to meet personal health goals. Feedback over time on what is and is not working in training
        Fitness level (PWV, morning resting heart rate and heart rate recovery)
        Weight optimization
        Body composition analysis, hydration
    Example Analytic concepts:
        Optimizing personal norm to exceed population norm
    Meaningful information about exercise regimens that yield the best results to meet goals
    Combine scale based data with data from other sources, data is analyzed, and content and context pushed to
        mobile devices
        Wearable devices
        Phone
    Example uses:
        Home
        Health clubs Reference may also be made to published patent documents, U.S. Patent Publication No. 2010/0094147 and No. 2013/0310700, which are, together with the references cited therein, herein fully incorporated by reference for the purposes of sensors and sensing technology. The aspects discussed therein may be implemented in connection with one or more of embodiments and implementations of the present disclosure (as well as with those shown in the figures). In view of the description herein, those skilled in the art will recognize that many changes may be made thereto without departing from the spirit and scope of the present disclosure.

As illustrated herein, various circuit-based building blocks and/or modules may be implemented to carry out one or more of the operations and activities described herein shown in the block-diagram-type figures. In such contexts, these building blocks and/or modules represent circuits that carry out one or more of these or related operations/activities. For example, in certain of the embodiments discussed above (such as the pulse circuitry modularized as shown in FIGS. 8A-B), one or more blocks/modules are discrete logic circuits or programmable logic circuits configured and arranged for implementing these operations/activities, as in the circuit blocks/modules shown. In certain embodiments, the programmable circuit is one or more computer circuits programmed to execute a set (or sets) of instructions (and/or configuration data). The instructions (and/or configuration data) can be in the form of firmware or software stored in and accessible form, a memory (circuit). As an example, first and second modules/blocks include a combination of a CPU hardware-based circuit and a set of instructions in the form of firmware, where the first module/block includes a first CPU hardware circuit with one set of instructions and the second module/block includes a second CPU hardware circuit with another set of instructions.

Accordingly, aspects of the present disclosure are directed to inter alia, the following apparatuses, systems, and/or methods:

A measuring apparatus comprising:
    A base unit including
        A platform area defined by a support structure,
        A bezel extending along a perimeter of the platform area,
        The support structure configured and arranged to transfer the force asserted by a user to the bezel and through a plurality of load cells,
        A display configured and arranged to present information and images through the support structure,
        A plurality of translucent electrodes embedded within the support structure, a first translucent electrode configured and arranged for contacting one foot of a user and a second electrode configured and arranged for contacting the user at a location along a lower limb of the user that does not include the one foot, and
        Pulse-processing circuitry communicatively coupled to, and configured and arranged with, the plurality of translucent electrodes to
            Obtain a plurality of impedance-measurement signals,
            Extract pulse characteristic signals from at least one of the impedance-measurement signals, and
            Based on the extracted pulse characteristic signals, determine a condition of the user.
    The base unit houses the pulse-processing circuitry, and the pulse characteristic signals indicate pulse arrival times.
    The display includes a capacitive matrix on its surface, and is configured and arranged to respond to touch-capacitive signals indicative of a user's position and movement on the support glass, the support glass communicatively coupled to the display, and configured and arranged to transmit said touch-capacitive signals from the user on the support structure to the capacitive matrix.
    The display is configured and arranged to present one of the following: videos, images, and animations, when the base unit is idle.

The base unit further includes
  A camera configured and arranged to capture image data of an area around the base unit;
  Image processing circuitry configured and arranged to receive the captured image data from the camera and determine color and pattern themes associated with the image data and/or alternatively;
  A single microphone or microphone array configured and arranged to detect audible sounds to determine the presence of a user; and
  The display further configured and arranged to present an image indicative of the area around the base unit, based on the image data processed by the image processing circuitry, when the base unit is idle.

Based upon the above discussion and illustrations, those skilled in the art will readily recognize that various modifications and changes may be made to the present disclosure without strictly following the exemplary embodiments and applications illustrated and described herein. For example, the input terminals as shown and discussed may be replaced with terminals of different arrangements, and different types and numbers of input configurations (e.g., involving different types of input circuits and related connectivity). Such modifications do not depart from the true spirit and scope of the present disclosure, including that set forth in the following claims.

What is claimed is:

1. An apparatus, comprising:
  a user wearable device including signal communication circuitry and output circuitry configured and arranged to communicate selected data to a user and to provide monitored selected data indicative of physiological parameters;
  a weighing scale comprising:
    a platform region configured and arranged with an area for the user to stand;
    user-targeted circuitry configured and arranged to communicate user-specific data between the user and the user-targeted circuitry;
    a support structure including the platform region and sensor circuitry therein, the sensor circuitry including current-impedance electrodes configured and arranged to contact the user, and the sensor circuitry configured and arranged to obtain a plurality of impedance-measurement signals via the current-impedance electrodes and to determine physiological signals of the user using the plurality of impedance-measurement signals, the platform region configured and arranged to engage the user with the sensor circuitry while the user stands on the platform region, and to collect physiological data from the user via the sensor circuitry, and
    a display configured and arranged with the support structure for displaying data through the platform region for view by the user while the user stands on the platform region, configured and arranged with the user-targeted circuitry to:
      monitor a plurality of physiological signals of the user while the user is standing on the platform region; and
      select data indicative of a physiological parameter of the user, for display on one of the user wearable device and the display of the weighing scale, based on a threshold value and the plurality of physiological signals.

2. The apparatus of claim 1, wherein the user wearable device includes a wrist wearable device and the plurality of physiological signals of the user include ballistocardiogram (BCG) signals.

3. The apparatus of claim 1, wherein the weighing scale further include communication circuitry configured and arranged with the display, and configured to output a signal that includes the data indicative of the physiological parameter to the user wearable device.

4. The apparatus of claim 3, wherein the wearable device further includes a display to communicate the physiological parameter to the user, and the wearable device further includes circuitry configured and arranged to update physiological data of the user based on the communicated physiological parameter.

5. The apparatus of claim 1, wherein the current-impedance electrodes are configured and arranged at the platform region to contact feet of the user, and further including current-driving circuitry configured and arranged to pass electrical current, for obtaining the impedance-measurement signals, through one or more of the user's feet.

6. The apparatus of claim 1, wherein the display configured and arranged with the user-targeted circuitry to select data indicative of the physiological parameter of the user based on the threshold value includes disregarding one of the physiological signals in response the one physiological signal having a signal integrity that is below the threshold value.

7. The apparatus of claim 6, wherein the display configured and arranged with the user-targeted circuitry to determine a signal integrity of each of the plurality of physiological signals and use the determined signal integrities to select data indicative of the physiological parameter.

8. The apparatus of claim 7, wherein the display configured and arranged with the user-targeted circuitry to average a subset of the plurality of physiological signals that have signal integrities above the threshold value and select the average as the data indicative of the physiological parameter.

9. The apparatus of claim 1, wherein the signal communication circuitry includes a wireless signal communication configured and arranged to wirelessly communicate selected data with the weighing scale.

10. The apparatus of claim 1, wherein the selected data includes data indicative of at least one of exercise habits, dietary habits, and sleeping habits.

11. An apparatus, comprising:
  a user wearable device including circuitry configured and arranged to monitor selected data indicative of physiological parameters and signal communication circuitry and output circuitry configured and arranged to communicate the selected data to a weighing scale;
  the weighing scale comprising:
    a communication circuitry configured and arranged with a display of the weighing scale to receive the data indicative of the physiological parameters from the communication circuitry of the user wearable device;
    a platform region configured and arranged with an area for the user to stand;
    user-targeted circuitry configured and arranged to communicate user-specific data between the user and the user-targeted circuitry;
    a support structure including the platform region and sensor circuitry therein, the sensor circuitry including current-impedance electrodes configured and arranged to contact the user, and the sensor circuitry configured and arranged to obtain a plurality of impedance-measurement signals via the current-impedance electrodes and to determine physiological signals of the user using the plurality of impedance-measurement signals, the platform region configured and arranged to engage the user with the sensor circuitry while the user stands on the platform region, and to collect physiological data from the user via the sensor circuitry, and a display configured and arranged with the support structure for displaying data through the platform region for view by the user while the user stands on the platform region, configured and arranged with the user-targeted circuitry to:

monitor a plurality of physiological signals of the user while the user is standing on the platform region; and select data indicative of a physiological parameter of the user, for display on one of the user wearable device and the display of the weighing scale, based on a threshold value and at least one of the plurality of physiological signals and the data indicative of the physiological parameters received from the user wearable device.

12. The apparatus of claim 11, wherein the display is further configured and arranged with the user-targeted circuitry to select data indicative of the physiological parameter of the user based on the threshold value includes disregarding one of the physiological signals in response to the one physiological signal having a signal integrity that is below the threshold value.

13. The apparatus of claim 12, wherein the display is further configured and arranged with the user-targeted circuitry to determine a signal integrity of each of the plurality of physiological signals and use the determined signal integrities to select data indicative of the physiological parameter.

14. The apparatus of claim 11, wherein the display on one of the user wearable device and the display of the weighing scale is further configured and arranged with the user-targeted circuitry to communicate assessed fitness to the user as feedback based on the physiological parameter.

15. The apparatus of claim 14, wherein the assessed fitness communicated by the display and the user-targeted circuitry includes feedback for improving or maintaining a level of fitness of the user.

16. The apparatus of claim 14, wherein the user wearable device is further configured and arranged to communicate data to the weighing scale, the data selected from the group consisting of: exercise data, dietary data, GPS and route data, and a combination thereof.

17. The apparatus of claim 14, wherein the assessed fitness includes the physiological parameter and recommendations regarding the physiological parameter.

18. The apparatus of claim 11, wherein the display on one of the user wearable device and the display of the weighing scale is further configured and arranged with the user-targeted circuitry to communicate coaching data to the user as feedback based on the physiological parameter and data from the user wearable device over time.

19. The apparatus of claim 11, wherein the display on one of the user wearable device and the display of the weighing scale is further configured and arranged with the user-targeted circuitry to communicate assessed fitness to the user as feedback by tracking the physiological parameter over time and comparing the tracked physiological parameter to prior-assessed user norms or other population norms.

* * * * *